United States Patent
Leuthardt et al.

(10) Patent No.: US 12,290,371 B2
(45) Date of Patent: May 6, 2025

(54) INTRACALVARIAL BCI SYSTEMS AND METHODS FOR THEIR MAKING, IMPLANTATION AND USE

(71) Applicant: Inner Cosmos Inc., Scotts Valley, CA (US)

(72) Inventors: Eric Claude Leuthardt, St. Louis, MO (US); Meron Gribetz, New York City, NY (US); Daniel W. Moran, Ballwin, MO (US)

(73) Assignee: Inner Cosmos Inc., Scotts Valley, CA (US)

( * ) Notice: Subject to any disclaimer, the term of this patent is extended or adjusted under 35 U.S.C. 154(b) by 945 days.

(21) Appl. No.: 17/428,700

(22) PCT Filed: Jan. 23, 2020

(86) PCT No.: PCT/IB2020/050527
§ 371 (c)(1),
(2) Date: Aug. 5, 2021

(87) PCT Pub. No.: WO2020/161555
PCT Pub. Date: Aug. 13, 2020

(65) Prior Publication Data
US 2022/0117540 A1    Apr. 21, 2022

Related U.S. Application Data

(60) Provisional application No. 62/802,245, filed on Feb. 7, 2019.

(51) Int. Cl.
*A61N 1/375* (2006.01)
*A61B 5/00* (2006.01)
(Continued)

(52) U.S. Cl.
CPC ............ *A61B 5/369* (2021.01); *A61B 5/0006* (2013.01); *A61B 5/293* (2021.01); *A61B 5/6878* (2013.01);
(Continued)

(58) Field of Classification Search
CPC .............. A61N 1/0531; A61N 1/36128; A61N 1/37235; A61N 1/37514; A61B 5/0006; A61B 5/293; A61B 5/6878
See application file for complete search history.

(56) References Cited

U.S. PATENT DOCUMENTS 4,328,813 A    5/1982  Ray
4,551,149 A   11/1985  Sciarra
(Continued)

FOREIGN PATENT DOCUMENTS

CA    3098311    11/2019
CN    105916547   8/2016
(Continued)

OTHER PUBLICATIONS

Notice of Reason(s) for Rejection Dated Jan. 9, 2024 From the Japan Patent Office Re. Application No. 2020-570860 and Its Translation Into English. (16 Pages).
(Continued)

*Primary Examiner* — Eun Hwa Kim

(57) ABSTRACT

An intra-calvarial implant (ICI) includes a housing including a sealed compartment having a top part, a bottom part and a side wall, and a current directing mechanism extending from the bottom part of the sealed compartment. The ICI also includes one or more electrodes for sensing electrical signals from the brain and/or for electrically stimulating one or more regions of the brain. The ICI includes at least one auxiliary electrode (that may be a reference and/or source/sink electrode) and an electronic circuitry module (ECM),
(Continued)

sealingly disposed within the sealed compartment and operatively connected to the one or more electrodes and to the at least one reference electrode. The ECM controls the operation of the ICI and wirelessly communicates with an external telemetry device. The ICI includes a power harvesting device electrically connected to the ECM of the ICI for providing power thereto.

54 Claims, 24 Drawing Sheets

(51) Int. Cl.

| | |
|---|---|
| A61B 5/293 | (2021.01) |
| A61B 5/369 | (2021.01) |
| A61N 1/05 | (2006.01) |
| A61N 1/36 | (2006.01) |
| A61N 1/372 | (2006.01) |

(52) U.S. Cl.
CPC ....... *A61N 1/0531* (2013.01); *A61N 1/36128* (2013.01); *A61N 1/37235* (2013.01); *A61N 1/37514* (2017.08)

(56) References Cited

U.S. PATENT DOCUMENTS

| | | | |
|---|---|---|---|
| 5,895,416 A | 4/1999 | Barreras, Sr. et al. | |
| 6,178,353 B1 | 1/2001 | Griffith et al. | |
| 6,246,911 B1 | 6/2001 | Seligman | |
| 6,463,328 B1 | 10/2002 | John | |
| 6,782,292 B2 | 8/2004 | Whitehurst | |
| 6,909,917 B2 | 6/2005 | Woods et al. | |
| 7,120,486 B2 | 10/2006 | Leuthardt et al. | |
| 7,177,678 B1 | 2/2007 | Osorio et al. | |
| 7,346,391 B1 | 3/2008 | Osorio et al. | |
| 7,353,065 B2 | 4/2008 | Morrell | |
| 7,532,935 B2 | 5/2009 | Maschino et al. | |
| 7,890,182 B2 | 2/2011 | Parramon et al. | |
| 8,065,012 B2 | 11/2011 | Firlik et al. | |
| 8,121,694 B2 | 2/2012 | Molnar et al. | |
| 8,262,714 B2 | 9/2012 | Hulvershorn et al. | |
| 8,380,314 B2 | 2/2013 | Panken et al. | |
| 8,396,557 B2 | 3/2013 | DiLorenzo | |
| 8,412,334 B2 | 4/2013 | Whitehurst et al. | |
| 8,868,173 B2 | 10/2014 | Nelson et al. | |
| 8,914,115 B2 | 12/2014 | Giftakis et al. | |
| 8,914,119 B2 | 12/2014 | Wu et al. | |
| 8,936,630 B2 | 1/2015 | Denison et al. | |
| 9,079,039 B2 | 7/2015 | Carlson et al. | |
| 9,084,901 B2 | 7/2015 | Wahlstrand | |
| 9,173,811 B2 | 11/2015 | Greiner et al. | |
| 9,198,828 B2 | 12/2015 | Greiner et al. | |
| 9,327,069 B2 | 5/2016 | Foster et al. | |
| 9,352,145 B2 | 5/2016 | Whitehurst et al. | |
| 9,381,346 B2 | 7/2016 | Lee et al. | |
| 9,409,030 B2 | 8/2016 | Perryman et al. | |
| 9,511,223 B2 | 12/2016 | DeGiorgio et al. | |
| 9,566,449 B2 | 2/2017 | Perryman et al. | |
| 9,597,494 B2 | 3/2017 | Wingeier et al. | |
| 9,782,593 B2 | 10/2017 | Parramon et al. | |
| 9,925,384 B2 | 3/2018 | Perryman et al. | |
| 9,949,376 B2 | 4/2018 | Greenberg et al. | |
| 10,025,375 B2 | 7/2018 | Lazor et al. | |
| 10,149,958 B1 | 12/2018 | Tran et al. | |
| 10,201,708 B2 | 2/2019 | De Ridder | |
| 10,220,211 B2 | 3/2019 | Liao | |
| 10,471,262 B2 | 11/2019 | Perryman et al. | |
| 11,467,665 B2 | 10/2022 | Gribctz | |
| 2002/0087201 A1 | 7/2002 | Firlik et al. | |
| 2006/0122660 A1 | 6/2006 | Boveja et al. | |
| 2007/0027499 A1 | 2/2007 | Maschino et al. | |
| 2007/0043401 A1 | 2/2007 | John | |
| 2007/0179558 A1 | 8/2007 | Gliner | |
| 2008/0161880 A1 | 7/2008 | Firlik et al. | |
| 2009/0112278 A1 | 4/2009 | Wingeier et al. | |
| 2009/0118804 A1 | 5/2009 | Moffitt et al. | |
| 2009/0264954 A1 | 10/2009 | Rise et al. | |
| 2010/0114237 A1 | 5/2010 | Giftakis et al. | |
| 2010/0280336 A1 | 11/2010 | Giftakis et al. | |
| 2011/0009922 A1 | 1/2011 | Assaf et al. | |
| 2011/0137381 A1 | 6/2011 | Lee et al. | |
| 2011/0264165 A1 | 10/2011 | Molnar et al. | |
| 2011/0295338 A1 | 12/2011 | Rickert et al. | |
| 2012/0071947 A1 | 3/2012 | Gupta et al. | |
| 2012/0108998 A1 | 5/2012 | Molnar et al. | |
| 2012/0296444 A1 | 11/2012 | Greenberg et al. | |
| 2013/0178829 A1 | 7/2013 | Rezai et al. | |
| 2014/0058528 A1 | 2/2014 | Contreras-Vidal et al. | |
| 2014/0142669 A1 | 5/2014 | Cook et al. | |
| 2014/0200432 A1 | 7/2014 | Banerji et al. | |
| 2014/0214125 A1 | 7/2014 | Greiner et al. | |
| 2014/0237073 A1 | 8/2014 | Schiff | |
| 2014/0277019 A1 | 8/2014 | Pearson | |
| 2015/0105837 A1 | 4/2015 | Aguilar Domingo | |
| 2015/0118661 A1 | 4/2015 | Haruta | |
| 2015/0119689 A1 | 4/2015 | Pascual-Leone et al. | |
| 2015/0227702 A1 | 8/2015 | Krishna | |
| 2016/0206883 A1 | 7/2016 | Bornzin et al. | |
| 2016/0331968 A1* | 11/2016 | Greenberg | ............... A61B 5/24 |
| 2016/0354095 A1 | 12/2016 | Pearson | |
| 2017/0042474 A1 | 2/2017 | Widge et al. | |
| 2017/0043167 A1 | 2/2017 | Widge et al. | |
| 2017/0202475 A1 | 7/2017 | Leuthardt | |
| 2017/0259064 A1 | 9/2017 | Wu et al. | |
| 2018/0036537 A1 | 2/2018 | Van den Heuvel | |
| 2018/0133487 A1* | 5/2018 | Shah | ................ A61N 1/3754 |
| 2018/0153474 A1 | 6/2018 | Aeschlimann et al. | |
| 2018/0289311 A1 | 10/2018 | Phillips | |
| 2018/0353759 A1 | 12/2018 | Starr et al. | |
| 2019/0090749 A1 | 3/2019 | Leuthardt et al. | |
| 2019/0216342 A1 | 7/2019 | Williams et al. | |
| 2019/0217112 A1 | 7/2019 | Williams et al. | |
| 2019/0217113 A1 | 7/2019 | Williams et al. | |
| 2019/0217116 A1 | 7/2019 | Williams et al. | |
| 2019/0346925 A1 | 11/2019 | Daniels | |
| 2020/0023189 A1 | 1/2020 | Gribetz et al. | |
| 2020/0330749 A1 | 10/2020 | Gribetz et al. | |
| 2021/0255707 A1 | 8/2021 | Gribetz | |
| 2021/0361948 A1 | 11/2021 | Leuthardt et al. | |
| 2022/0413612 A1 | 12/2022 | Gribctz | |
| 2023/0075205 A1 | 3/2023 | Moran | |

FOREIGN PATENT DOCUMENTS

| | | | |
|---|---|---|---|
| EP | 2835988 | 2/2015 | |
| EP | 2038004 | 1/2018 | |
| JP | 2009-524450 | 7/2009 | |
| JP | 2013-527784 | 7/2013 | |
| JP | 2014-079387 | 5/2014 | |
| JP | 2016-517283 | 6/2018 | |
| WO | WO 2005/039696 | 5/2005 | |
| WO | WO 2006/029007 | 3/2006 | |
| WO | WO 2007/138598 | 12/2007 | |
| WO | WO 2009/044271 | 4/2009 | |
| WO | WO 2009/067323 | 5/2009 | |
| WO | WO 2010/056751 | 5/2010 | |
| WO | WO 2011/123150 | 10/2011 | |
| WO | WO 2014/078074 | 5/2014 | |
| WO | WO 2014/130960 | 8/2014 | |
| WO | WO 2015/164477 | 10/2015 | |
| WO | WO 2015/195553 | 12/2015 | |
| WO | WO 2016/049789 | 4/2016 | |
| WO | WO 2016/118811 | 7/2016 | |
| WO | WO 2017/199052 | 11/2017 | |
| WO | WO-2018072894 A1 * | 4/2018 | ............... A61B 5/24 |
| WO | WO 2018/109715 | 6/2018 | |
| WO | WO 2019/130248 | 7/2019 | |
| WO | WO 2019/239367 | 12/2019 | |
| WO | WO 2019/244099 | 12/2019 | |
| WO | WO 2020/161555 | 8/2020 | |

(56) References Cited

FOREIGN PATENT DOCUMENTS

| WO | WO-2020225797 A1 * | 11/2020 |
| WO | WO 2021/144730 | 7/2021 |

OTHER PUBLICATIONS

Examination Report Under Sections 12 & 13 of the Patents Act, 1970 and the Patents Rules, 2003 Dated Aug. 12, 2021 From the Government of India, Intellectual Property India, Patents, Designs, Trade Marks, Geographical Indications, the Patent Office Re. Application No. 201927028238. (6 Pages).
International Preliminary Report on Patentability Dated Jul. 9, 2020 From the International Bureau of WIPO Re. Application No. PCT/IB2018/060667. (8 Pages).
International Preliminary Report on Patentability Dated Dec. 24, 2020 From the International Bureau of WIPO Re. Application No. PCT/IB2019/054948. (8 Pages).
International Preliminary Report on Patentability Dated Jun. 27, 2019 From the International Bureau of WIPO Re. Application No. PCT/IB2017/057952. (9 Pages).
International Preliminary Report on Patentability Dated Apr. 30, 2021 From the International Preliminary Examining Authority Re. Application No. PCT/IB2020/050527. (45 Pages) (Part 1).
International Preliminary Report on Patentability Dated Apr. 30, 2021 From the International Preliminary Examining Authority Re. Application No. PCT/IB2020/050527. (45 Pages) (Part 2).
International Preliminary Report on Patentability Dated Dec. 30, 2020 From the International Bureau of WIPO Re. Application No. PCT/IB2019/055217. (9 Pages).
International Search Report and the Written Opinion Dated Apr. 10, 2019 From the International Searching Authority Re. Application No. PCT/IB2018/060667. (14 Pages).
International Search Report and the Written Opinion Dated Dec. 13, 2019 From the International Searching Authority Re. Application No. PCT/IB2019/055217. (15 Pages).
International Search Report and the Written Opinion Dated Apr. 16, 2020 From the International Searching Authority Re. Application No. PCT/IB2020/050527. (16 Pages).
International Search Report and the Written Opinion Dated Oct. 16, 2019 From the International Searching Authority Re. Application No. PCT/IB2019/054948. (13 Pages).
International Search Report and the Written Opinion Dated Mar. 22, 2018 From the International Searching Authority Re. Application No. PCT/IB2017/057952. (16 Pages).
International Search Report and the Written Opinion Dated Jun. 23, 2021 From the International Searching Authority Re. Application No. PCT/IB2021/050253. (21 Pages).
Invitation to Pay Additional Fees Dated Oct. 15, 2019 From the International Searching Authority Re. Application No. PCT/IB2019/055217. (2 Pages).
Invitation to Pay Additional Fees, Communication Relating to the Results of the Partial International Search and the Provisional Opinion Dated May 3, 2021 From the International Searching Authority Re. Application No. PCT/IB2021/050253. (10 Pages).
Written Opinion Dated Dec. 21, 2020 From the International Preliminary Examining Authority Re. Application No. PCT/IB2020/050527. (9 Pages).
Albert et al. "Deep Brain Stimulation, Vagal Nerve Stimulation and Transcranial Stimulation: An Overview of stimulation Parameters and Neurotransmitter Release", Neuroscience & Biobehavioral Reviews,33(7):1042-1060, Jul. 2009.
Alesci et al. "Major Depression Is Associated with Significant Diurnal Elevations in Plasma Interleukin-6 Levels, a Shift of Its Circadian Rhythm, and Loss of Physiological Complexity in Its Secretion: Clinical Implications", The Journal of Clinical Endocrinology & Metabolism, 90(5): 2522-2530, May 1, 2005.
Allain et al. "Enzymatic Determination of Total Serum Cholesterol", Clinical Chemistry,20(4): 470-475, Apr. 1974.
American Psychiatric Association "Diagnostic and Statistical Manual of Mental Disorders: DSM-IV™", The American Psychiatric Association, Fourth Ed., p. 1-886, May 1994.
Asselbergs et al. "Mobile Phone-Based Unobtrusive Ecological Momentary Assessment of Day-to-Day Mood: An Explorative Study", Journal of Medical Internet Research,18(3):1-15, 2016.
Avery et al. "A Controlled Study of Repetitive Transcranial Magnetic Stimulation in Medication-Resistant Major Depression", Biological Psychiatry,59(2):187-194, Jan. 15, 2006.
Ballenger et al. "Carbamazepine in Manic-Depressive Illness: A New Treatment", The American Journal of Psychiatry, 137(7): 782-790, Jul. 1980.
Barker et al. "Non-Invasive Magnetic Stimulation of Human Moto Cortex", The Lancet 325:1106-1107, 1985.
Behrend et al. "Toward Feedback Controlled Deep Brain Stimulation: Dynamics of Glutamate Release in the Subthalamic Nucleus in Rats", Journal of Neuroscience Methods, 180(2): 278-289, Jun. 15, 2009.
Bejjani et al. "Transient Acute Depression Induced by High-Frequency Deep-Brain Stimulation", The New England Journal of Medicine, 340:1476-1480,May 13, 1999.
Belmaker et al. "Major Depressive Disorder", The New England Journal of Medicine, 358:55-68,Jan. 3, 2008.
Benabid et al. "Combined (Thalamotomy and Stimulation) Stereotactic Surgery of the VIM Thalamic Nucleus for Bilateral Parkinson Disease",Proceedings of the Meeting of the American Society for Stereotactic and Functional Neurosurgery, Applied Neurophysiology, 50: 344-346, 1987.
Ben-Menachem et al. "Effects of Vagus Nerve Stimulation on Amino Acids and Other Metabolites in the CSF of Patients with Partial Seizures", Epilepsy Research, 20(3):221-227, Mar. 1995.
Ben-Menachem et al. "Vagus Nerve Stimulation for Treatment of Partial Seizures: 1. A Controlled Study of Effect on Seizures", Epilepsia, 35(3):614-626, 1994.
Berndt et al. "Expanding the Optogenetics Toolkit: A Naturally Occurring Channel for Inhibitory Optogenetics is Discovered", Science, 349(6248): 590-591,Aug. 7, 2015.
Bhagwagar et al. "Persistent Reduction in Brain Serotonin1A Receptor Binding in Recovered Depressed Men Measured by Positron Emission Tomography with [11C]WAY-100635", Molecular Psychiatry, 9:386-392, Mar. 24, 2004.
Bichot et al. "A Source for Feature-Based Attention in the Prefrontal Cortex", Neuron 88(4): 832-844, Nov. 18, 2015.
Bick et al. "Neuromodulation for Restoring Memory", Neurosurgical Focus, 40:1-12, May 2016.
Biederman et al. "A Fully-Integrated, Miniaturized (0.125 mm$^2$) 10.5 μW Wireless Neural Sensor", IEEE Journal of Solid-State Circuits, 48(4): 960-970, Apr. 2013.
Boyden et al. "Millisecond-Timescale, Genetically Targeted Optical Control of Neural Activity", Nature Neuroscience, 8(9):1263-1268, Sep. 2005.
Bradley et al. "Influence of Child Abuse on Adult Depression Moderation by the Corticotropin-Releasing Hormone Receptor Gene",Arch Gen Psychiatry.65(2):190-200,Feb. 2008.
Brody et al. "Regional Brain Metabolic Changes in Patients With Major Depression Treated With Either Paroxetine or Interpersonal Therapy", Arch Gen Psychiatry.;58(7):631-640, Jul. 2001.
Bundy et al. "Decoding Three-Dimensional Reaching Movements Using Electrocorticographic Signals in Humans", Journal of Neural Engineering, 13(2):1-18, Feb. 23, 2016.
Burke et al. "Depression and Cortisol Responses toPpsychological Stress: A Meta-Analysis", Psychoneuroendocrinology 30(9): 846-856, Oct. 2005.
Butson et al. "Current Steering to Control the Volume of Tissue Activated During Deep Brain Stimulation", Brain Stimulation, 1(1): 7-15, Jan. 2008.
Carpenter et al. "Effect of Vagus Nerve Stimulation on Cerebrospinal Fluid Monoamine Metabolites, Norepinephrine, and Gamma-AminobutyricAacid Concentrations in Depressed Patients", Biological Psychiatry, 56(6): 418-426, Sep. 15, 2004.
Carroll et al. "Pathophysiology o fHypercortisolism in Depression", Acta Psychiatrica Scandinavica 115 (Suppl. 433): 90-103, Feb. 2007.

(56) References Cited

OTHER PUBLICATIONS

Caspi et al. "Influence of Life Stress on Depression: Moderation by a Polymorphism in the 5-HTT Gene", Science, 301(5631): 386-389, Jul. 18, 2003.
Cepoiu et al. "Recognition of Depression by Non-Psychiatric Physicians—A Systematic Literature Review and Meta-Analysis", Journal of General Internal Medicine,23(1):25-36, Jan. 2008.
Cohen et al. "Developing a More Focal Magnetic Stimulator. Part I: Some Basic Principles", Journal of Clinical Neurophysiology, 8(1):102-111, Jan. 1, 1991.
Collinger et al. "High-Performance Neuroprosthetic Control by an Individual with Tetraplegia", The Lancet, 381(9866): 557-564, Feb. 16-22, 2013.
Coppen "The Biochemistry of Affective Disorders", The British Journa of Psychiatry,113(504):1237-1264, Nov. 1967.
Coyne et al. "Prevalence, Depressive Nature, and Comorbidity of Disorders in Primary Care", General Hospital Psychiatry, 16: 267-276, 1994.
Cronin et al. "Task-Specific Somatosensory Feedback via Cortical Stimulation in Humans", IEEE Transactions on Haptics, 9(4):512-522, Jul. 18, 2016.
Dantzer et al. "From Inflammation to Sickness and Depression: When the Immune System Subjugates the Brain", Nature Reviews Neuroscience, 9:46-56, Jan. 1, 2008.
Davidson et al. "Depression: Perspectives from Affective Neuroscience", Annual Review of Psychology, 53:545-574, Feb. 2002.
Deisseroth "Optogenetics: 10 years of Microbial Opsins in Neuroscience", Nature Neuroscience, 18(9): 1213-1225, Sep. 2015.
Deisseroth et al. "Optogenetics", Nature Methods, 8(1):26-29, Jan. 2011.
Depression Guideline Panel "Depression in Primary Care: Detection, Diagnosis, and Treatment", Journal of American Association of Nurse Practionars, 6(5): 224-238, May 1994.
Dimitriu et al. "Neurostimulatory Therapeutics in Management of Treatment-Resistant Depression with Focus on Deep Brain Stimulation", Mount Sinai Journal of Medicine, 75(3):263-275, Jun. 2008.
Dobelle "Artificial Vision for the Blind by Connecting a Television Camera to the Visual Cortex", ASAIO Journal, 46(1):3-9, Jan.-Feb. 2000.
Dobelle et al. "Artificial Vision for the Blind by Electrical Stimulation of the Visual Cortex", Neurosurgery, 5(4):521-527, Oct. 1, 1979.
Dobelle et al. "Artificial Vision for the Blind: Electrical Stimulation of Visual Cortex Offers Hope for a Functional Prosthesis", Science, 1834123):440-444, Feb. 1, 1974.
Dobelle et al. "'Braille' Reading by a Blind Volunteer by Visual Cortex Stimulation", Nature, 259:111-112, Jan. 15, 1976.
Dobelle et al. "Phosphenes Produced by Electrical Stimulation of Human Occipital Cortex, and Their Application to the Development of a Prosthesis for the Blind", The Journal of Physiology, 243(2):553-576, Dec. 1, 1974.
Doud et al. "Continuous Three-Dimensional Control of a Virtual Helicopter Using a Motor Imagery Based Brain-Computer Interface", PLOS One,6(10):1-10, Oct. 26, 2011.
Dougherty et al. "A Randomized Sham-Controlled Trial of Deep Brain Stimulation of the Ventral Capsule/Ventral Striatum for Chronic Treatment-Resistant Depression", Biological Psychiatry, 78(4):240-248, Aug. 15, 2015.
Duman et al. "A Molecular and Cellular Theory of Depression", Arch Gen Psychiatry,54(7):597-606, 1997.
Duman et al. "A Neurotrophic Model for Stress-Related Mood Disorders", Biological Psychiatry, 59(12):1116-1127, Jun. 15, 2006.
Duman et al. "Neuronal Plasticity and Survival in Mood Disorders", Biological Psychiatry, 48(8): 732-739,Oct. 15, 2000.
Dumm et al. "Virtual Electrodes by Current Steering in Retinal Protheses", Investigational Ophthalmology & Visual Science, 55(12): 8077-8085, Dec. 2014.
Ellis et al. "Is Platelet Imipramine Binding Reduced in Depression? A Meta-Analysis", Biological Psychiatry, 36(5):292-299, Sep. 1, 1994.
Emiliani et al. "All-Optical Interrogation of Neural Circuits", Journal of Neuroscience 35(41):13917-13926, Oct. 14, 2015.
Fava "Diagnosis and Definition of Treatment-Resistant Depression", Biological Psychiatry, 53(8):649-659, Apr. 15, 2003.
Feng et al. "Toward Closed-ILop Optimization of Deep Brain Sstmulation for Parkinson's Disease: Concepts and Lessons from a Computational Model", Journal of Neural Engineering, 4(2):14-21, Feb. 23, 2007.
Figiel et al. "The Use of Rapid-Rate Transcranial Magnetic Stimulation (FTMS) in Refractory Depressed Patients", Journal of Neuropsychiatry, 10(1):20-25, Apr. 2006.
Fitzgerald et al. "A Randomized, Controlled Trial of Sequential Bilateral Repetitive Transcranial Magnetic Stimulation for Treatment-Resistant Depression", The American Journal of Psychiatry, 163(1):88-94,Jan. 2006.
Fitzgerald et al. "The Application of Transcranial Magnetic Stimulation in Psychiatry and Neurosciences Research", Acta Psichiatrica Scandinavica, 105(5( ):324-340, May 2002.
Fontaine et al. "Effect of Subthalamic Nucleus Stimulation on Obsessive-Compulsive Disorder in a Patient with Parkinson Disease," Journal of Neurosurgery 100 (2004):1084-1086.
Foster et al. "Reverse Replay of Behavioural Sequences in Hippocampal Place Cells During the Awake State.", Nature,440: 680-683, Mar. 30, 2006.
Frank et al. "Hold Your Horses: Impulsivity, Deep Brain Stimulation, and Medication in Parkinsonism", Science,318(23):1309-1312, Nov. 2007.
Fu et al. "Stable Long-Term Chronic Brain Mapping at the Single-Neuron Level", Nature Methods,13: 875-882, Aug. 29, 2016.
Gale et al. "Electrical Stimulation-Evoked Dopamine Release in the Primate Striatum", Stereotact Functional Neurosurgery,91(6):355-363, Nov. 2013.
Gale et al. "Reward and Reinforcement Activity in the Nucleus Accumbens During Learning", Frontiers in Behavioral Bioscience, 8, Art. 114: 1-10, Apr. 2014.
Garrett et al. "EVestG(TM): Responses in Depressed Patients," 30th Annual International IEEE EMBS Conference Vancouver, British Columbia, Canada, Aug. 20-24, 2008, pp. 1707-1710.
George et al. "A One-Year Comparison of Vagus Nerve Stimulation with Treatment as Usual for Treatment-Resistant Depression", Biological Psychiatry, 58(5):364-373,Sep. 1, 2005.
George et al. "Vagus Nerve Stimulation: A New Tool for Brain Research and Therapy", Biological Psychiatry, 47(4):287-295,Feb. 15, 2000.
Goldapple et al. "Modulation of Cortical-Limbic Pathways in Major Depression: Treatment-Specific Effects of Cognitive Behavior Therapy", Arch Gen Psychiatry,61(1):34-41, 2004.
Golier et al. "Low Serum Cholesterol Level and Attempted Suicide", The American Journal of Psychiatry, 152(3):419-423, Apr. 2006.
Goodman et al. "Deep Brain Stimulation in Psychiatry: Concentrating on the Road Ahead", Biological Psychiatry, 65(4):263-266,Feb. 15, 2009.
Greenberg et al. "Three-Year Outcomes in Deep Brain Stimulation for Highly Resistant Obsessive-Compulsive Disorder", Neuropsychopharmacology, 31:2384-2393, Jul. 19, 2006.
Grossman et al. "Noninvasive Deep Brain Stimulation via Temporally Interfering Electric Fields", Cell,169(6): 1029-1041, Jun. 1, 2017.
Hacker et al. "Frequency-Specific Electrophysiologic Correlates of Resting State fMRI Networks", NeuroImage, 149: 446-457, Apr. 1, 2017.
Hacker et al. "Resting State Network Estimation in Individual Subjects", NeuroImage, 82: 616-633, Available Online Jun. 2, 2013.
Haelbig et al. "Pallidal Stimulation in Dystonia: Effects on Cognition, Mood, and Quality of Life", Journal of Neurology, Neurosurgery and Psychiatry,76(12):1713-1716, 2005.
Hamilton etal. "Neural Signal Processing and Closed-Loop Control Algorithm Design for an Implanted Neural Recording and Stimu-

(56) References Cited

OTHER PUBLICATIONS lation System", 37th Annual International Conference of the IEEE Engineering in Medicine and Biology Society (EMBC), 7831-7836, Aug. 2015.

Han et al. "Microelectrode Technologies for Deep Brain Stimulation", Implantable Neural Proteses, 1. Devices and Applications, p. 195-219, Jun. 10, 2009.

Hardesty et al. "Deep Brain Stimulation in Movement and Psychiatric Disorders", Biological Psychiatry, 61(7):831-835, Apr. 1, 2007.

Heils et al. "Allelic Variation of Human Serotonin Transporter Gene Expression", Journal of Neurochemistry, 66(6):2621-2624, Jun. 1996.

Henry et al. "Brain Blood Flow Alterations Induced by Therapeutic Vagus Nerve Stimulation in Partial Epilepsy: I. Acute Effects at High and Low Levels of Stimulation", Epilepsia, 39(9):983-990, Sep. 1998.

Hochberg et al. "Neuronal Ensemble Control of Prosthetic Devices by a Human with Tetraplegia", Nature, 442:164-171, Jul. 13, 2006.

Holsboer "The Corticosteroid Receptor Hypothesis of Depression", Neuropsychopharmacology, 23:477-501, Nov. 1, 2000.

Holsboer et al. "Antidepressants and Hypothalamic-Pituitary-Adrenocortical Regulation", Endocrine Reviews, 17(2):187-205, Apr. 1, 1996.

Hong et al. "Syringe Injectable Electronics: Precise Targeted Delivery with Quantitative Input/Output Connectivity", Nano Letters, 15 (10): 6979-6984, 2015.

Jacobs et al. "Adult Brain Neurogenesis and Psychiatry: A Novel Theory of Depression", Molecular Psychiatry,5:262-269, Jun. 15, 2000.

Janicak et al. "Transcranial Magnetic Stimulation in the Treatment of Major Depressive Disorder: A Comprehensive Summary of Safety Experience From Acute Exposure, Extended Exposure, and During Reintroduction Treatment", Journal of Clinical Psychiatry, 69(222-232), Feb. 2008.

Jarosiewicz et al. "Virtual Typing by People with Tetraplegia Using a Self-Calibrating Intracortical Braincomputer Interface", Science Translational Medicine 11;7(313):28P. Nov. 2015.

Jiminez et al. "A Patient with a Resistant Major Depression Disorder Treated with Deep Brain Stimulation in the Inferior Thalamic Peduncle", Neurosurgery, 57(3):585-593, Sep. 1, 2005.

Judd et al. "A Prospective 12-Year Study of Subsyndromal and Syndromal Depressive Symptoms in Unipolar Major Depressive Disorders", Arch Gen Psychiatry,55(8):694-700, Aug. 1998.

Karege et al. "Decreased Serum Brain-Derived Neurotrophic Factor Levels in Major Depressed Patients", Psychiatry Research, 109(2):143-148, Mar. 15, 2002.

Katnani et al. Temporally Coordinated Deep Brain Stimulation in the Dorsal and Ventral Striatum Synergistically Enhances Associative Learning, Scientific Reports, 6:1-8, Jan. 4, 2016.

Kearns et al. "A Comparison of Depression Rating Scales", The British Journal of Psychiatry, 141(1): 45-49, Jul. 1982.

Kempermann et al. "Depressed New Neurons?—Adult Hippocampal Neurogenesis and a Cellular Plasticity Hypothesis of Major Depression", Biological Psychiatry, 54(5):499-503, Sep. 1, 2003.

Kendler et al. "The Interaction of Stressful Life Events and a Serotonin Transporter Polymorphism in the Prediction of Episodes of Major Depression", Arch Gen Psychiatry, 62(5):529-535, May 2005.

Kennedy et al. "Direct Control of a Computer from the Human Central Nervous System", IEEE Transactions on Rehabilitation Engineering, 8(2): 198-202, Jun. 2000.

Kessler et al. "Lifetime Prevalence and Age-of-Onset Distributions of DSM-IV Disorders in the National Comorbidity Survey Replication", Archives of General Psychiatry, 62(6): 593-602, Jun. 2005.

Kessler et al. "The Epidemiology of Major Depressive Disorder: Results From the National Comorbidity Survey Replication (NCS-R)", JAMA, 289(23):3095-3105, Jun. 18, 2003.

Kirsch et al. "Initial Severity and Antidepressant Benefits: A Meta-Analysis of Data Submitted to the Food and Drug Administration", PLOS Medicine, 5(2):260-268, Feb. 2008.

Kirsch et al. "The Emperor's New Drugs: An Analysis of Antidepressant Medication Data Submitted to the U.S. Food and Drug Administration", Prevention & Treatment,5, (Art.23):1-11, Jul. 15, 2002.

Klein et al. Therapeutic Efficacy of Right Prefrontal Slow Repetitive Transcranial Magnetic Stimulation in Major Depression, A Double-Blind Controlled Study: Arch Gen Psychiatry. 56(4):315-320, 1999.

Klomp et al. "Fabrication of Large Arrays of Cortical Electrodes for Use in Man", Journal of Biomedical Materials Research Banner, 11(3):347-364, May 1977.

Konsman et al. "Rat brain vascular distribution of interleukin-1 type-1 receptor immunoreactivity: relationship to patterns of inducible cyclooxygenase expression by peripheral inflammatory stimuli", The Journal of Comparitive Neurology, 472(1):113-129, Apr. 19, 2004.

Kosel et al. "Mood Improvement After Deep Brain Stimulation of the Internal Globus Pallidus for Tardive Dyskinesia in a Patient Suffering From Major Depression", Journal of Psychiatric Research, 41(9):801-803, Nov. 2007.

Krahl et al. "Locus Coeruleus Lesions Suppress the Seizure-Attenuating Effects of Vagus Nerve Stimulation", Epilepsia, 39(7):709-714 Jul. 1998.

Kroenke et al. "The PHQ-9 Validity of a Brief Depression Severity Measure", Journal of General Internal Medicine Banner, 16(9): 606-613, Sep. 2001.

Kucewicz et al. "Evidence for Verbal Memory Enhancement with Electrical Brain Stimulation in the Lateral Temporal Cortex", Brain, a Journal of Neurology, 141(4); 971-978, Apr. 2018.

Kunugi et al. "Low Serum Cholesterol in Suicide Attempters", 41(2):196-200, Jan. 15, 1997.

Lacassse et al. "Serotonin and Depression: A Disconnect between the Advertisements and the Scientific Literature", PLOS Mdicine, 2(12):1211-1216, Dec. 2005.

Leuthardt et al. "A Brain-Computer Interface Using Electrocorticographic Signals in Humans", Journal of Neural Engineering 1(2): 63-71,Jun. 14, 2004.

Lewis et al. "Restoration of Vision in Blind Individuals Using Bionic Devices: A Review with a Focus on Cortical Visual Prostheses", Brain Research, 1595: 51-73, Jan. 21, 2015.

LiKamWa et al. "MoodScope: Building a Mood Sensor from Smartphone Usage Patterns", MobiSys '13 Proceeding of the 11th Annual International Conference on Mobile Systems, Applications, and Services: 389-402, Jun. 25-28, 2013.

Liu et al. "Syringe Injectable Electronics", Nature Nanotechnology, 10(7): 629-636,Jul. 2015.

Lozano et al. "Subcallosal Cingulate Gyrus Deep Brain Stimulation for Treatment-Resistant Depression", Biological Psychiatry, 64(6):461-467, Sep. 15, 2008.

Maier et al. "S100B, Homocysteine, Vitamin B12, Folic Acid, and Procalcitonin Serum Levels in Remitters to Electroconvulsive Therapy: A Pilot Study", Disease Markers, 2018(Art.ID 2358451): 1-8, Published Online Jan. 10, 2018.

Makris et al. Variability and Anatomical Specificity of the Orbitofrontothalamic Fibers of Passage in the Ventral Capsule/Ventral Striatum (VC/VS): Precision Care for Patient-specific Tractography-Guided Targeting of Deep Brain Stimulation (DBS) in Obsessive Compulsive Disorder (OCD), Brain Imaging and Behavior, 10(4):1054-1067, Dec. 2016.

Malone, Jr. et al. "Deep Brain Stimulation of the Ventral Capsule/Ventral Striatum for Treatment-Resistant Depression", Biological Psychiatry, 65(4):267-275, Feb. 15, 2009.

Manji et al. "The Cellular Neurobiology of Depression", Nature Medicine, 7:541-547, May 1, 2001.

Mann "The Medical Management of Depression", The New England Journal of Medicine, 353:1819-1834, Oct. 27, 2005.

Marangell et al. "Neurostimulation Therapies in Depression: A Review of New Modalities", Acta Psychiatrica Scandinavica, 116(3):174-181, Sep. 2007.

(56) References Cited

OTHER PUBLICATIONS

Marangell et al. "Vagus Nerve Stimulation (VNS) for Major Depressive Episodes: One Year Outcomes", Biological Psychiatry, 51(4):280-287, Feb. 15, 2002.
Martin et al. "Brain Blood Flow Changes in Depressed Patients Treated With Interpersonal Psychotherapy or Venlafaxine Hydrochloride", Arch Gen Psychiatry.;58(7):641-648, Jul. 2001.
Mayberg "Limbic-Cortical Dysregulation: A Proposed Model of Depression", Clinical Neurosciences, 9(3), 471-481, 1997.
Mayberg et al. "Deep Brain Stimulation for Treatment-Resistant Depression", Neuron, 45(5):651-660, Mar. 3, 2005.
Mayberg et al. "Reciprocal Limbic-Cortical Function and Negative Mood: Converging PET Findings in Depression and Normal Sadness", The American Journal of Psychiatry, 156(5):675-682, May 1, 1999.
Mayberg et al. "Regional Metabolic Effects of Fluoxetine in Major Depression: Serial Changes and Relationship to Clinical Response", Biological Psychiatry, 48(8):830-843,Oct. 15, 2000.
McCreery et al. "A Characterization of the Effects of Neuronal Excitability Due to Prolonged Microstimulation with Chronically Implanted Microelectrodes", IEEE Transactions on Biomedical Engineering, 44(10):931-939, Oct. 1997.
Merali et al. "Dysregulation in the Suicide Brain: mRNA Expression of Corticotropin-Releasing Hormone Receptors and GABAA Receptor Subunits in Frontal Cortical Brain Region", The Journal of Neuroscience, 24(6):1478-1485, Feb. 11, 2004.
Milak et al. "Neuroanatomic Correlates of Psychopathologic Components of Major Depressive Disorder", Arch Gen Psychiatry, 62(4):397-408, Apr. 2005.
Moessner et al. "Consensus Paper of the WFSBP Task Force on Biological Markers: Biological Markers in Depression", The World Journal of Biological Psychiatry, 8(3):141-174, 2007.
Moran et al. "Motor Cortical Representation of Speed and Direction During Reaching", Journal of Neurophysiology, 82(5): 2676-2692, Nov. 1, 1999.
Morikawa et al. "An Origami-Inspired Ultrastretchable Bioprobe Film Device", IEEE 29th International Conference on Micro Electro Mechanical Systems (MEMS):149-152, Jan. 2016.
Mueller et al. "Recurrence After Recovery From Major Depressive Disorder During 15 Years of Observational Follow-Up", The American Journal of Psychiatry, 156(7):1000-1006, Jul. 1999.
Muller et al. "Thin-Film, Ultra High-Density Microelectrocorticographic Decoding of Speech Sounds in Human Superior Temporal Gyrus", IEEE Engineering in Medicine and Biology Conference Orlanda,6P, Feb. 2016.
Naples et al. "A Spiral Nerve Cuff Electrode for Peripheral Nerve Stimulation", IEEE Transactions on Biomedical Engineering, 35(11): 905-916, Nov. 1988.
Nemeroff et al. "Elevated Concentrations of CSF Corticotropin-Releasing Factor-Like Immunoreactivity in Depressed Patients", Science, 226(4680):1342-1344, Dec. 14, 1984.
Nemeroff et al. "VNS Therapy in Treatment-Resistant Depression: Clinical Evidence and Putative Neurobiological Mechanisms", Neuropsychopharmacology, 31:1345-1355, Apr. 19, 2006.
Nestler et al. "Neurobiology of Depression", Neuron, 34(1):13-25, Mar. 28, 2002.
Neuronetics "NeuroStar TMS Therapy® System: FDA-Cleared Transcranial Magnetic Stimulation for Treatment of Depression", Neuronetics, 3 P., Sep. 2, 2011.
Nibuya et al. "Regulation of BDNF and trkB mRNA in Rat Brain by Chronic Electroconvulsive Seizure and Antidepressant Drug Treatments", Journal of Neuroscience, 15(11):7539-7547, Nov. 1, 1995.
Nuttin et al. "Electrical Stimulation in Anterior Limbs of Internal Capsules in Patients with Obsessive-Compulsive Disorder", Lancet, 354,(9189):1526, Oct. 30, 1999.
Nuyujukian et al. "A Nonhuman Primate Brain-Computer Typing Interface", Proceedings of the IEEE,105(1):66-72, Sep. 12, 2016.

O'Brien et al. "Plasma Cytokine Profiles in DSepressed Patients Who Fail to Respond to Selective Serotonin Reuptake Inhibitor Therapy", Journal of Psychiatric Research, 41(3-4):326-331, Apr.-Jun. 2007.
Ongur et al. "Prefrontal Cortical Projections to the Hypothalamus in Macaque Monkeys", The Journal of Comparative Neurology,401(4):480-505, Nov. 30, 1998.
Oxley et al. "Minimally Invasive Endovascular Stentelectrode Array for High-Fidelity, chronic Recordings of Cortical Neural Activity", Nature Biotechnology, 34: 320-327, Feb. 8, 2016.
Palopoli-Trojani et al. "In Vitro Assessment of Long-Term Reliability of Low-Cost [Mu]ECoG Arrays", 38th Annual International Conference of the IEEE Engineering in Medicine and Biology Society, EMBC, Orlando, FL, USA, Aug. 16-20, 2016, p. 4503-4506, Aug. 16, 2016.
Paniccia et al. "Clinical and Non-Clinical Depression and Anxiety in Young People: A Scoping Review on Heart Rate Variability", Autonomic Neuroscience: Basic and Clinical, 208: 1-14, Published Online Aug. 26, 2017.
Park et al. "Closed-Loop, Ultraprecise, Automated Craniotomies", Journal of Neurophysiology 113: 3943-3953, Jun. 2015.
Pascual-Marquis et al. "Low Resolution Electromagnetic Tomography: A New Method for Localizing Electrical Activity in the Brain", International Journal of Psychophysiology, 18(1):49-65, Oct. 1994.
Peretti et al. "Safety and Tolerability Considerations: Tricyclic Antidepressants vs. Selective Serotonin Reuptake Inhibitors",Acta Psychiatrica Scandinavica, 101(Suppl.403):17-25, Sep. 2000.
Petridis et al. "Unobtrusive Low Cost Pupil Size Measurements Using Web Cameras", 2nd International Workshop on Artificial Intelligence and Netmedicine (NetMed'13):9-20, Nov. 28, 2013.
Piallat et al. "Monophasic But Not Biphasic Pulses Induce Brain Tissue Damage During Monopolar High-Frequency Deep Brain Stimulation", Neurosurgery, 64(1):156-163, Jan. 1, 2009.
Pittenger et al. "Stress, Depression, and Neuroplasticity: A Convergence of Mechanisms", Neuropsychopharmacology, 33:88-109, 2008.
Pool et al. "Psychosurgery in Oler People", Journal of American Geriatrics Society (AGS), 2(7): 456-466, Jul. 1954.
Post et al, "Antidepressant effects of carbamazepine", Journal of Psychiatry, 143(1): 29-34, Jan. 1986.
Quitkin et al. "Study Duration in Antidepressant Research: Advantages of a 12-Week Trial", Journal of Psychiatric Research, 20(3):211-216,Jan. 1, 1986.
Raisman et al. "High-Affinity 3H-Imipramine Binding in Platelets From Untreated and Treated Depressed Patients Compared to Healthy Volunteers", Psychopharmacology, 75(4):368-371, Dec. 1981.
Raison et al. "Cytokines Sing the Blues: Inflammation and the Pathogenesis of Depression", 27(1):24-31, Jan. 2006.
Rechlin et al. "Are Affective Disorders Associated with Alterations of Heart Rate Variability?", Journal of Affective Disorders,32(4): 271-275, Dec. 1994.
Rubin et al. "Neuroendocrine Aspects of Primary Endogenous Depression", Arch Gen Psychiatry, 44(4):328-336, Apr. 1987.
Ruhe et al. "Mood Is Indirectly Related to Serotonin, Norepinephrine and Dopamine Levels in Humans: A Meta-Analysis of Monoamine Depletion Studies", Molecular Psychiatry, 12:331-359,Jan. 16, 2007.
Rush "About Treatment Resistant Depression", Cyberonics, 2007.
Rush et al. "Vagus Nerve Stimulation (VNS) for Treatment-Resistant Depressions: A Multicenter Study", Biological Psychiatry, 47(4):276-286, Feb. 15, 2000.
Russel "A Circumplex Model of Affect", Journal of Prsonality and Social Psychology, 39(6): 1161-1178, 1980.
Sapolsky "Glucocorticoids and Hippocampal Atrophy in Neuropsychiatric Disorders", Arch Gen Psychiatry. 57(10):925-935, Oct. 2000.
Schalk et al. "Brain-Computer Interfaces Using Electrocorticographic Signals", IEEE Reviews in Biomedical Engineering, 4:140-154, Oct. 17, 2011.
Scherer et al. "Self-Reported Symptoms of Depression and PTSD Are Associated with Reduced Vowel Space in Screening Interviews", IEEE Transactions on Affective Computing, 7(1): 59-61, Jan.-Mar. 2016.

(56) References Cited

OTHER PUBLICATIONS

Schwartz et al. "Primate Motor Cortex and Free Arm Movements to Visual Targets in Three-Dimensional Space. I. Relations Between Single Cell Discharge and Direction of Movement", The Journal of Neuroscience, 8(8): 2913-2927,Aug. 1, 1988.
Seo et al. "Wireless Recording in the Peripheral Nervous System with Ultrasonic Neural Dust", Neuron,91(3): 529-539, Aug. 3, 2016.
Sgoifo et al. "Autonomic Dysfunction and Heart Rate Variability in Depression", Stress, 18(3): 343-352, Published Online May 25, 2015.
Shimizu et al. "Alterations of Serum Levels of Brain-Derived Neurotrophic Factor (BDNF) in Depressed Patients With or Without Antidepressants", Biological Psychiatry, 54(1):70-75, Jul. 1, 2003.
Siddiqi et al. "Repetetive Transcranial Magnetic Stimulation With Resting-State Network Targeting for Treatment-Resistant Depression in Traumatic Brain Injury: A Randomized, Controlled, Double-Blinded Pilot Study", Journal of Neurotrauma, 36(8): 1361-1374, Published Online Jan. 7, 2019.
Silk et al. "Pupillary Reactivity to Emotional Information in Child and Adolescent Depression: Links to Clinical and Ecological Measures", The American Journal of Psychiatry, 164(12): 1873-1880, Dec. 2007.
Smith "The Macrophage Theory of Depression", Medical Hypotheses, 35(4):298-306, Aug. 1991.
Smith et al. "A Bayesian statistical analysis of behavioral facilitation associated with deep brain stimulation", Journal of Neuroscience Methods, 183(2):267-276,Oct. 15, 2009.
Solomon et al. "Multiple Recurrences of Major Depressive Disorder", The American Journal of Psychiatry, 157(2):229-233, Feb. 2000.
Speer et al. "Opposite effects of high and low frequency rTMS on regional brain activity in depressed patients", Biological Psychiatry, 48(12): 1133-1141,Dec. 15, 2000.
Sullivan et al. "Genetic Epidemiology of Major Depression: Review and Meta-Analysis", The American Journal of Psychiatry, 157(10):1552-1562, Oct. 2000.
Sun et al. "Responsive Cortical Stimulation for the Treatment of Epilepsy", Neurotherapeutics,5(1):68-74, Jan. 2008.
Taylor et al. "Direct Cortical Control of 3D Neuroprosthetic Devices", Science, 296, (5574):1829-1832, Jun. 7, 2002.
Troncoso et al. "Vision's First Steps: Anatomy, Physiology, and Perception in the Retina, Lateral Geniculate Nucleus, and Early Visual Cortical Areas", Visual Prosthetics: 23-57, Jan. 4, 2011.
Tung et al. "Using Finite State Automata to Produce Self-Optimization and Self-Control", IEEE Transactions on Parallel and Distributed Systems, 7(4):439-448, Apr. 1996.
Turner et al. "Selective Publication of Anti-Depressant Trials and its Influence on Apparent Efficacy", The New England Journal of Medicine, 358:252-260, Jan. 17, 2008.
Van Rijsbergen et al. "Can a One-Item Mood Scale Do the Trick? Predicting Relapse over 5.5-Years in Recurrent Depression", PLOS One, 7(10):1-5, Oct. 3, 2012.
Velasco et al. "Neurobiological Background for Performing Surgical Intervention in the Inferior Thalamic Peduncle for Treatment of Major Depression Disorders", Neurosurgery, 57(3):439-448,Sep. 1, 2005.
Viventi et al. "Flexible, Foldable, Actively Multiplexed, High-Density Electrode Array for Mapping Brain Activity In Vivo", Nature Neuroscience, 14(12): 1599-1605, 2011.
Wang et al. "An Electrocorticographic Brain Interface in an Individual with Tetraplegia", PLOS One 8(2):1-8, Feb. 6, 2013.
Watanabe et al. "Transcranial Electrical Stimulation Through Screw Electrodes for Intraoperative Monitoring of Motor Evoked Potentials", Journal of Neurosurgery 100(1):155-160, Jan. 1, 2004.
Wells et al. "The Functioning and Well-Being of Depressed Patients: Results From the Medical Outcomes Study", JAMA, 262(7):914-919, Aug. 18, 1989.
Wheeler et al. "An Implantable 64-Channel Neural Interface With Reconfigurable Recording and Stimulation", 37th Annual International Conference of the IEEE Engineering in Medicine and Biology Society (EMBC), 7837-7840, Aug. 2015.
Wodlinger et al. "Ten-Dimensional Anthropomorphic Arm Control in a Human Brain-Machine Interface: Difficulties, Solutions, and Limitations", Journal of Neural Engineering, 12(1):1-17, Dec. 16, 2014.
Wong et al. "Closed-Loop Control of Cellular Functions Using Combinatory Drugs Guided by a Stochastic Search Algorithm", Proceedings of the National Academy of Sciences, 105(13): 5105-5110, Apr. 1, 2008.
Xie et al. "Three-Dimensional Macroporous Nanoelectronic Networks as Minimally Invasive Brain Probes", Nature Materials, 14: 286-1292 Oct. 5, 2015.
Yamagiwa et al. "Flexible Parylene-Film Optical Waveguide Arrays", Applied Physics LKetters, 107(8), 6P, 2015.
Yamagiwa et al. "Self-Curling and -Sticking Flexible Substrate for ECOG Electrode Array", IEEE 26th International Conference on Micro Electro Mechanical Systems (MEMS): 480-483, Jan. 2013.
Yanagisawa et al. "Electrocorticographic Control of a Prosthetic Arm in Paralyzed Patients", Annals of Neurology,71(3): 353-361, Mar. 2012.
Yirmiya et al. "Illness, Cytokines, and Depression", Annals of the New York Academy of Sciences, 917(1):478-487, Jan. 2000.
Yousry et al. "Localization of the Motor Hand Area to a Knob on the Precentral Gyrus, a New Landmark", Brain, 120(1): 141-157, Jan. 1, 1997.
Zhou et al. "Pulvinar-Cortex Interactions in Vision and Attention", Neuron,89(1): 209-220, Jan. 6, 2016.
Official Action Dated Oct. 26, 2023 from the US Patent and Trademark Office Re. U.S. Appl. No. 17/253,176. (17 pages).
Translation Dated May 3, 2024 of Grounds of Reason of Rejection Dated Apr. 25, 2024 From the Korean Intellectual Property Office Re. Application No. 10-2021-7001558 (6 Pages).
Notice of Reason(s) for Rejection Dated Jun. 20, 2023 From the Japan Patent Office Re. Application No. 2020-570860 and Its Translation Into English. (8 Pages).
Restriction Official Action Dated Feb. 2, 2023 from the US Patent and Trademark Office Re. U.S. Appl. No. 17/253,176. (7 pages).
Final Official Action Dated Feb. 16, 2023 from the US Patent and Trademark Office Re. U.S. Appl. No. 16/469,165. (33 pages).
Official Action Dated May 23, 2024 from the US Patent and Trademark Office Re. U.S. Appl. No. 17/253,176. (14 pages).
Official Action Dated Jul. 7, 2023 from the US Patent and Trademark Office Re. U.S. Appl. No. 17/253,176. (83 pages).
Communication Pursuant to Article 94(3) EPC Dated Nov. 7, 2023 From the European Patent Office Re. Application No. 19820226.9 (7 Pages).
Supplementary European Search Report and the European Search Opinion Dated Feb. 16, 2022 From the European Patent Office Re. Application No. 19820226.9. (8 Pages).
Grounds of Reason of Rejection Dated Apr. 25, 2024 From the Korean Intellectual Property Office Re. Application No. 10-2021-7001558 (7 Pages).
Requisition by the Examiner Dated Apr. 24, 2024 From the Innovation, Science and Economic Development Canada, Canadian Intellectual Property Office Re. Application No. 3,103,772 and Claims. (8 Pages).
Notice of Reason(s) for Rejection Dated Nov. 2, 2021 From the Japan Patent Office Re. Application No. 2019-533071 and Its Translation Into English. (9 Pages).
Notification of Office Action and Search Report Dated Sep. 9, 2022 From the China National Intellectual Property Administration Re. Application No. 201780085562.2. (8 Pages).
Restriction Official Action Dated Sep. 18, 2024 from the US Patent and Trademark Office Re. U.S. Appl. No. 17/792,149. (6 pages).
Requisition by the Examiner Dated Aug. 10, 2023 From the Innovation, Science and Economic Development Canada, Canadian Intellectual Property Office Re. Application No. 3,103,772. (4 Pages).
International Preliminary Report on Patentability Dated Jul. 28, 2022 From the International Bureau of WIPO Re. Application No. PCT/IB2021/050253. (13 Pages).

(56) References Cited

OTHER PUBLICATIONS

Official Action Dated Feb. 3, 2023 from the US Patent and Trademark Office Re. U.S. Appl. No. 17/895,124. (33 pages).
Official Action Dated Jul. 8, 2022 from US Patent and Trademark Office Re. U.S. Appl. No. 16/954,554. (69 pages).
Notice of Allowance Dated Jun. 1, 2022 from US Patent and Trademark Office Re. U.S. Appl. No. 17/251,829. (45 pages).
Examination Report Dated Feb. 28, 2024 From the Australian Government, IP Australia Re. Application No. 2019291582. (5 Pages).
Grounds of Reason of Rejection Dated May 26, 2022 From the Korean Intellectual Property Office Re. Application No. 2010-7029927. (3 Pages).
Official Action Dated Jun. 8, 2022 from US Patent and Trademark Office Re. U.S. Appl. No. 16/469,165. (78 pages).
Examination Report Dated Dec. 11, 2024 From the Australian Government, IP Australia Re. Application No. 2019291582. (3 Pages).

\* cited by examiner

INTRACALVARIAL BCI SYSTEMS AND METHODS FOR THEIR MAKING, IMPLANTATION AND USE

RELATED APPLICATIONSUS APPLICATION

This application is a National Phase of PCT Patent Application No. PCT/IB2020/050527 having International filing date of Jan. 23, 2020, which claims the benefit of priority under 35 USC § 119(e) of U.S. Provisional Patent Application No. 62/802,245 filed on Feb. 7, 2019. The contents of the above applications are all incorporated by reference as if fully set forth herein in their entirety.

FIELD AND BACKGROUND OF THE INVENTION

The present invention, in some embodiments thereof, relates to the field of brain computer interface systems (BCIs), and more particularly to Intracalvarial BCIs including electrodes and electrode arrays for implantation within the calvarial bone of a skull for recording electrical activity from brain tissues underlying the calvarial bone and/or for electrically stimulating brain tissues underlying the calvarial bone.

Recording of electrical signals from the cortical surface of the brain and electrically stimulating selected cortical regions as well as other deeper brain regions underlying the cortex may enable neuro-modulation of brain electrophysiology that may have a wide range of clinical and non-clinical applications. In some clinical applications, cortical stimulation may be used to modify cortical excitability to treat numerous neuropsychiatric diseases such as, among others, depression, ADHD, OCD, addiction, and obesity.

The recording of cortical electrical signals may also be implemented in brain computer interfaces that may be used to treat a wide array of motor disabilities.

Brain recording and/or stimulating methods may also be used for modulating the brain physiology to enhance cognitive function in healthy individuals or to improve cognitive function in some patients having neuropsychiatric diseases affecting cognitive performance such as, inter alia, depression, ADHD, OCD, Various eating disorders, epilepsy, and many other psychiatric, neurodegenerative, neurological and neuropsychiatric disorders.

Depending on the stimulation modality, the brain region being stimulated, and the interface regime, cognitive operations such as attention, memory, analytic abilities, and mood may all be enhanced beyond a given individual's normal baseline.

Several types of brain recording/stimulation are currently known. The least invasive recording method is EEG. In this method, recording electrodes are applied externally to the skull of the patient without penetrating the skin of the scalp.

While EEG has the advantage of being a non-invasive low risk recording method, it has several problems resulting from the substantial distance of the recording electrodes from the source of the electrical signals in the cortex and from the intervening skin and bone tissues. Such problems may include a relatively low signal to noise ratio (SNR) due to the low signal amplitude (typically in the range of 10-100 µV) and substantial attenuation of the higher frequency range part of the cortical signal by the intervening bone and skin tissues disposed between the recording EEG electrodes and the cortical surface, resulting. As a result of this frequency attenuation, the part of the cortical electrical activity in the gamma frequency band (f≥30 Hz) may be severely attenuated or completely lost below the noise floor in such EEG recordings, often resulting in loss of physiologically relevant information.

Other disadvantages of EEG recording methods and devices include the need for good electrical contact between the surface of the scalp and the EEG electrodes. The electrically conducting gels or preparations used to achieve and maintain such electrical contact are often messy to apply, may cause patient discomfort, are difficult to hold and maintain in the same position, and may change their resistance or impedance due to drying or loss of water content during extended periods of use that may result in degrading or altering their performance. Additionally, EEG electrode assemblies may not be suitable for long term ambulatory or permanent use because they are cumbersome, are very visible on the patient's head (which may result in the patient's reluctance to use them for long term extended periods of time).

Calvarial screws have been used for either sensing/recording electrical brain signals or for performing transcranial electrical stimulation (TES). For example, Watanabe et al. describe using two calvarial screws for performing TES in an article entitled "Transcranial electrical stimulation through screw electrodes for intraoperative monitoring of motor evoked potentials" published in J. Neurosurg 100: pp 155-160 (2004). Similarly, screw electrodes have been used for sensing electrical brain activity in animals. However, in all these cases, the upper part of the screw protrudes through the upper table of the skull bone in order to allow connecting a lead to the upper part for performing the sensing or the stimulation. The part of the screw protruding out of the skull bone may operate as an antenna and may disadvantageously pick up extraneous electrical noise which may decrease the SNR. Thus, the use of such calvarial screws, while adequate for experimental use in animals or for short term intraoperative use in neurosurgery patients, may not be suitable for long term use in ambulatory patients due to the possibility of noise pickup in changing environmental conditions which the patient may be exposed to. Moreover, long term use of calvarial screws may be objected to by patients due to aesthetic reasons and the need to be connected to stimulating and/or sensing leads which may be cumbersome.

Recently, a new method for non-invasive trans-cranial stimulation of brain tissues was disclosed in a paper by Nir Grossman, David Bono, Nina Deric, Suhasa B. Kodandaramalah, Andrii Rudenko, Ho-Jun Suk, Antonino M. Cassara, Esra Neufeld, Niels, Li Huei Tsai, Alvaro Pascual-Leone and Edwards S. Boyden, "Non-Invasive Deep Brain Stimulation via Temporally Interfering Electric Fields", Cell 169, pp. 1029-1041, Jun. 1, 2017.

This non-invasive method enables stimulation of selected brain regions using extra-cranial electrodes similar to sensing EEG electrodes to apply oscillating electric fields at two slightly different frequencies to the brain, resulting in an electric field envelope that oscillates at the beat frequency of the two different frequencies. The two different frequencies are at a relatively high frequency range (typically above 1 KHz) so each frequency by itself cannot cause neuronal stimulation by themselves. This method allows the non-invasive stimulation of deep brain structures by generating a defined region of electrical fields that oscillates at the beat frequency enabling neuronal recruitment within a selected location by electrical stimulation of neurons and/or neuronal parts within the recruitment region. The method of Grossman et al., is referred to hereinafter as trans-cranial frequency interference stimulation (TFIS) or as frequency interference (FI) stimulation.

However, TFIS may share some of the problems of using EEG sensing methods because it uses stimulating electrodes similar to EEG electrodes that are applied to the surface of the skull for stimulation. Such common problems may include, electrode instability, electrical coupling to the scalp necessitating electrically conductive gels or formulations, the sensitivity of scalp electrodes to accidental dislodgement or movement and/or to changes in electrical electrode impedance due to changes in the hydration state of such electrically conductive gels or formulations. Such problems may make the use of EEG type scalp electrodes undesirable for long term use such as in ambulatory patients.

Another, more invasive method for performing cortical surface recording uses epidural or subdural surface electrodes (typically, electrode arrays) which are placed on the surface of the dura mater (epidural Ecog) or on the cortical surface (subdural Ecog) to record an Electrocorticogram (Ecog) signal. Typically, the amplitude of the sense/recorded Ecog signals is about 10-20 mV. Such methods have the advantage of resulting in better signal to noise ratio (SNR) and enabling a higher frequency range of sensing due to their close proximity to the cortical surface. While intracranial Ecog arrays solve many of the problems of EEG recording techniques, a fundamental barrier for more wide spread adoption of such intra-cranially implanted Ecog electrode arrays is the invasiveness of the implantation of the electrodes. Once the skull and dura mater are penetrated with either intra-parenchymal or electrocorticographic electrodes there is a risk of having an intracranial hemorrhage or infection that could cause major harm, morbidity, or even death. While these risks, generally speaking, are very small the fact they exist substantially changes a patient's perception of considering adoption. This also changes the manner in which patients are treated by physicians after implantation. If an intracranial electrode implant is surgically placed (e.g. deep brain stimulator, cortical stimulator, etc.), at the very least the patients are kept overnight for observation in a hospital to ensure that, should an intracranial complication arise, it can be rapidly addressed. This increases the cost of such intracranial implantation procedures and may limit their use for many applications. There is therefore a long felt need for a recording and/or stimulating brain interface that has no or little risk of intracranial complications, may be more esthetic and have a lesser implantation impact yet still be able to record and/or stimulate the brain with a functional equivalence that is close to that of intracranial Ecog devices.

Published International application WO 2019/130248, incorporated herein by reference in its entirety, discloses intra-calvarial implants (ICIs) implantable in a skull for performing sensing/recording of cortical regions and/or for performing stimulation of regions of the brain. However, the ICIs disclosed in WO 2019/130248 do not include the current directing mechanisms of the ICIs disclosed herein

SUMMARY OF THE INVENTION

There is therefore provided, in accordance with some embodiments of the present application, an intra-calvarial implant (ICI) for implantation in a calvarial bone of a mammal. The calvarial bone has an outer table, a cancellous bone, and an outer table. The ICI includes a housing including a sealed compartment having a top part, a bottom part and a side wall extending between the top part and the bottom part and a current directing mechanism extending from the bottom part of the sealed compartment. ICT also includes one or more electrodes for sensing electrical signals from a cortex of a mammal and/or for electrically stimulating one or more regions of a brain of the mammal. The ICI also includes one or more auxiliary electrodes operable as a current return electrode or as a reference electrode or as a current return electrode and a reference electrode. The ICI also includes an electronic circuitry module (ECM) sealingly disposed within the sealed compartment and operatively electrically connected to the one or more electrodes and to the one or more auxiliary electrodes. The ECM is configured for controlling the operation of the ICI and for wirelessly communicating with an external telemetry device. The ICI also includes a power harvesting device suitably electrically connected to the ECM of the ICI for providing power thereto.

In some embodiments of the ICI, the current directing mechanism is selected from a current directing mechanism that is an integral part of the housing, and a current directing mechanism attached to the bottom part of the sealed compartment.

In some embodiments of the ICI, the sealed compartment is selected from a cylindrical sealed compartment having a bottom part having a bottom part diameter, and a frusto-conical shaped sealed compartment having a bottom part with a bottom part diameter and a top part with a top part diameter wherein the top part diameter is larger than the bottom part diameter.

In some embodiments of the ICI, the current directing mechanism includes a cylindrically shaped wall having a height H. The cylindrically shaped wall has a first end attached to or extending from the bottom part of the sealed compartment and a second end having a circularly shaped opening with a radius R.

In some embodiments of the ICI, $H \geq 0.5R$.

In some embodiments of the ICI, the current directing mechanism includes a non-cylindrical wall.

In some embodiments of the ICI, the cross-sectional shape of the non-cylindrical wall is selected from, an oval shape, an elliptical shape, a polygonal shape, an irregular shape and a cross-like shape.

In some embodiments of the ICI, the one or more electrodes are selected from, one or more electrodes attached to an internal surface of the wall of the current directing mechanism, and one or more electrodes disposed adjacent to the internal surface of the wall of the current directing mechanism.

In some embodiments of the ICI, the one or more auxiliary electrodes are selected from: at least one auxiliary electrode attached to the bottom part of the sealed compartment, at least one auxiliary electrode attached to the bottom part of the sealed compartment, at least one auxiliary electrode attached to the side wall of the sealed compartment, and any non-mutually exclusive combination thereof.

In some embodiments of the ICI, the one or more electrodes are implanted between an outer table and an inner table of the calvarial bone without fully penetrating the inner table.

In some embodiments of the ICI, at least one of the one or more auxiliary electrodes is/are disposed in a location selected from, between the outer table and the inner table of the calvarial bone, adjacent to at least part of the outer table of the calvarial bone, within the cancellous bone of the calvarial bone, on top of the housing of the ICI, and any non-mutually exclusive combinations thereof.

In some embodiments of the ICI, the one or more auxiliary electrodes are selected from, a reference electrode and a current return electrode separated from the reference electrode and electrically isolated therefrom, a reference electrode and a separate current return electrode, wherein the reference electrode is electrically connected to the current return electrode, and at least one electrode operating as a current return electrode when the ICI is used for stimulating and as a reference electrode when the ICI is used for sensing.

In some embodiments of the ICI, the cylindrically shaped wall has a diameter selected from, the diameter of the cylindrically shaped wall is smaller than the bottom part diameter of the sealed compartment, and the diameter of the cylindrically shaped wall is equal to the bottom part diameter of the sealed compartment.

In some embodiments of the ICI, the ICI includes one or more ground electrodes selected from, a ground electrode attached on top part of the sealed compartment, a ground electrode attached to the side walls of the sealed compartment, and a combination of a ground electrode attached on top of the sealed compartment and a ground electrode attached to the side walls of the sealed compartment.

In some embodiments of the ICI, the current directing mechanism includes: a first cylindrically shaped electrically non-conducting wall having a first end attached to or extending from the bottom part of the sealed compartment and a second end having a circularly shaped opening and, the first wall has a first outer diameter, and a second cylindrically shaped electrically non-conducting wall concentric with the first wall, the second wall has a first end attached to or extending from the bottom part of the sealed compartment and a second end having a circularly shaped opening, the second wall has a second outer diameter, wherein the second outer diameter is smaller than the first outer diameter.

In some embodiments of the ICI, the first wall has a first wall height H1 and the second wall has a second wall height H2, and wherein H1 and H2 are selected from H1=H2,
H1>H2, and
H1<H2.

In some embodiments of the ICI, the first wall has an inner surface having a radius R1 and the second wall has an inner surface having a radius R2, and wherein H1≥0.5R1 and H2≥0.5R2.

In some embodiments of the ICI, the one or more electrodes are selected from: one or more electrodes disposed between the first wall and the second wall, one or more electrodes attached to the first wall, one or more electrodes attached to the second wall, and at least one electrode attached to the first wall and at least one electrode attached to the second wall.

In some embodiments of the ICI, the outer diameter of the first current directing member is selected from: the outer diameter of the first current directing member is equal to the bottom part diameter of the sealed compartment, and the outer diameter of the first current directing member is smaller than the bottom part diameter of the sealed compartment.

In some embodiments of the ICI, the current directing mechanism includes a plurality of concentric cylindrical walls, and the one or more electrodes are disposed between the plurality of walls and/or on an inner surface of the innermost wall of the plurality of walls.

In some embodiments of the ICI, after implantation of the ICI, the one or more electrodes are substantially perpendicular to the inner table of the calvarial bone.

In some embodiments of the ICI, after implantation of the ICI, at least one electrode of the one or more auxiliary electrodes is substantially parallel to the inner table of the calvarial bone.

In some embodiments of the ICI, at least some electrodes of the one or more electrodes and the one or more auxiliary electrodes are made from or comprise a material selected from the group consisting of, platinum, a platinum/iridium alloy and graphene.

In some embodiments of the ICI, the power harvesting device includes an induction coil electrically connectable to a current conditioning circuit. The current conditioning circuit is selected from a current conditioning circuit formed as an integral part of the ECM and a current conditioning circuit separate from and electrically connected to the ECM.

In some embodiments of the ICI, power harvesting device also includes an electrical charge storage device electrically coupled to the current conditioning circuit and to the ECM.

In some embodiments of the ICI, the ICI also includes a shimming member attachable to an outer table of the calvarial bone over the top part of the sealed compartment.

In some embodiments of the ICI, the shimming member includes two or more tabs having holes therein for inserting screws into the holes to attach the shimming member claim.

In some embodiments of the ICI, the shimming member also includes a magnet.

In some embodiments of the ICI, the induction coil is selected from: an induction coil disposed within the sealed compartment, an induction coil integrated into the ECM, an induction coil disposed outside the sealed compartment, and an induction coil disposed on or within a shimming member included in the ICI.

In some embodiments of the ICI, the ICI is a stimulating ICI and wherein the ECM is an ECM programmed for controlling the stimulation of the brain using the one or more electrodes and for wirelessly receiving stimulation control signal from an external telemetry device or from another ICI in wireless communication with the stimulating ICT.

In some embodiments of the ICI, the ICI is a sensing/recording ICI and wherein the ECM is selected from:

1) An ECM programmed for controlling the sensing and/or recording of electrical signals from the brain using the one or more electrodes and the at least one reference electrode and for wirelessly transmitting signals recorded from the brain to the external telemetry device or to another ICI in wireless communication with the sensing/recording ICI. 2) An ECM programmed for controlling the sensing and/or recording of electrical signals from the brain using the one or more electrodes and the at least one reference electrode, for at least partially processing recorded signals to obtain data and for wirelessly transmitting the data to the external telemetry device, or to another ICI in wireless communication with the sensing/recording ICI. 3) An ECM programmed for controlling the sensing and/or recording of electrical signals from the brain using the one or more electrodes and the at least one reference electrode, for digitizing the recorded signals and for processing digitized signals to detect an indication of a physiological and/or a neurological and/or a neuropsychiatric state of the mammal and for wirelessly transmitting the indication data and/or stimulation control signals to the external telemetry device or to another ICI in communication with the sensing/recording ICI.

In some embodiments of the ICI, the ICI is a sensing/recording and stimulating ICI and wherein the ECM is selected from: 1) An ECM programmed for controlling the sensing and/or recording of electrical signals from the brain using the one or more electrodes and the at least one reference electrode and for wirelessly transmitting signals recorded from the brain to the external telemetry device and/or to another ICI in wireless communication with the sensing/recording and stimulating ICI. 2) An ECM programmed for controlling the sensing and/or recording of electrical signals from the brain using the one or more electrodes and the at least one reference electrode, for at least partially processing recorded signals to obtain data and for wirelessly transmitting the data to the external telemetry device and/or to another ICI in wireless communication with the sensing/recording and stimulating ICI, 3) An ECM programmed for controlling the sensing and/or recording of electrical signals from the brain using the one or more electrodes and the at least one reference electrode, for digitizing the recorded signals and for processing digitized data to detect an indication of a physiological and/or a neurological and/or a neuropsychiatric state of the mammal and for wirelessly transmitting the indication data to an external telemetry device and/or to another ICI in communication with the sensing/recording ICI, and 4) an ECM programmed for controlling the sensing and/or recording of electrical signals from the brain using the one or more electrodes and the at least one reference electrode, for digitizing the recorded signals and for processing digitized data for detecting an indication of a physiological and/or a neurological and/or a neuropsychiatric state of the mammal, for autonomously stimulating the brain using the one or more electrodes responsive to the detecting of the indication, for wirelessly communicating with the external telemetry device and/or with another ICI in communication with the sensing/recording and stimulating ICI.

In some embodiments of the ICI, the current directing mechanism is a multi-channel current directing mechanism including a plurality of hollow channels.

In some embodiments of the ICI, each channel of the plurality of channels has one electrode of the one or more electrodes disposed therein.

In some embodiments of the ICI, the ICI is part of an ICI system including at least one more ICI implanted in the same calvarial bone.

In some embodiments of the ICI, the power harvesting device is selected from the list consisting of, an electromagnetic induction based power harvesting device and an ultrasonic energy based power harvesting device.

In some embodiments of the ICI, the current directing mechanism includes a single cylindrically shaped wall having a first end extending from the bottom part of the sealed compartment or attached to the bottom part of the sealed compartment and a second open end. The one or more electrodes is a stimulating electrode disposed within the current directing mechanism, and the one or more auxiliary electrodes is a current return electrode.

In some embodiments of the ICI, the stimulating electrode is a tubular stimulating electrode disposed within the cylindrically shaped wall or attached thereto.

In some embodiments of the ICI, the current return electrode is selected from: 1) A current return electrode disposed on the top part of the sealed compartment. 2) A current return electrode disposed on the bottom part of the sealed compartment, and 3) A current return electrode disposed on the side wall of the sealed compartment.

In some embodiments of the ICI, the ICI also includes at least one sensing electrode disposed on or attached to the second end of the cylindrically shaped wall and a reference electrode.

In some embodiments of the ICI, the reference electrode is selected from the following:

1) The current return electrode. 2) A reference electrode disposed on the top part of the sealed compartment. 3) A reference electrode disposed on the bottom part of the sealed compartment, and 4) A reference electrode disposed on the side wall of the sealed compartment.

In some embodiments of the ICI, the cylindrically shaped wall is configured to be disposed within a tubular shaped passage drilled into the calvarial bone without breaching an inner table of the calvarial bone and the bottom part of the sealed compartment is configured to be attached to an outer surface of an outer table of the calvarial bone.

In some embodiments of the ICI, when the ICI is implanted, the sealed compartment is disposed between the outer table of the calvarial bone and the scalp.

In some embodiments of the ICI, the mammal is a human.

There is also provided, in accordance with the ICI systems of the present application an ICI system including two or more ICIs according to claim 1 the two or more ICIs are implanted in the same calvarial bone of a mammal.

In some embodiments of the ICI system, the two or more ICIs are selected from, ICIs configured only for performing sensing/recording of electrical brain signals, ICIs configured for only performing electrical brain stimulating, ICIs configured for performing both sensing/recording of electrical brain signals and sensing/recording of electrical brain signals, and any combinations thereof.

In some embodiments of the ICI system, one or more ICIs of the ICI system are selected from: the following 1) A master ICI configured for wirelessly receiving sensed brain electrical signals from one or more ICIs of the ICI system, processing the signals to detect an indication of a physiological and/or neurological and/or neuropsychiatric state of the mammal, and for wirelessly controlling brain stimulating operation of one or more of the ICIs of the system. 2) A master ICI configured for wirelessly receiving sensed signals from one or more ICIs of the ICI system, for sensing brain electrical signals, for processing the received signals and the signals sensed by the master ICI to detect an indication of a physiological and/or neurological and/or neuropsychiatric state of the mammal, and for wirelessly controlling the stimulating operation of one or more of the ICIs of the system. 3) A master ICI configured for wirelessly receiving sensed signals from one or more ICIs of the ICI system, for sensing brain electrical signals, for stimulating the brain, for processing the received signals and the signals sensed by the master ICI to detect an indication of a physiological and/or neurological and/or neuropsychiatric state of the mammal, or wirelessly controlling the stimulating operation of one or more of the ICIs of the system and for synchronizing the stimulation performed by one or more ICIs with the stimulation performed by the master ICI. 4) A master ICI configured for wirelessly receiving sensed signals from one or more ICIs of the ICI system, for sensing brain electrical signals, for processing the received signals and the signals sensed by the master ICI to detect an indication of a physiological and/or neurological and/or neuropsychiatric state of the mammal and for wirelessly controlling the stimulating operation of one or more of the ICIs. 5) A slave ICI configured for performing sensing/recording of brain electrical signals and for wirelessly transmitting sensed signals to a master ICI implanted in the same calvarial bone. 6) A slave ICI configured for stimulating the brain of the mammal and for wirelessly receiving stimulation control signals from a master ICI implanted in the same calvarial bone. 7) A slave ICI configured for performing sensing/recording of brain electrical signals, for wirelessly transmitting sensed signals to a master ICI implanted in the same calvarial bone, for stimulating the brain of the mammal, and for wirelessly receiving stimulation control signals from the master ICI implanted in the same calvarial bone, and any non-mutually exclusive combinations thereof.

In some embodiments of the ICI system, one or more of the ICIs included in the ICI system are configured for wirelessly communicating with an external controller/processor for performing one or more of: transmitting sensed electrical brain signals to the external controller processor, and receiving stimulation control signals from the external controller/processor.

There is also provided in accordance with the methods of the present application, a method for implanting the ICI in the calvarial bone. The method comprising the steps of:

1) Forming an incision in the scalp to expose an outer surface of an outer table of the calvarial bone.

2) Forming a hollow passage within the outer table and within a cancellous bone of the calvarial bone without fully breaching an inner table of the calvarial bone.

3) Inserting the current directing mechanism of the ICI into the hollow passage until the bottom part of the sealed compartment is in contact with the outer surface of the calvarial bone. and 4) Attaching the sealed compartment to the outer surface of the outer table.

In some embodiments of the method, the method also includes the step of closing the incision in the scalp.

There is also provided a method for implanting the ICI in the calvarial bone, the method includes the steps of:

1) Forming an incision in the scalp to expose an outer surface of an outer table of the calvarial bone.

2) Forming a hollow passage within the outer table and within the cancellous bone without fully breaching an inner table of the calvarial bone.

3) Inserting the ICI into the hollow passage until the top part of the sealed compartment is disposed below the level of outer surface of the calvarial bone.

4) Inserting a shimming member into the hollow passage such that the shimming member is in contact with the top part of the sealed compartment.

5) attaching the shimming member to the outer surface of the outer table.

In some embodiments of the method, the method also includes the step of closing the incision in the scalp.

There is also provided, in accordance with the methods of the present application, a method of directing current into a cortex through the inner table of a calvarial bone. The method includes the steps of:

1) Implanting an ICI in the calvarial bone such that at least part of the inner table, the pia matter and the dura matter intervene between the cortex underlying the inner table of the calvarial bone and the current directing mechanism of the ICI.

2) passing a current between at least one electrode of the one or more electrodes and at least one of the one or more auxiliary electrodes.

In some embodiments of the method, the current is a cortical stimulating current or a cortical inhibiting current.

In some embodiments of the method, the at least one electrode of the one or more electrodes is at least one electrode operating as a cathode or at least one electrode operating as an anode.

In some embodiments of the method, the current is a pulsed current.

In some embodiments of the method, the current directing mechanism changes at least one parameter of the current passing through the cortex, as compared to the current passed into the cortex by a similarly configured ICI lacking the current directing mechanism.

Finally, in some embodiments of the method, the at least one parameter is selected from one or more of, the current's rise-time, the current's density within a given cortical tissue volume, and the spatial distribution pattern of the current flowing into the cortex.

BRIEF DESCRIPTION OF THE SEVERAL VIEWS OF THE DRAWINGS

Some embodiments of the invention are herein described, by way of example only, with reference to the accompanying drawings, in which like components are designated by like reference numerals. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION OF SPECIFIC EMBODIMENTS OF THE INVENTION

Abbreviations

Figure 1:
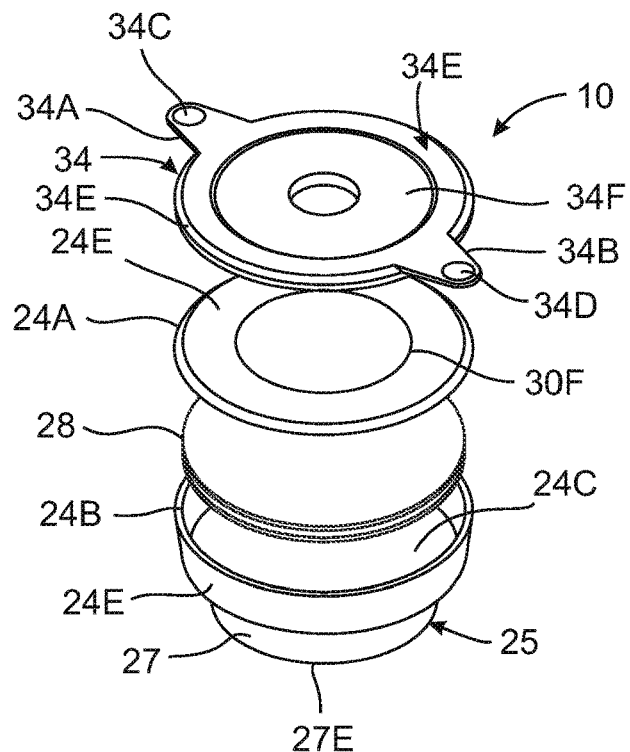
FIG. 1 is a schematic isometric exploded view of an intra-calvarial implant (ICI), in accordance with an embodiment of the ICIs of the present application.

The following abbreviations are used throughout the specification and the claims of the present application:

| Abbreviation | Means |
| --- | --- |
| μV | microvolt |
| CT | Computerized tomography |
| CVD | Chemical vapor deposition |
| cm | centimeter |
| DCES | Direct cortical electrical stimulation |
| ECM | Electronic circuitry module |
| Ecog | Electrocorticography |
| EEG | Electroencephalography |

-continued

| Abbreviation | Means |
| --- | --- |
| FI | Frequency interference |
| fMRI | Functional magnetic resonance imaging |
| ICE | Intra-calvarial Electrode |
| ICEA | Intra-calvarial electrode assembly |
| ICI | Intra-calvarial Implant |
| mm | Millimeter |
| MRI | Magnetic resonance imaging |
| mV | millivolt |
| SNR | Signal to Noise Ratio |
| TES | Trans-cranial electrical stimulation |
| TFIS | Trans-cranial frequency interference stimulation |
| TMS | Transcranial Magnetic Stimulation |

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways. It is expected that during the life of a patent maturing from this application many relevant types of electrodes and electrode arrays will be developed and the scope of the terms "electrode" and "electrode array" are intended to include all such new technologies a priori. As used herein the term "about" refers to ±10%. The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein, in embodiments in which the sealed compartment is disposed within the calvarial bone, the term "bottom part of the sealed compartment" refers to the part of the sealed compartment that faces the inner table of the calvarial bone after implantation. In embodiments in which the sealed compartment is disposed between the outer surface of the outer table of the calvarial bone and the scalp, the term "bottom part of the sealed compartment" refers to the part of the sealed compartment that faces the outer surface of the outer table of the calvarial bone after implantation.

Throughout the present application (including the claims), the term auxiliary electrode in its single and plural forms means either a current return electrode or a reference electrode, or both a current return electrode and a reference electrode.

A "current return electrode" is an electrode that may be operated to complete (close) an electrical circuit between the stimulating electrode and itself during the passing of a current between the two electrodes. It is noted that such a current "return" electrode may be operated as a cathode and/or as an anode, depending on the required effect (cortical activation or inhibition), Thus the direction of the current flowing during current passing may be from the stimulating electrode to the current return electrode or from the current return electrode to the stimulating electrode. Therefore, the current return electrode may serve as a current sink and/or as a current source depending on the electrode's polarity. The term auxiliary electrode may also mean a reference electrode for use in differential recording, where the electrical signal sensed by the reference electrode may be subtracted from the electrical signal sensed by a sensing electrode for common mode rejection.

In some embodiments, a single auxiliary electrode may be operated as a current return electrode during the passing of currents and as a reference electrode when sensing, by performing the passing of current at a different time than the time performing of sensing. An auxiliary electrode may also be grounded. In ICIs in which more than one auxiliary electrode is included, some (or one) auxiliary electrode(s) may be dedicated for use only as a reference electrode (for differential recording/sensing) while other auxiliary electrode(s) may be used as a dedicated current return electrode(s) during current passing.

Throughout this application and claims, the term "plurality" means "two or more".

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The present application discloses intra-calvarial electrodes, intra-calvarial electrode arrays and ICIs that are implanted within the calvarial bone of the skull of a mammal (such as, for example a human patient or other mammals). Also disclosed are methods of implanting such electrodes within the calvarial bone and methods for using the intra-calvarial electrode(s) for sensing cortical electrical activity using the intra-calvarial electrodes and methods of stimulating various different brain regions using intra-calvarial electrodes and electrode arrays, It is noted that the terms "calvarial bone", "calvarial bones" and "Calvaria" and their conjugate and plural forms are interchangeably used throughout the specification and the claims of the present application to include one or more of the following bones or parts of the following bones: the frontal bone, the left and right parietal bones, the occipital bone, the non-squamous parts of the left and right temporal bones, and the occipital bone. The terms "calvarial bone" and its plural and conjugate forms may also mean any combination of two or more calvarial bones or parts of bones selected from the above list and fused together. It is however noted that the term "calvarial bone" and its conjugate and plural forms, as used in the specification and the claims also includes any bone of the skull in which the ICIs of the present application may be implanted.

To achieve the least amount of invasiveness, while still enabling substantial stimulation and recording capabilities, the ICIs disclosed in the present application have electrodes that are implanted into the calvarial bone but do not fully penetrate the inner table of the calvarial bone. Important barriers that prevents infection and blood from affecting the brain are the dura mater and the inner table of the skull bones. If these barriers are not compromised, penetrated, or affected, then should there be some bleeding or infection related to the implant there would be no impact on the brain itself. This unique position of the electrodes also confers significant recording advantages. By implanting such electrodes or electrode arrays within the skull between the outer table and the inner table of the calvarial bone and close to the inner table of the calvarial bone (but without fully penetrating the inner table or passing through it) focal cortical signals may be readily detected since the electrodes may be approximately 2-3 millimeters from the cortical surface.

The electrical signals sensed and recorded in this way would be somewhat similar to electrocorticography (Ecog) in which electrodes are placed on the surface of the brain. Ecog signals have been shown to have substantial advantages in SNR in that they can detect focal cortical changes and record higher frequencies than typical EEG recording techniques (such as, for example, gamma rhythms). Numerous publications have shown the information value of Ecog signals for brain computer interfaces and for identifying highly resolved cortical dynamics related to cognition (motor, language, attention, memory, vision, etc.). The disclosed intra-calvarial electrode(s), ICIs and the systems including such electrodes and/or ICIs, are able to sense/record a similar level of signal quality without the risk of intracranial implantation risks. Thus, in addition to the benefits to the patient, the electrodes, ICIs, electrode arrays, and systems including them and the methods for their implantation and use would not require the patient to be admitted to a hospital for observation since the intracranial complication risks are absent. An outpatient procedure with risks more comparable to a tattoo would more likely be adopted by a larger clinical and non-clinical population.

Taken together, the ICIs and ICI systems using them enable high level access to neural interfacing without the attendant risks of an intracranial penetration, making the electrode(s), assemblies and systems suitable for more widespread application due to the reduced associated health risk combined with easy and cost effective implantation.

Beyond having distinct advantages over other more invasive technologies, the ICE approach has significant advantages over non-invasive approaches such as electroencephalography (EEG), trans-cranial magnetic stimulation (TMS), and direct cortical electrical stimulation (DCES). From a recording standpoint, EEG records cortical potentials that are summed over spans of several centimeters of the surface of the cortex. Thus, the anatomic specificity of EEG would be substantially less than an intra-calvarial electrode that would be recording signals summed from only several millimeters of the cortical surface. The proximity of ICE to the cortical surface would give substantially higher cortical resolution of local electrophysiological dynamics. From cortical stimulation standpoint, this proximity would have similar advantages over what is possible with TMS and DCES. With an ICE system, the close proximity to cortex in a fixed position would allow specific anatomic cortical stimulation. DCES stimulates wide regions of brain (about 5 cm) and thus cannot achieve specific cortical effects. TMS typically stimulates smaller regions but requires larger, cumbersome and quite expensive equipment that requires the patient to visit specialized centers offering access to this level of brain stimulation. An additional feature of the ICE system would be consistency of stimulation. Most cortical stimulation regimes require that a region of brain be stimulated repetitively over the course of days and weeks. As a result, TMS and DCES systems need to be attached to the same location relative to the patient's brain on a daily basis. Because ICI systems are implanted systems, stimulation would be almost identical each time, while TMS and DCES are much more variable. Finally, because multiple electrodes per implant may be implanted, stimulation could be further locally tailored to optimize the localized effect. This enhanced stimulation localization may be achieved by using direct cortical stimulation methods and selecting specific stimulating electrode(s) from the multiple electrodes of an electrode assembly or electrode array, or by using frequency interference methods using selected electrode pairs from the electrode array or electrode assembly for delivering the high frequency stimulating signals. This local adjustment flexibility is not possible with TMS of DCES.

Beyond the advantages of anatomic location of the ICE system, the circuitry of the system could also be configured or programmed to perform both recording and stimulation concurrently to synergize the advantages of both modalities. Closed loop cortical stimulation has been shown to substantially improve the intended functional and physiologic effect of stimulation. Using various physiologic biomarkers taken from cortex can better inform the amplitude, timing, and stimulation regime. Such markers include, time series measures (peak and trough of select frequency rhythms) frequency band amplitudes (e.g. delta, theta, mu, alpha, beta, and gamma), connectivity measures (correlation, mutual information, etc.), cross frequency interactions (e.g. phase amplitude coupling). All these signals could be used to optimize the timing and magnitude of stimulation. As an example, stimulation of memory-associated areas of brain (e.g. dorsal lateral prefrontal cortex) may better improve the subject's memory by timing the stimulation with specific phases of a theta rhythm (3-5 hz). Another example would be that the magnitude or amplitude of stimulation of motor cortex for the treatment of Parkinson patients could be titrated to minimize beta-gamma phase amplitude coupling.

In addition to optimizing the functional effect, this enhancement also may provide better efficiencies in power utilization. Optimal stimulation regimes would reduce the need for continual stimulation. Additionally, if functional effects are optimized for the given current density delivered, this may allow for a reduced amount of current required for a given effect (because the closer proximity of the electrodes to the brain region being stimulated). Both the optimized timing and stimulation dosage would require less power to deliver a given effect.

Furthermore, the ICIs of the present application may be constructed such as to have electrode configurations that may improve ICI performance by directing and/or confining the stimulating currents in such a way as to achieve efficient focal electrical stimulation of brain tissues underlying the ICI to conserve power as is disclosed in the ICI embodiments disclosed hereinafter.

Figure 2:
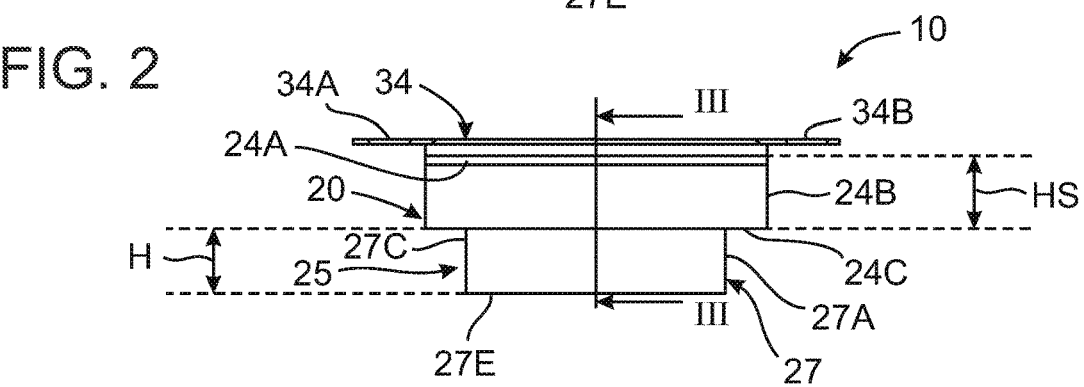
FIG. 2 is a schematic side view illustrating part of the ICI of FIG. 1.
Figure 3:
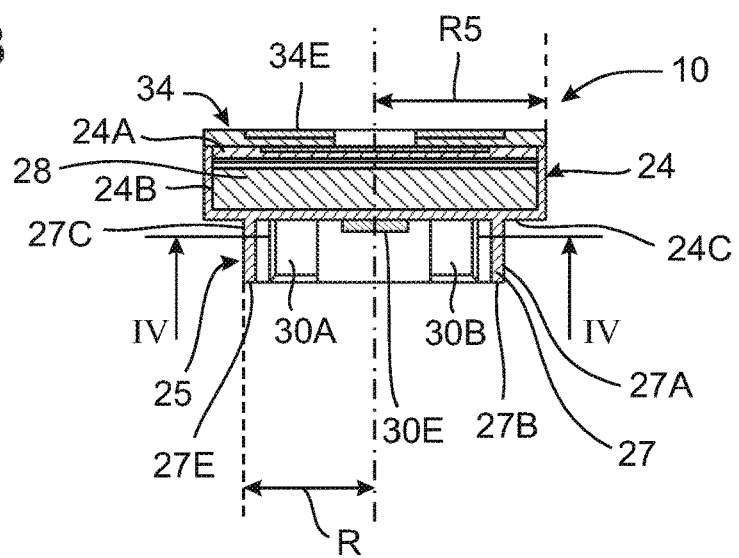
FIG. 3 is a schematic cross-sectional view of the ICI part of FIG. 2, taken along the lines III-III.
Figure 4:
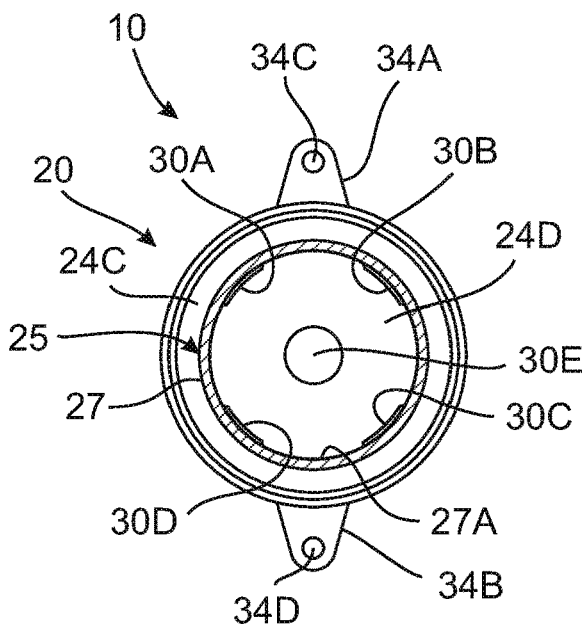
FIG. 4 is a schematic cross-sectional view of the ICI part of FIG. 3, taken along the lines IV-IV.
Figure 5:
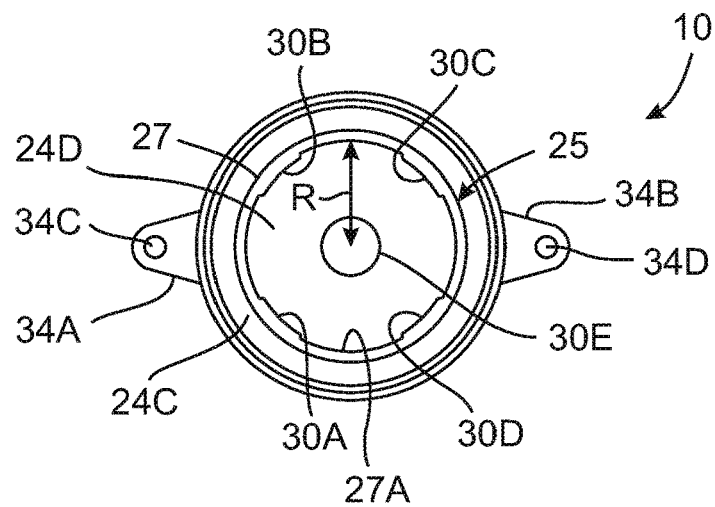
FIG. 5 is a schematic isometric view illustrating the ICI of FIG. 2.
Figure 6:
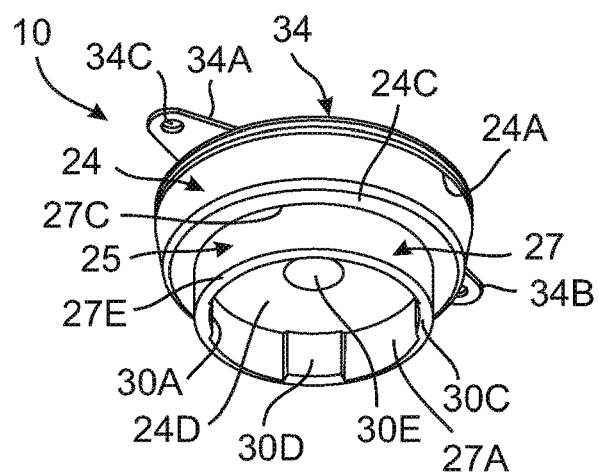
FIG. 6 is a schematic bottom view of the ICI of FIG. 2.
Figure 7:
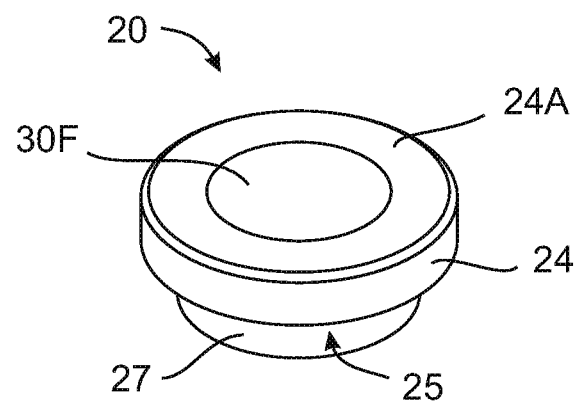
FIG. 7 is a schematic isometric view illustrating part of the ICI of FIG. 1 in a closed and sealed state.

Reference is now made to FIGS. 1-7. FIG. 1 is a schematic isometric exploded view of an intra-calvarial implant (ICI), in accordance with an embodiment of the ICIs of the present application. FIG. 2 is a schematic side view illustrating part of the ICI of FIG. 1. FIG. 3 is a schematic cross-sectional view of the ICI part of FIG. 2, taken along the lines III-III. FIG. 4 is a schematic cross-sectional view of the ICI part of FIG. 3, taken along the lines IV-IV. FIG. 5 is a schematic isometric view illustrating the ICI of FIG. 2. FIG. 6 is a schematic bottom view of the ICI of FIG. 2. FIG. 7 is a schematic isometric view illustrating part of the ICI of FIG. 1 in a closed and sealed state.

The ICI 10 may include a housing 20. The housing 20 may include a sealed compartment 24 and a current directing mechanism 25. The sealed compartment 24 may include a top part 24A, a bottom part 24C and side walls 24B extending between the top part 24A and the bottom part 24C.

The top part 24A of the sealed compartment 24 may be implemented as a circular lid that may be sealingly attached to or sealingly screwed into the side wall 24B to form the sealed compartment 24. The sealed compartment 24 when sealed by the top part 24A may have a height HS. The ICI 10 may also include an electronic circuitry module (ECM) 28.

After assembling of the ICI 10, the ECM 28 is sealingly enclosed within the sealed compartment 24. In accordance with some embodiments of the ICI 10, the housing 20 or parts thereof may be made from a suitable metal such as, for example titanium. In some embodiments, if the housing 20 or a part of the housing 20 is made from a metal, the housing 20 may be coated or covered with a thin layer of an electrically isolating (electrically non-conducting) biocompatible polymer, such as, for example, Parylene®, but other suitable polymers may also be used. In other embodiments the housing 20 or some parts thereof may be made from a biocompatible electrically non-conducting polymer based material such as, for example Parylene®, Kevlar®, polyetherketones (PEEK), Polyethylene (PE), polylactic acid (PLA), polyglycolic acid (PGA) copolymers of PLA and PGA, polysilanes or other suitable polymers. It is noted that while in some embodiments, the sealed compartment 24 and the current directing mechanism 25 may be made from the same material (such as, for example, Parylene® coated Titanium or a biocompatible polymer based material), in other embodiments, the sealed compartment 24 and the current directing mechanism may be made from different materials. For example, the side walls 24B and the bottom part 24C of the sealed compartment 24 may be made from titanium coated with Parylene®, the top part (case lid) 24A may be made from a ceramic material or PEEK and the current directing mechanism 25 may be made from a biocompatible polymer such as, for example PEEK, or PE.

In some embodiments of the ICIs, the sealed compartment 24 (or any other of the sealed compartments disclosed in the present application), may be made from an electrically conducting material (such as for example titanium). In some embodiments, parts of the sealed compartment may be coated or covered by a thin layer of electrically isolating biocompatible polymer, such as, for example, Parylene® in order to electrically isolate any of the electrodes from shorting through the metallic conducting material of the sealed compartment 24. However, in some such cases, the electrically conducting material (such as, titanium) may be independently grounded or held at ground potential. Such grounding may be particularly useful in ICIs during sensing because it may significantly increase the signal to noise ratio (SNR) during sensing and/or recording cortical signals and may prevent capacitive coupling from fluorescent lights as well as serve to shield some of the sensing electrodes and/or the ECM components from other sources of electromagnetic radiation in the environment by functioning similar to a faraday cage.

In such embodiments, the electrically conducting metal of the sealed compartment may be switchably and reversibly electrically connected to ground by the ECM 28) or by any of the ECM embodiments disclosed hereinafter. In such embodiments, the ECM (such as, for example, the ECM 28 may electrically connect the electrically conducting part of the sealed compartment 24 to the ground during sensing/recording and may disconnect the electrically conducting part of the sealed compartment 24 from the ground during stimulating.

Additionally, in some embodiments of the ICIs, only certain selected parts of the external surface of an electrically conducting sealed compartment may be coated with insulating polymer, while other parts may be left without coating. Such non-coated parts may serve as ground.

It some embodiments, the current directing mechanism 25 may be an integral part of the housing 20 and may be contiguous with the bottom part 24C of the sealed compartment 24. In other embodiments, the current directing mechanism 25 may be a separately made component that may be attached to the bottom part 24C of the sealed compartment during manufacturing of the ICI 10. The attaching of the current directing member 25 to the bottom part 24C may be performed by any suitable attachment method, such as, for example, gluing, welding, ultrasonic welding or by screwing a suitably threaded part of the current directing mechanism 25 into a suitably threaded recess (not shown in FIGS. 1-8 for the sake of clarity of illustration) formed in the bottom part 24C.

In accordance with some embodiments, the current directing mechanism 25 may be a cylindrically shaped wall 27 extending from the bottom part 24C of the sealed compartment 24 the wall has a first end 27C attached to or extending from the bottom part 24C of the sealed compartment 24 and a second end 27E having a circularly shaped opening 27C with a radius R. The height of the wall 27 is H.

The ICI 10 may also include four stimulating and recording electrodes 30A, 30B, 30C and 30D, a reference electrode 30E and a ground electrode 30F. It is noted that throughout the present application, the ground electrode 30F may also be referred to as the "return" electrode when used in a stimulating mode, as the current may leave the stimulating electrodes and return through the return electrode 30F. The electrodes 30A, 30B, 30C, 30D, 30E and 30F may be made of or may include a biocompatible electrically conducting material such as, for example platinum, a platinum/iridium alloy, graphene or any other suitable biocompatible electrically conducting material. Each of the electrodes 30A, 30B, 30C, 30D, 30E and 30F may be electrically connected to the ECM 28 by suitably electrically isolated electrical conducting members or electrode leads (which are not shown in FIGS. 1-7 for the sake of clarity of illustration), that may be, for example, electrically isolated electrically conducting wires. The wires may sealingly pass through suitable passages in the housing 20 (the passages are not shown in FIGS. 1-7 for the sake of clarity of illustration) the sealing of the passages prevents any moisture or bodily fluids from penetrating into the sealed compartment 24.

The stimulating/recording electrodes 30A, 30B, 30C and 30D may be attached to the inner surface 27A of the wall 27 of the current directing mechanism 25 as illustrated in FIGS. 4-5. The stimulating/recording electrodes 30A, 30B, 30C and 30D may be equally spaced along the surface 27A. The attachment of the electrodes 30A, 30B, 30C and 30D may be by gluing them to the surface 27A as illustrated in FIGS. 4-5. However, in some embodiments the electrodes 30A, 30B, 30C and 30D may be disposed in suitable recesses formed in the inner surface 24A of the wall 27.

In accordance with some embodiments, some or all of the electrodes 30A, 30B, 30C, 30D, 30E and 30F may also be deposited or coated on the appropriate surfaces of the housing 20 by methods such as, for example CVD, sputtering, ion beam deposition, spin coating or any other suitable method.

Alternatively, the electrodes 30A, 30B, 30C and 30D may be supported by the wall 27 while not being attached thereto. Such an arrangement may advantageously allow doubling the electrode surface area available for passing current, because the current may be passed from both sides of the electrodes 30A, 30B, 30C and 30D. In such an embodiment, the electrodes 30A, 30B, 30C and 30D may be mechanically stabilized by the wires electrically connecting them to the ECM 28 or by other suitable mechanical means (not shown).

The reference electrode 30E may be a circularly shaped electrode attached to the outer surface 24D of the bottom part 24C of the sealed compartment 24 by a suitable glue or by being partially embedded within a suitable recess (not shown) in the surface 24D. It is noted, that when the ICI 10 is implanted in the calvarial bone, the reference electrode 30E is more distant from the surface of the brain than the electrodes 30A, 30B, 30C and 30D. Therefore, when the ICI 10 is in a recording mode, the reference electrode may be used with each one of the electrodes 30A, 30B, 30C and 30D to perform differential recording of cortical electrical activity underlying each of the electrodes 30A, 30B, 30C and 30D.

It is noted that preferably (but not obligatorily) H≥0.5R. This increases the area of the inner surface 27A of the wall 27, and may enable using electrodes with a larger electrode surface area which in turn may lower electrode impedance resulting in advantageously lowering the compliance voltage of the electrodes.

The surface area of the electrodes of the ICIs of the present application may be in the range of 0.3-100 mm$^2$, depending, inter alia, on the structure and the dimensions of the current directing mechanism of the ICI, with typical values of the stimulating/recording electrodes in the range of about 1-2 mm$^2$, typical values of the reference electrodes in the range of about 4-8 mm$^2$ and typical values of ground (return) electrodes in the range of 50-100 mm$^2$. However, some of the electrodes may have surface area values lower than 0.3 mm$^2$ or higher than 100 mm$^2$, depending, inter alia on the particular medical application.

The ICI 10 may also include a ground electrode 30F. In some embodiments, the ground electrode 30F may be a circular electrode attached to the outer surface 24E of the top part 24A of the sealed compartment 24. The attachment of the ground electrode 30F to the top part 24A may be by any of the methods disclosed in detail hereinabove for the electrodes 30A, 30B, 30C, 30D and 30E. During stimulation, the ground electrode 30F may operate as a current source or current sink (depending on the polarity of stimulation current being used). It is noted that while the ground electrode of the ICI 10 may be attached to the top part 24A of the sealed compartment 24, this is not obligatory. Rather, in some embodiments of the ICIs of the present application, the ground electrode may be attached to the outer surface 24E of the side wall 24B of the sealed compartment 24. For example, the ground electrode may be a ring shaped electrode attached to the side walls 24B (for example, see FIG. 15 hereinafter). Furthermore, in some embodiments, the ICI may have more than one ground electrode (for example, see FIG. 15 hereinafter).

It will be appreciated that while the exemplary embodiment of the ICI 10 of FIGS. 1-7 has four stimulating/recording electrodes 30A, 30B, 30C and 30D, this is by no means obligatory and some embodiments of the ICIs of the present application may typically include a number of stimulating and/or recording electrodes in the range of 2-16 electrodes, and in certain embodiments the number of electrodes may be even greater than 16. The factors determining the number of recording and/or stimulating electrodes may include, inter alia, the type and dimensions of the ICI, the specific structure of the current directing mechanism, the degree of precision required during stimulation, the specific medical or clinical application, the intensity of the required stimulating currents, and other considerations.

In some embodiments, the reference electrode 30E may be used as a reference electrode in a recording mode but may be also used for stimulating during a stimulating mode of the ICI 10 (See for example, FIG. 16 hereinafter).

Figure 12:
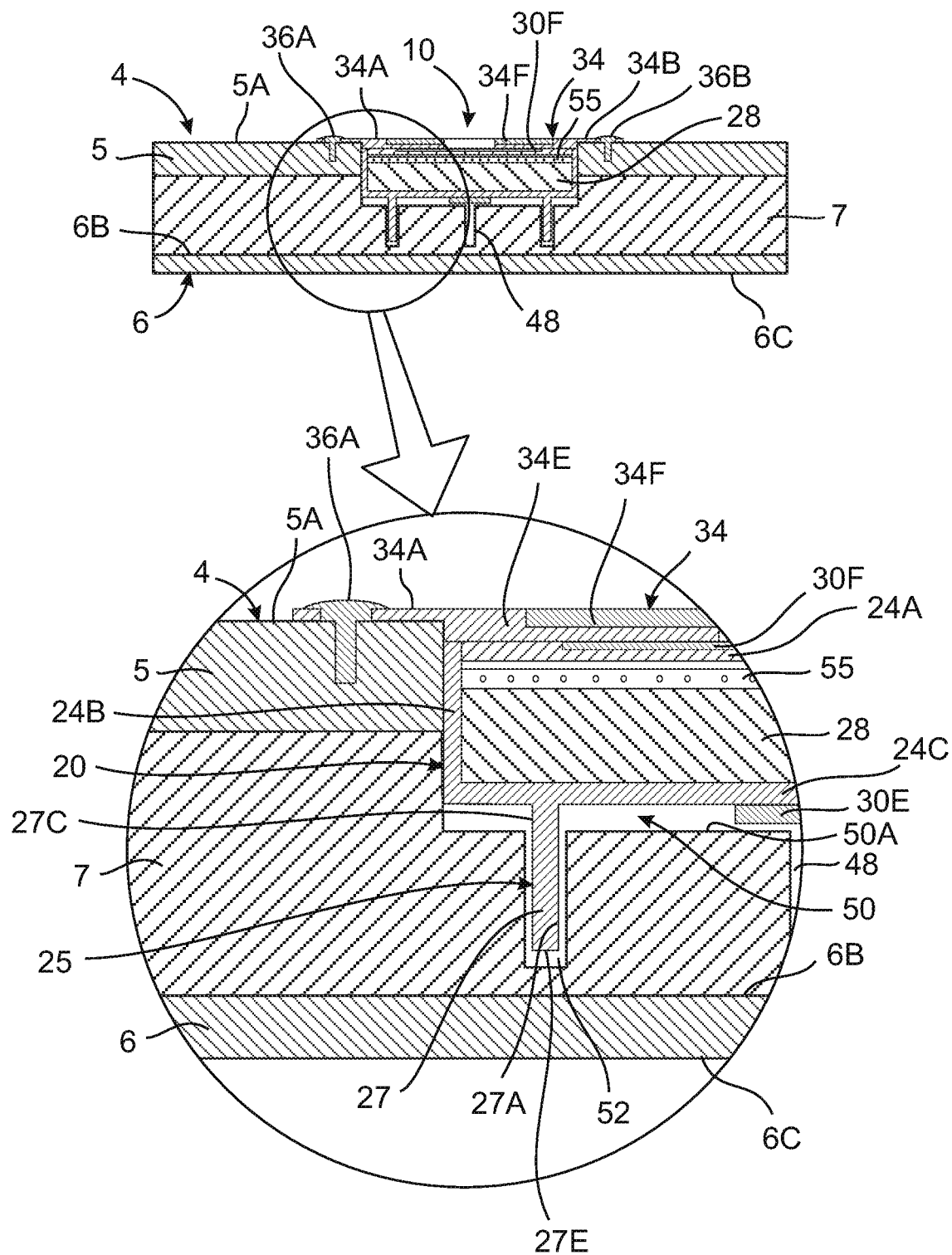
FIG. 12 is a schematic cross-sectional view of the bone and ICI of FIG. 11 taken along the lines XII-XII.

In some embodiments, the ICI 10 may include a first induction coil 55 that is part of a power harvesting module (not shown in detail in FIGS. 1-7 for the sake of clarity of illustration). The power harvesting module may include current conditioning circuitry (not shown in detail), such as, for example a current rectifying circuit that may be electrically coupled to the inductance coil 55 and to a charge storage device (not shown in detail) for storing the electrical charge harvested by the power harvesting module. The current conditioning circuitry and the charge storage device (such as, for example, a capacitor, a super capacitor, a battery, a rechargeable electrochemical cell or any other suitable charge storage device) may be integrated into the ECM 28. In some embodiments, the induction coil 55 may be disposed within the sealed compartment 24 (as illustrated in FIGS. 3 and 12). It is noted that in such embodiments, the top part 24A is preferably made from an electrically non-conducting material, such as, for example, an electrically non-conducting polymer based material or a ceramic material such as, for example, alumina or zirconia based ceramics (alumina based ceramics may be transparent to radio frequencies). This may advantageously prevent shielding of the first inductance coil 55 from the varying magnetic fields provided by a second inductance coil (not shown in FIGS. 1-7 placed on the scalp (for details see FIGS. 13-14 hereinafter). However, in some embodiments, the first inductance coil may be disposed outside of the sealed compartment 24, such as, for example, on top of the top part 24A, or as a coil integrated into the shimming member 34. In such examples, the first inductance coil 55 may be electrically connected to the current conditioning circuitry by suitable electrically insulated leads (not shown) that may sealingly pass into the sealed compartment 24 through suitable sealed passages (not shown) formed in the walls of the sealed compartment 24 that are electrically connected to the current conditioning circuitry disposed within the sealed compartment 24.

Exemplary dimensions for an embodiment of the ICI 10 are as follows: R=7.5 mm, H=4 mm, HS=4.0 mm, the diameter of the sealed compartment is 21 mm, the thickness of the side walls 24B is about 0.5 mm, and the thickness of wall 27 of the current directing member 25 is 0.5 mm. The thickness of the shimming member 34 is 1.5 mm and the diameter of the shimming member 34 is 21 mm (excluding the tabs 34A and 34B). However, the above dimensions are given by way of example only and may change depending, inter alia, on the specific clinical application, the size of the ECM 28, the required number of stimulating/recording electrodes and the thickness of the calvarial bone 4 at the site of implantation.

Returning to FIG. 1, the ICI 10 may also include a shimming member 34. In some embodiments, the shimming member may include a flat annular member having two side tabs 44A and 34B. The tab 34A has a screw hole 34C passing there through, and the tab 34B has a screw hole 34D passing there through. The annular member 34E may be made from titanium of from any of the polymer based materials disclosed in detail hereinabove, or from a suitable ceramic material.

The shimming member 34 may also (optionally) include an annular magnet 34F attached to the annular member 34E. In embodiments in which the source of power for operation of the ICI 10 is a power harvesting module that includes an inductance coil which may receive energy from a second external inductance coil placed upon the scalp of the patient, the magnet 34 may assist in accurate placement of an external inductance coil that may also include a magnet therein. The two magnets may attract each other and enable secure and precise placement of the external inductance coil on the scalp (for an example, see FIGS. 15-16 hereinafter). The surface of the shimming member 34 that faces the top part 24A after implantation may be a flat surface as illustrated in FIGS. 1-2. Alternatively, in some embodiments, the surface of the shimming member 34 that faces the top part 24A after implantation may have a shallow circular recess formed therein (not shown in FIGS. 1-2) and having a diameter that is equal to or very slightly larger than the diameter of the top part 24A of the sealed compartment 24. In such an embodiment (not shown), after the housing 20 is implanted within the calvarial bone, the shimming member may be attached to the housing 20 by pressing the shimming member 34 downwards towards the top part 24A to press-fit the top part 24A within the recess (not shown) formed in the shimming member.

In embodiments in which the bottom surface of the shimming member 34 is flat (as illustrated in FIG. 2, the shimming member 34 may be attached to the top part 24A during implantation by a small drop of biocompatible glue or by one or more suitable small screws (the screws are not shown for the sake of clarity of illustration) that are passed through suitable holes in the shimming member 44 (not shown in FIGS. 1-2, for the sake of clarity of illustration) and are screwed into one or more respective threaded recesses formed in the top part 24A (the threaded recesses in the top part 24 are not shown in FIG. 2 are not shown for the sake of clarity of illustration).

It is noted that the thickness of the calvarial bone may vary widely, based on location in the skull, the patient's age and the patient's physical dimensions. The thickness of the calvarial bone 4 may be as little as 1 mm in the squamosal portion of the temporal bone to as thick as 2 centimeters for some parts of the frontal bone. The thickness of the inner table 6 and the outer table 5 of the calvarial bone may also vary in the range of 0.1-4.0 mm and the thickness of the layer of cancellous bone (diplöe) 7 of the calvarial bone 4 may vary in the range of 0.1 mm-1.9 cm.

The thickness of the shimming member 34 may vary, and the surgeon implanting the ICI 10 may be supplied with a set of different shimming members each having a different thickness. This may be necessary due to the differences in the thickness of the calvarial bone in different patients and in different sites of the calvarial bone in the same patient. A more detailed description of the implantation methods is disclosed hereinafter. Therefore, the thickness of the available shimming members 34 may vary in the range of 1-10 mm, and the thickness of the shimming members 34 may typically vary in steps of about 0.5 mm. This may enable the surgeon to select a shimming member of a suitable thickness such that when the shimming member is attached to the top part 24A, the tabs 34A and 34B will be in contact with the outer surface 5A of the outer table 5 of the calvarial bone 4. However, the steps in the thickness of the shimming members may be in values smaller or larger than 0.5 mm if necessary.

During implantation of the ICI 10, the position of the top part 24A of the sealed compartment relative to the outer table 5 may significantly differ between different implantation sites and between different patients because of the natural variations of the thickness of the calvarial bone or parts thereof. The surgeon or physician may select a shimming member having the appropriate thickness such that after the attachment of the shimming member to the top part 24A of the sealed compartment 24, the tabs 34A and 34B of the annular member 34E are in contact with the exposed outer surface 5A of the outer table 5 (see FIG. 11 hereinafter)

and may be properly attached to the outer table 5 using the screws 36A and 36B (see FIG. 11, hereinafter).

Figure 8:
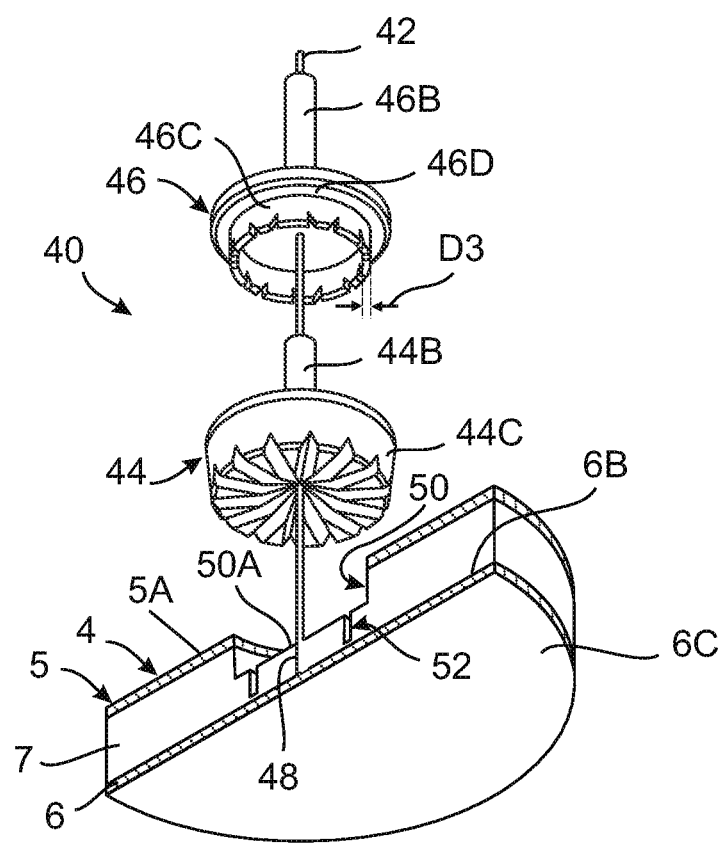
FIG. 8 is a schematic part isometric part cross-sectional view illustrating a drilling system of cannulated drills usable for making appropriate cavities in the calvarial bone for implanting the ICIs of the present application.
Figure 9:
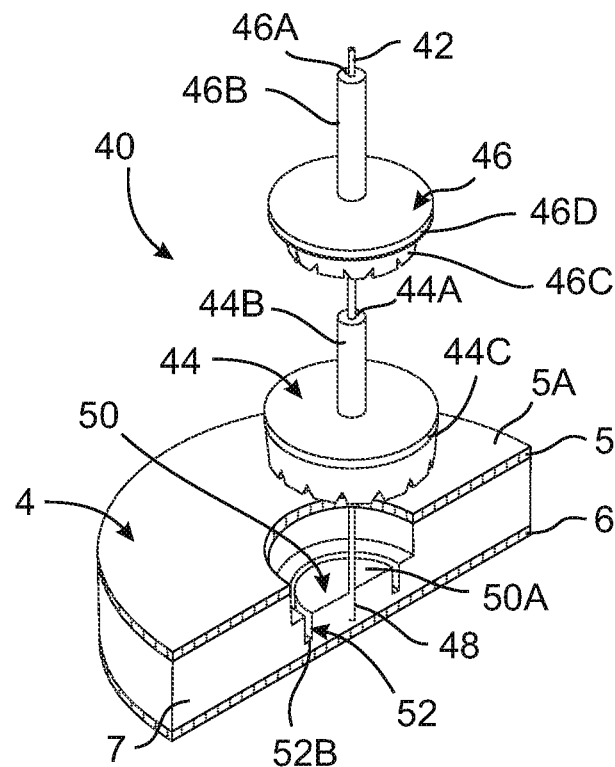
FIG. 9 is another part isometric part cross-sectional view illustrating the drilling system of FIG. 8.
Figure 10:
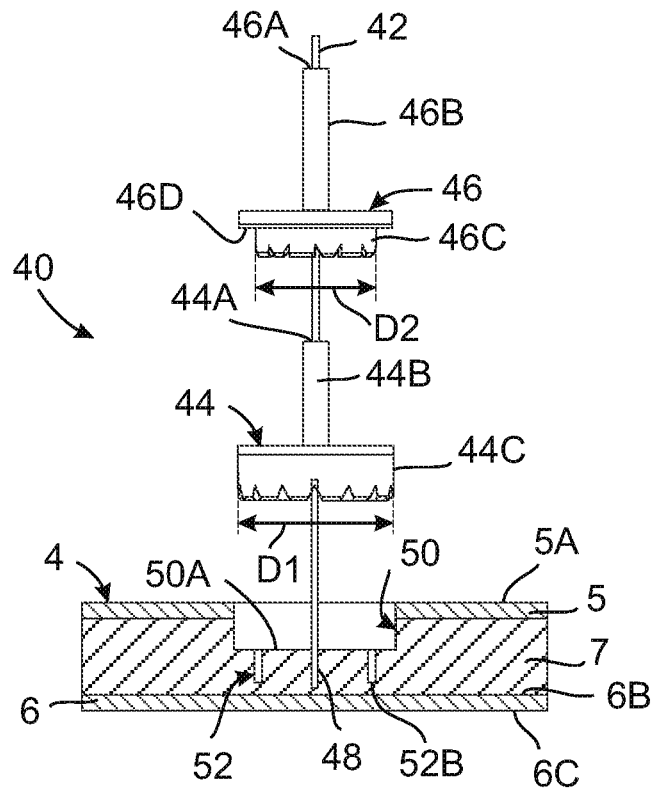
FIG. 10 is another schematic part side view part cross-sectional view illustrating the drilling system of FIG. 8.

Reference is now made to FIGS. 8-10. FIG. 8 is a schematic part isometric part cross-sectional view illustrating a drilling system of cannulated drills usable for making appropriate cavities in the calvarial bone for implanting the ICIs of the present application. FIG. 9 is another part isometric part cross-sectional view illustrating the drilling system of FIG. 8. FIG. 10 is another schematic part side view part cross-sectional view illustrating the drilling system of FIG. 8.

The drilling system 40 may include a guide rod 42, a first cannulated drill bit 44 and a second cannulated cup-like drill bit 46. The first drill bit 44 includes a cannulated drill head 44C, and a cannulated drill shaft. A first cylindrical hollow passage 44A passes through the entire length of the drill head 44C and the drill shaft 44B. The diameter of the hollow passage 44A allows the cannulated drill bit 44 to pass over the guide rod 42 and to freely rotate around the guide rod 42. The second cup-like drill bit 46 includes a cannulated cup-like drill head 46C, and a cannulated drill shaft 46B. A second cylindrical hollow passage 46A passes through the entire length of the cup-like drill head 46C and the drill shaft 46B. The diameter of the hollow passage 46A allows the cannulated cup-like drill bit 46 to pass over the guide rod 42 and to rotate freely around the guide rod 42.

The cup-like drill head 46C has a flange 46D having a flange diameter equal to the diameter of the drill head 44C. The diameter D1 of the first drill head 44C is equal to or slightly larger than the diameter of the sealed compartment 24 of the ICI 10. The external diameter D2 of the second drill head 46C may be equal to or slightly larger than the external diameter of the wall 27. The thickness D3 of the cutting blade of the cup-like second drill head may be either equal to or larger than the combined thickness of the wall 27 and the electrodes (such as the electrodes 30A and 30B of FIG. 4). This ensures that the annular cavity 52 is wide enough to accommodate the wall 27 and the electrodes attached thereto.

The method of implanting the ICI 10 in the calvarial bone 4 of a patient may be as follows: After determining the region of implantation, the patient may be brought into the operating room and induced under general anesthesia. Once the implantation site is identified in imaging space, the implantation location may be localized on the patient's head using a stereotactic navigation system. The implantation site may then be prepared and draped in standard surgical fashion. The skin of the scalp (not shown) may be infiltrated with a local anesthetic and a 1 cm incision may be made in the scalp. A small retractor may be placed in the incision and the surface of the skull is exposed. A small cylindrical guide passage 48 having a diameter equal to the diameter of the guide rod 42 may be then drilled into the calvarial bone 4 using a standard drill bit (not shown). The guide passage 48 may pass through the outer table 5, may extend through the entire cancellous bone layer 7 and may reach the outer surface 6B of the inner table 6. Alternatively, the guide passage 48 may penetrate only through part of the cancellous bone layer 7, without reaching the outer surface 6B of the inner table 6. The bone thickness at the site planned for implantation may be determined from the CT scan of the skull performed prior to implantation.

The guide rod 42 may then be firmly inserted into the guide passage 48 in the calvarial bone 4. The surgeon may then insert the guide rod 42 into the passage 44A within the first cannulated drill bit 44 and may then firmly grasp the drill shaft within a suitable chuck (not shown) a motorized drill (not shown) and activates the motorized drill while lowering the drill bit towards the exposed surface of the calvarial bone to drill a first cavity 50 within the calvarial bone 4. The first cavity 50 may pass through the entire thickness of the outer table 5 and may extend through part of the layer of cancellous bone 7 and has a cavity depth sufficient to accommodate the sealed compartment 24. The depth of the first cavity 50 may also be somewhat larger than the height HS of the sealed compartment 24 (see FIG. 2). After forming the cavity 50, the first cannulated drill bit 44 may be slid upwards over the guide rod 42 to remove the drill bit 44 from the guide rod 42. The second cup-like drill bit 46 is then slid over the guide rod 42 and used with the motorized drill (not shown) to drill a second annular cavity 52 into the cancellous bone layer 7 advancing the drill bit 46 until the drilling is stopped when the flange 46D contacts the flat bottom surface 50A of the first cavity 50. The end 52B of the second annular cavity 52 may reach the outer surface 6B of the inner table 6 or, alternatively, may terminate within the cancellous bone 7 adjacent to the inner table 6. The cup-like drill bit 46 may then be removed from the calvarial bone 4 together with the guide rod 42.

The surgeon may then insert the housing 20 into the cavity 50 until the current directing mechanism 25 is disposed within the second annular cavity 52 and the sealed compartment is disposed within the first cavity 50. The surgeon may then measure the distance between the top surface of the upper part 24A and the outer surface 5A of the outer table 5 and may select a suitable shimming member 34 from an available selection of shimming members having different thicknesses to ensure that when the shimming member 34 is attached to the sealed compartment 24, the side tabs 34A and 34B will contact the outer surface 5A of the outer table 5 of the (exposed) part, of the calvarial bone 4. The surgeon may then attach the shimming member 34 to the top part 24A by firmly press fitting the shimming member 34 (for embodiments in which the shimming member 34 has a recessed bottom part as disclosed in detail hereinabove), or by applying one or more small drops of a suitable biocompatible glue to the upper part of the top part 24A and pressing the shimming member 34 onto the top part 24 (for embodiments having a flat bottom surface of the shimming member 34), or by using suitable small screws (not shown) to attach the shimming member 34 to the top part 24A (as disclosed in detail hereinabove).

After the ICI 10 has been secured to the calvarial bone 4, the skin flaps of the incision made in the scalp (not shown) may be closed to allow the scalp to cover the implantation region and to allow the scalp incision to heal. A few days after implantation, the ICI 10 may become attached within the cavity 50 by scar tissue that may further reduce or prevent undesirable movements or rotation of the ICI 10 within the cavity 50.

Figure 11:
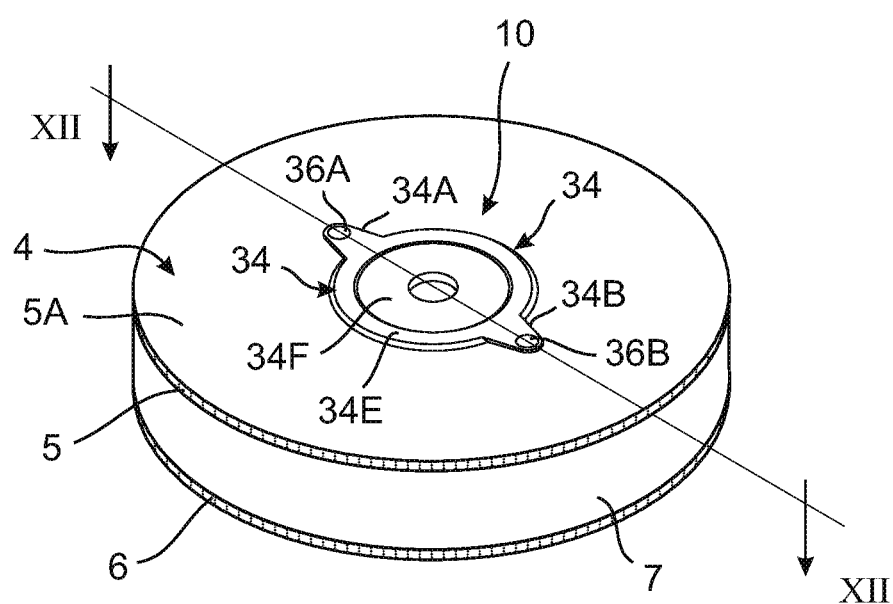
FIG. 11 is a schematic isometric view illustrating part of the calvarial bone with an ICI therein, in accordance with some embodiments of the present application.

Reference is now made to FIGS. 11-12. FIG. 11 is a schematic isometric view illustrating part of the calvarial bone with an ICI therein, in accordance with some embodiments of the present application. FIG. 12 is a schematic cross-sectional view of the bone and ICI of FIG. 11 taken along the lines XII-XII.

Turning to FIG. 11, the ICI 10 is I illustrated as implanted within part of the calvarial bone 4. The calvarial bone 4 includes an outer table 5, an inner table 6 and a layer of cancellous bone (Diplöe) 7 disposed between the outer table 5 and the inner table. The outer table has an outer surface 5A which is the surface of the skull. It is noted that the scalp overlying the calvarial bone is not shown in FIG. 11, for the sake of clarity of illustration. The shimming member 34 is shown as attached to the calvarial bone 4 by a pair of bone screws 36A and 36B that pass through the openings 34C of the tab 34A and 34D of the tab 34B, respectively.

Turning now to FIG. 12, the ICI 10 is illustrated as implanted in the calvarial bone 4. It is noted that the scalp overlying the calvarial bone 4, is not shown in FIG. 12 for the sake of clarity of illustration. The wall 27 of the current directing mechanism 25 is disposed within the annular cavity 52 and the sealed compartment 24 of the housing 20 is disposed within the cavity 50. The remaining part of the guide passage 48 used during implantation for placement of the guide rod 42 may also be seen extending from the bottom surface 50A of the cavity 50 towards the inner table 6. The shimming member 34 is attached to the top part 24A of the sealed compartment 24. The shimming member 34 is shown as attached to the calvarial bone 4 by the pair of bone screws 36A and 36B that pass through the openings 34C of the tab 34A and 34D of the tab 34B, respectively. The reference electrode 30E may be in contact with the bottom surface 50A of the cavity 50. It is noted that none of the electrodes 30A, 30B, 30C and 30D may be seen in the specific cross-sectional view of FIG. 12. However, the electrodes 30A, 30B, 30C and 30D are also disposed within the annular cavity 52.

It is noted that while the end 52B of the annular cavity is shown as extending within the layer of cancellous bone 7 but not quite reaching the outer surface 6B of the inner table 6, this is not obligatory to practicing the invention. Rather, in some embodiments, the end 52B of the annular cavity 52 may extend all the way to the outer surface 6B of the inner table 6 (not shown in FIG. 12). Furthermore, in some embodiments, the end 52B of the annular cavity 52 may even slightly extend into the inner table 6 (not shown in FIG. 12) but without breaching (fully penetrating) the inner table 6. Such embodiments may have the advantage that the electrodes 30A, 30B, 30C and 30D may be placed nearer the surface of the brain which may improve stimulation of the brain (or may require less current for effective cortical stimulation leading power savings) and may also improve sensing of cortical electrical signals (by increasing the signal to noise ratio). However, if such embodiments are practiced, care should be taken not to weaken the inner table 6 by penetrating too deeply into the inner table 6. It is noted that the tissues underlying the inner table 6 are not shown in FIG. 12 for the sake of clarity of illustration.

The close proximity of the electrodes 30A, 30B, 30C and 30D to the brain tissue and the shape of the current directing mechanism 25 may significantly improve the quality of sensing of electrical cortical signals relative to EEG scalp surface sensing and may also improve cortical stimulation by focally directing the stimulating currents as is disclosed hereinafter.

Figure 13:
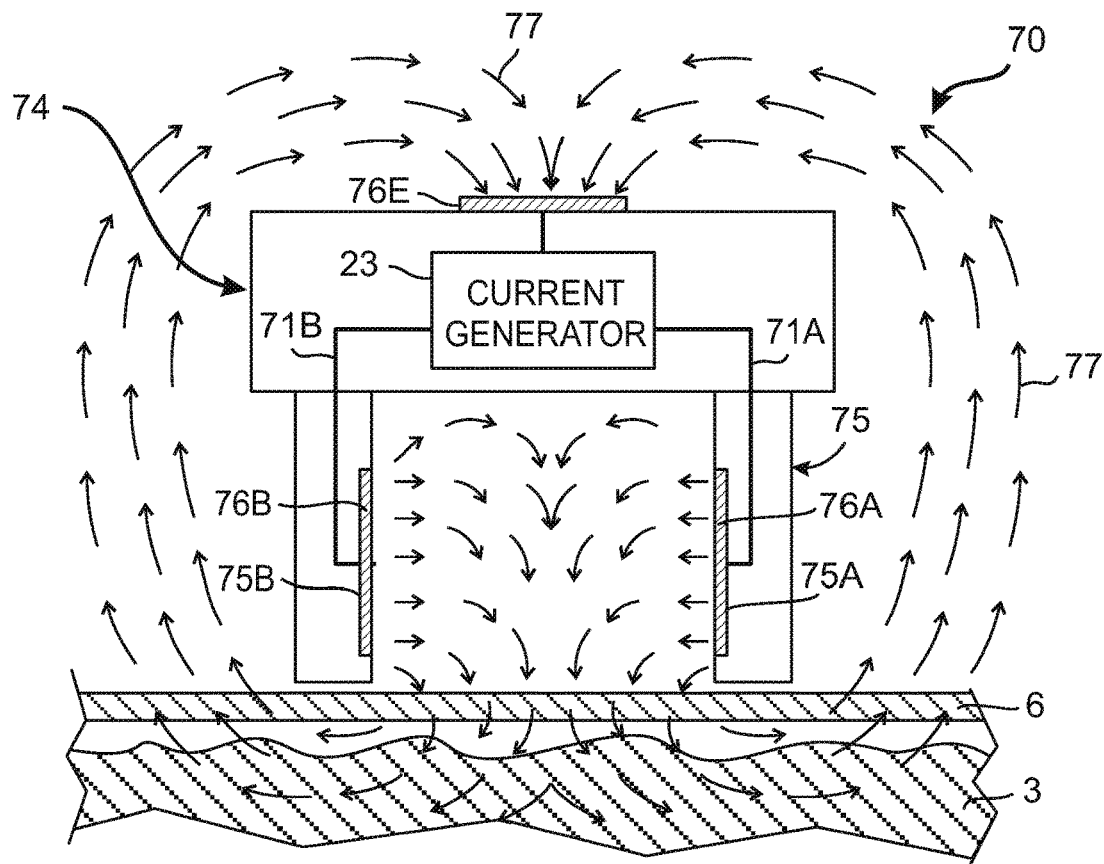
FIG. 13 is a schematic part cross-sectional part block diagram schematically illustrating the current flow lines in an ICI embodiment operating in a stimulating mode, in accordance with some embodiments of the ICIs of the present application.
Figure 14:
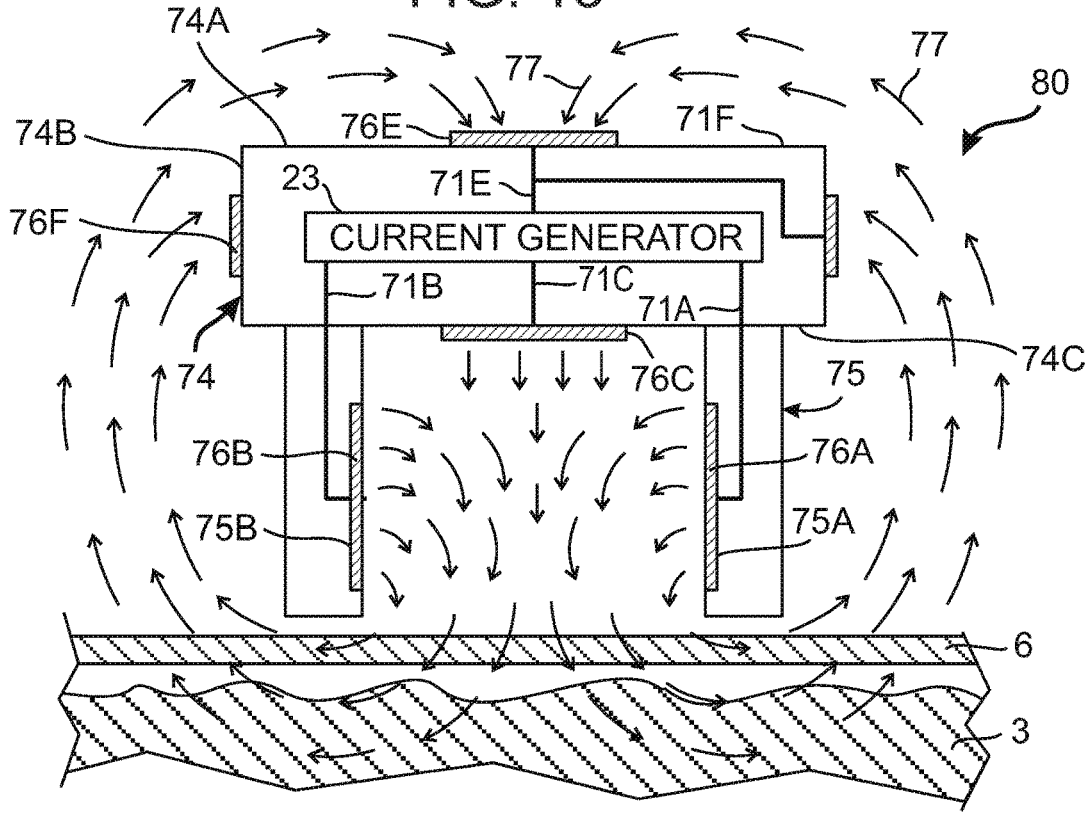
FIG. 14 is a schematic part cross-sectional part block diagram schematically illustrating the current flow lines in another ICI embodiment operating in a stimulating mode, in accordance with some embodiments of the ICIs of the present application.

Reference is now made to FIGS. 13-14. FIG. 13 is a schematic part cross-sectional part block diagram schematically illustrating the current flow lines in an ICI embodiment operating in a stimulating mode, in accordance with some embodiments of the ICIs of the present application. FIG. 14 is a schematic part cross-sectional part block diagram schematically illustrating the current flow lines in another ICI embodiment operating in a stimulating mode, in accordance with some embodiments of the ICIs of the present application. It is noted that FIGS. 13-14 are highly schematic diagrams that are meant solely to illustrate the approximate qualitative current flow lines patterns. It is noted that in FIGS. 13-14, only the inner table 6 and the cortex 3 are schematically illustrated and other parts of the calvarial bone are not shown in order to clearly demonstrate the current pathways during stimulation.

Turning to FIG. 13, the ICI 70 includes a sealed compartment 74 and a current directing mechanism 75. Stimulating electrodes 76A and 76B are partially embedded in suitable recesses 75A and 75B formed in the wall of the current directing mechanism 75. A ground (return) electrode 76E is attached to the top part of the sealed compartment 74. An ECM (not shown for the sake of clarity of illustration) similar to the ECM 28 of FIG. 1 is enclosed in the sealed compartment 74 and includes a current generator 23. It is noted that only the current generator 23 is schematically shown in FIG. 13 for the sake of clarity of illustration. The electrodes 76A, 76B and 76E are electrically connected to the current generator 23 by suitable insulated leads 71A, 71B and 71E, respectively.

When the ICI 70 is in a stimulating mode, current may be passed between the stimulating electrodes 76A and 76B, and the ground electrode 76E. The current directing member 75 that is electrically non-conducting directs the current schematically represented by the arrows 77. Since the current cannot pass through the walls of the current directing mechanism 75, the resulting currents are forced to penetrate into the inner table 6 and into the cortical tissue 3 underlying the inner table and to electrically stimulate the cortex 3.

Turning now to FIG. 14, the ICI 80 includes a sealed compartment 74 and a current directing mechanism 75. Stimulating electrodes 76A and 76B are partially embedded in or suitably attached within suitable recesses 75A and 75B formed in the wall of the current directing mechanism 75. Another stimulating electrode 76C is attached to the bottom part 74C of the sealed compartment 74. A ground (return) electrode 76E is attached to the top part 74A of the sealed compartment 74. Another ground (return) electrode 76F is formed as a ring-like electrode attached to the side walls 74B of the sealed compartment 74. An ECM (not shown for the sake of clarity of illustration) similar to the electronic circuitry 28 of FIG. 1 is sealingly enclosed in the sealed compartment 74 and includes a current generator 23. It is noted that only the current generator 23 of the ECM is schematically shown in FIG. 14 for the sake of clarity of illustration. The electrodes 76A, 76B and 76C are electrically connected to the current generator 23 by suitable insulated leads 71A, 71B and 71C, respectively. The ground electrodes 76E and 76F may be electrically interconnected and are electrically connected to the current generator 23 by suitable insulated leads 71E and 71F.

When the ICI 80 is in a stimulating mode, current may be passed between the stimulating electrodes 76A, 76B, 76C, and the ground electrodes 76E and 76F. The current directing member 75 that is electrically non-conducting directs the current schematically represented by the arrows 77. Since the current cannot pass through the walls of the current directing mechanism 75, the resulting currents are forced to penetrate into the inner table 6 and into the cortical tissue 3 underlying the inner table and to electrically stimulate the cortex 3.

It is noted that the ICI 80 may also have a sensing/recording mode. In the sensing/recording mode currents are not passed between the electrodes as disclosed hereinabove but differential recording of one or more electrode pairs may be performed. For example, differential recording of cortical signals may be performed by the electrode pair 76C and 76A or by the electrode pair 76C and 76B, or simultaneously between both the electrode pairs 76C, 76A and 76C, 76A. In such an embodiment, the electrode 76C may be used for stimulation in the stimulating mode and may also be used as a reference electrode in a sensing/recording mode.

It is also noted that the direction of the currents shown in FIGS. 13-14 assumes anodic stimulation for cathodic stimulation the direction of the currents (and arrows 77) would be reversed.

The tissue structures interposed between the inner table 6 and the cortex 3 (such as the dura matter, the arachnoid, blood vessels and the pia matter) are not shown in the highly schematic FIGS. 13-14 for the sake of clarity of illustration.

Figure 15:
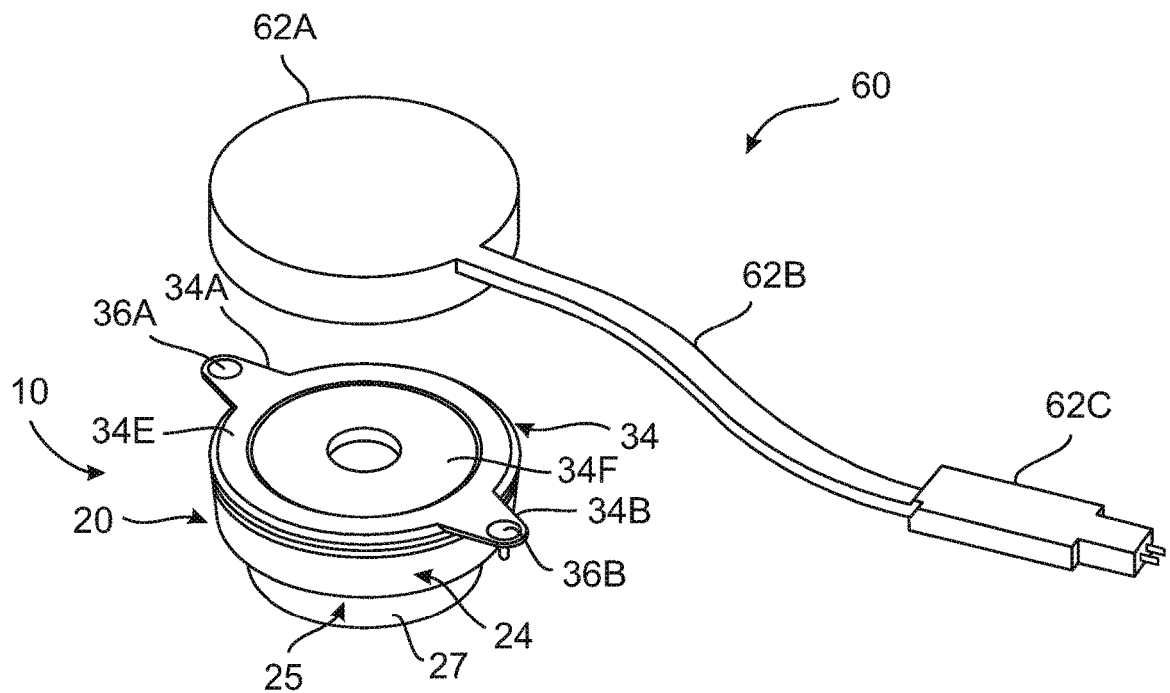
FIG. 15 is a schematic isometric view of the ICI of FIG. 1 illustrated with an external inductance coil for wirelessly providing electrical power to the ICI, in accordance with some embodiment of the ICIs of the present application.
Figure 16:
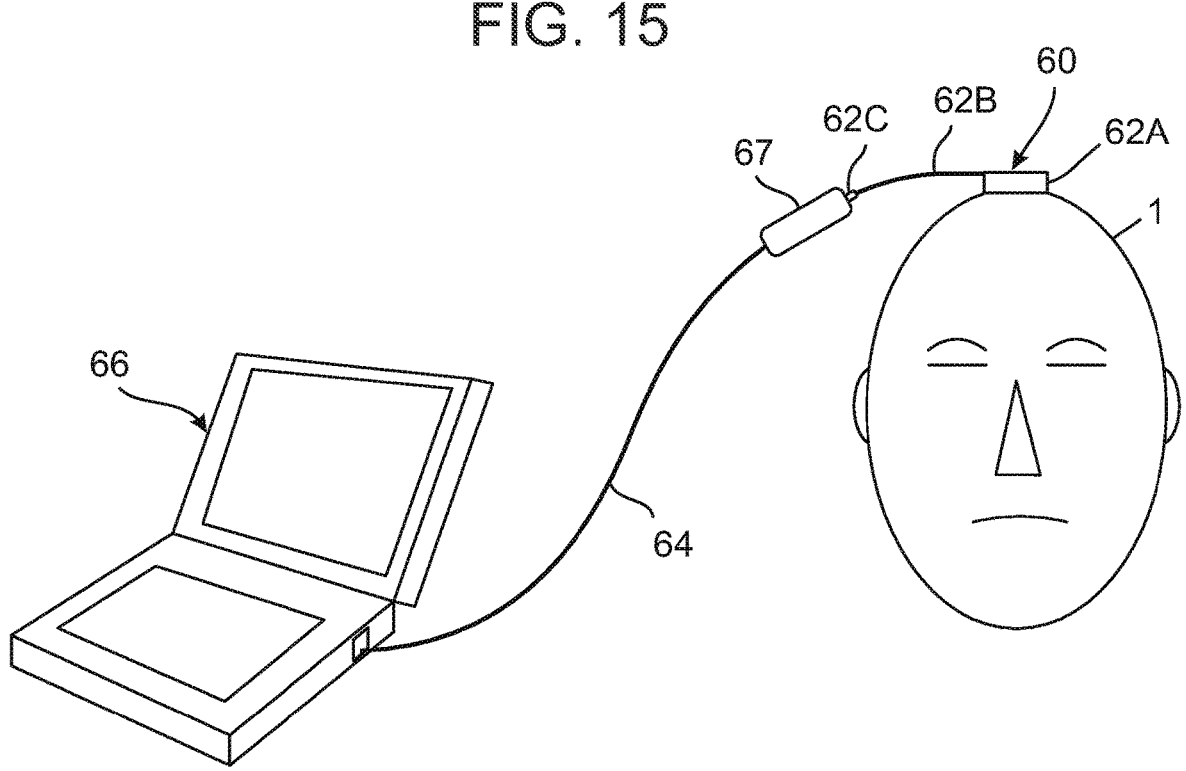
FIG. 16 is a schematic diagram illustrating a system for wirelessly providing electrical power to an implanted ICI.

Reference is now made to FIGS. 15-16. FIG. 15 is a schematic isometric view of the ICI of FIG. 1 illustrated with an external inductance coil for wirelessly providing electrical power to the ICI, in accordance with some embodiment of the ICIs of the present application. FIG. 16 is a schematic diagram illustrating a system for wirelessly providing electrical power to an implanted ICI.

Turning to FIG. 15, the ICI 10 is shown outside the calvarial bone (for the sake of clarity of illustration), an external inductance coil 60 is positioned above the ICI 10. The external inductance coil 60 may include a coil housing 62A that includes an electrically conducting inductance coil therein (the coil itself is not seen in the isometric view of FIG. 15). The external inductance coil 60 may also include a lead 62B and a connector 62C. The lead 62B may include a pair of conducting wires (not shown), electrically connected to the inductance coil and terminating in the connector 62C. In accordance with some embodiments, the coil housing 62A may include a magnet (not shown) embedded therein or attached thereto.

Turning to FIG. 16, the external inductance coil 60 is illustrated as positioned on the head 1 of a patient that has the ICI 10 implanted in the calvarial bone of the head 1. (it is noted that the ICI 10 is not seen in FIG. 16 because it is covered by the scalp after implantation). The coil housing 62A is placed on the scalp of the patient and the magnet embedded in the coil housing 62A may be attracted by the magnet 34F included in the shimming member 34 of the ICI in 10. The attraction between the magnets assists the placement of the external induction coil 60 at the correct position above the inductance coil 55 disposed within the sealed compartment 24 of the ICI 10 (see FIG. 12 hereinabove). The attraction between the magnets may also assists in preventing undesirable movements of the coil housing 62A along the scalp during the energizing of the ICI 10 by the external inductance coil 60. The connector 62C may be connected to a suitable socket in a powering module 65 and the powering module 65 may be suitably connected to a computer 66 by a connecting cable (such as, for example a USB cable). The powering module 65 may include an electrical power source (such as, for example, a battery, a primary electrochemical cell, a rechargeable electrochemical cell) and suitable electrical circuitry for controlling the delivery of alternating current or pulsatile current to the external induction coil 60. In some embodiments, the operation of the powering module 65 may be controlled by the computer 66.

It is noted that the construction and operation of the external inductance coil 60 is well known in the art, is not the subject of the present application and is therefore not described in detail herein. For example, U.S. Pat. No. 6,246,911 to Seligman disclosed the construction and use of inductance coils for energizing cochlear implants.

It is noted that while the current directing mechanism 25 of the ICI 10 includes a single wall 27, this is not obligatory to practicing the invention. Rather, the present application contemplates ICIs having current directing mechanisms including multiple walls.

Figure 17:
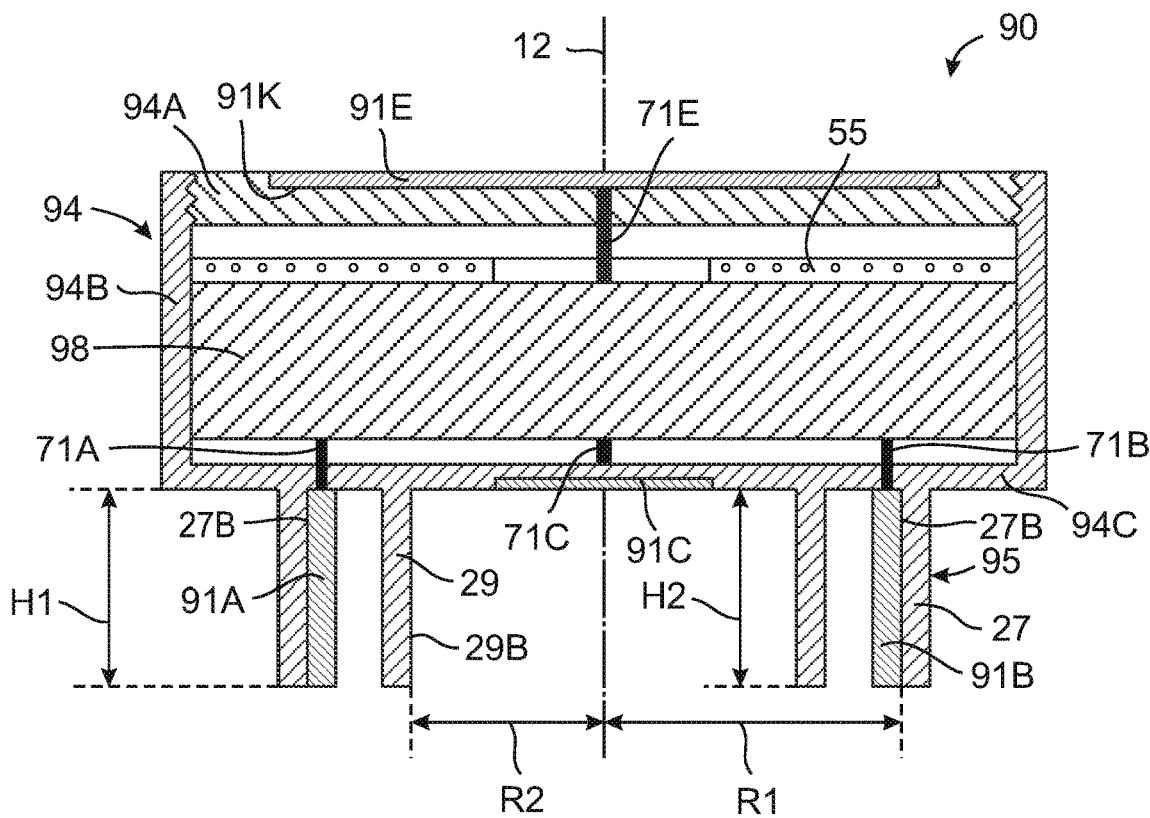
FIG. 17 is a schematic cross-sectional view illustrating part of an ICI having a current directing mechanism having two walls, in accordance with some embodiments of the ICIs of the present application.
Figure 18:
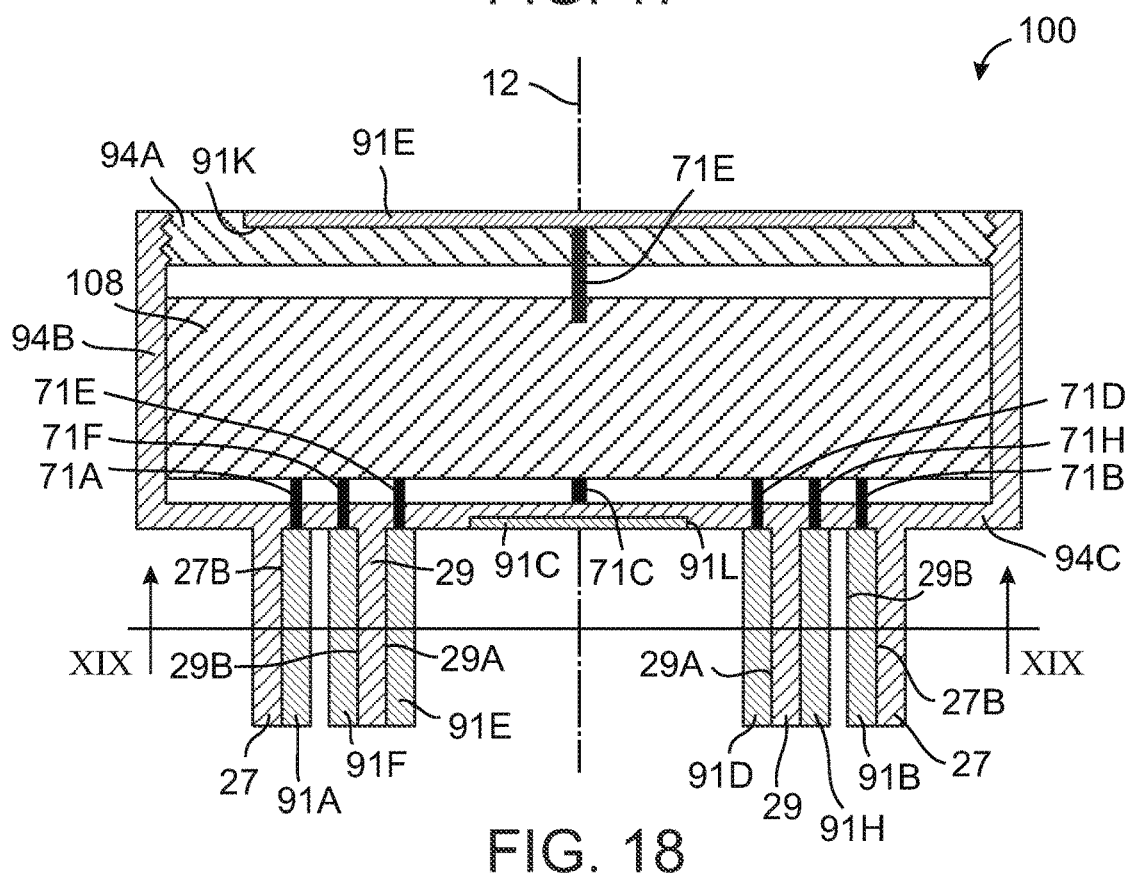
FIG. 18 is a schematic cross-sectional view illustrating part of an ICI having a current directing mechanism having two walls with a different electrode arrangement, in accordance with some embodiments of the ICIs of the present application.
Figure 19:
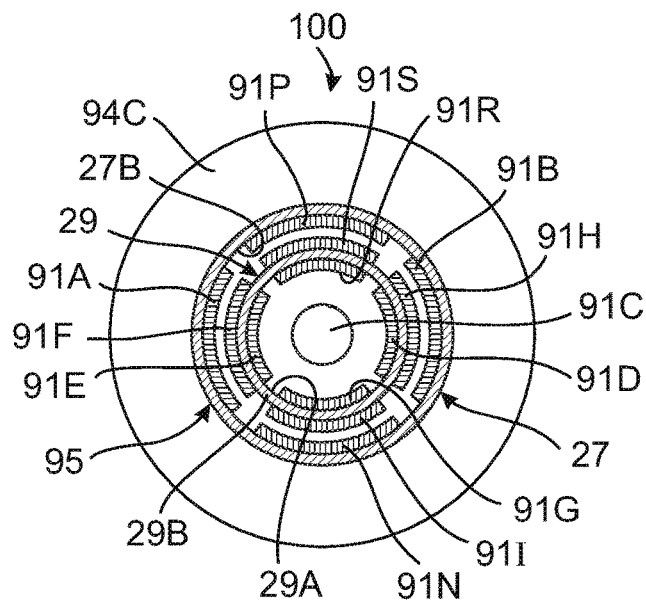
FIG. 19 is a schematic cross sectional view of the ICI of FIG. 18 taken along the lines XIV-XIV.
Figure 20:
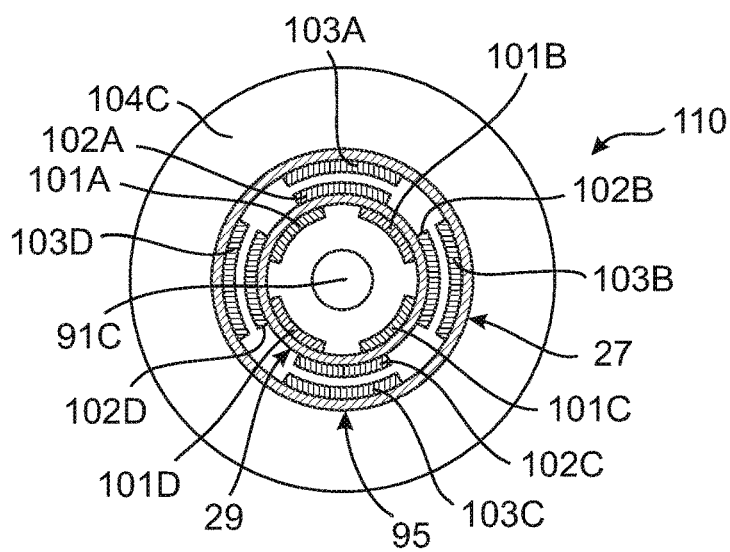
FIG. 20 is a schematic cross-sectional view illustrating the electrode arrangement of another embodiment of an ICI with a double walled current directing mechanism.
Figure 21:
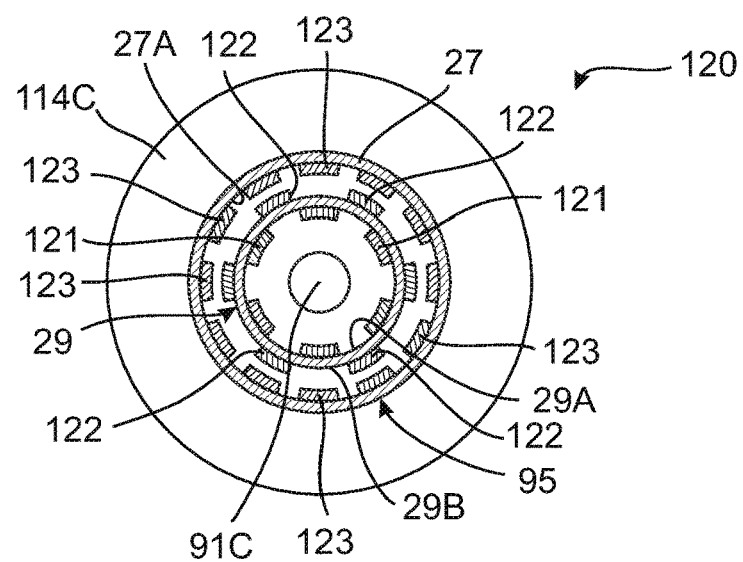
FIG. 21 is a schematic cross-sectional view illustrating the electrode arrangement of yet another embodiment of an ICI with a double walled current directing mechanism.

Reference is now made to FIGS. 17-22. FIG. 17 is a schematic cross-sectional view illustrating part of an ICI having a current directing mechanism having two walls, in accordance with some embodiments of the ICIs of the present application. FIG. 18 is a schematic cross-sectional view illustrating part of an ICI having a current directing mechanism having two walls with a different electrode arrangement, in accordance with some embodiments of the ICIs of the present application. FIG. 19 is a schematic cross sectional view of the ICI of FIG. 18 taken along the lines XIV-XIV. FIG. 20 is a schematic cross-sectional view illustrating the electrode arrangement of another embodiment of an ICI with a double walled current directing mechanism. FIG. 21 is a schematic cross-sectional view illustrating the electrode arrangement of yet another embodiment of an ICI with a double walled current directing mechanism.

Turning to FIG. 17, the ICI 90 may include a sealed compartment 94 having a top part 94A, side wall 94B and a bottom part 94C. The sealed compartment 94 has an axis of symmetry 12 passing there through. The ICI 90 may also include a current directing mechanism 95, attached to or extending from the bottom part 94C. The current directing mechanism 95 includes an external cylindrical wall 27 (of FIG. 6) having a height H1 and an internal cylindrical wall 29 having a height H2. Preferably, but not obligatorily, H1=H2 as illustrated in FIG. 17. However, in some embodiments of the ICI 90 H1>H2 and in some other embodiments H1<H2. The external wall 27 and the internal cylindrical wall 29 may be concentric. The ICI 90 also includes an ECM 98 and an inductance coil 55 electrically connected to a power harvesting module (not shown for the sake of clarity of illustration) included within the ECM 98.

The ICI 90 may also include a shimming member (not shown in FIG. 17). The shimming member of the ICI 90 may be the shimming member 34 disclosed in detail hereinabove with respect to FIGS. 1-6. The ICI 90 may also include multiple stimulating/recording electrodes (it is noted that only the stimulating/recording electrodes 91A and 91B are seen in the cross-sectional view of FIG. 17). The electrodes 91A and 91B may be electrically connected to the ECM 98 by electrically insulated electrically conducting leads 71A and 71B, respectively that sealingly pass through suitable passages formed in the bottom part 94C of the sealed compartment 94. The stimulating/recording electrodes 91A and 91B may be attached to or may be disposed adjacent to the inner surface 27B of the wall 27. The ICI 90 may also include a ground (return) electrode 91E and a reference electrode 91C suitably electrically connected to the ECM 98 by electrically insulated electrically conducting leads 71E and 71C. The ground electrode 91E may be partially embedded or attached within a recess 91K formed within the top part 94A and the reference electrode 91C may be partially embedded or attached within a recess 91L formed within the bottom part 94C.

The stimulating/recording electrodes (such as, for example, the electrodes 91A and 91B) may be disposed between the external wall 27 and the internal wall 29 of the current directing member 95 and may be attached to the external wall 27 as illustrated in FIG. 17. However, in some embodiments of the ICI 90, some or all the stimulating/recording electrodes may be attached to or adjacent to the internal wall 29. In some embodiments of the ICI 90, some or all of the stimulating/recording electrodes may be disposed between the walls 27 and 29 without being attached to the walls 27 and 29.

The radius between the symmetry axis 12 and the internal surface 29B of the internal wall 29 is R1 and the radius between the symmetry axis 12 and the internal surface 27B of the external wall 27 is R2. Preferably, but not obligatorily, H1≥0.5R1 and H2≥0.5R2 for the same reasons explained in detail hereinabove for the wall 27 of the ICI 10.

An advantage of using a current directing mechanism having two walls (as illustrated in FIG. 17), may be that the two walls even further confine or focalize the stimulating current pathways during stimulation and may result in either deeper penetration of the stimulating currents into the cortical tissue underlying the inner table 6, compared to the current pathways at the same current applied to the same electrodes in an ICI having a single wall (such as for example the wall 27) in the current directing mechanism having the same position and dimensions as the wall 27 of the ICI 90. Furthermore, the use of double walled ICI may increase the current density in regions underlying the ICI which may allow to reduce the current intensity while achieving sufficient cortical stimulation which may advantageously conserve power.

It is noted that the method of implantation of the ICI 90 may be quite similar to the method for implanting the ICI 10 except that the second drill bit 44 may have to be modified, or, alternatively an additional drill bit may have to be used during implantation. One possible modification may be to increase the thickness D3 of the cutting blade of the drill head 46C, such that the resulting width of the annular cavity 52 will be large enough to accommodate both walls 27 and 29 and any electrodes attached to the walls 27 and/or 29. Another possible modification of the implantation method is to use the second drill bit to drill the cavity 52 for accommodating the wall 27 and any electrodes attached thereto and then to use a third cup-like drill bit (not shown) that has a diameter smaller that the diameter D2 to drill a second annular cavity (not shown) having a width sufficient to accommodate the wall 29.

Turning to FIG. 18, the ICI 100 may include the sealed compartment 94 having a top part 94A, side wall 94B and a bottom part 94C. The sealed compartment 94 has an axis of symmetry 12 passing there through. The ICI 100 may also include a current directing mechanism 95, attached to or extending from the bottom part 94C. The current directing mechanism 95 includes an external cylindrical wall 27 (of FIG. 6) and an internal cylindrical wall 29 having a diameter smaller than the diameter of the wall 27. The external wall 27 and the internal wall 29 may be concentric. The ICI 90 also includes an ECM 108 and an inductance coil (not shown) electrically connected to a power harvesting module (not shown for the sake of clarity of illustration) included within the ECM 98. The inductance coil (not shown) may be integrated into the ECM 108 and is therefore not shown in FIG. 18. For example, such an integrated induction coil may be an electrically conducting coil printed on a printed circuit board (PCB) included in the ECM 108 (the PCB is not shown in detail in FIG. 18, for the sake of clarity of illustration).

The ICI 100 may also include a shimming member (not shown in FIG. 18). The shimming member of the ICI 100 may be the shimming member 34 disclosed in detail hereinabove with respect to FIGS. 1-6. The ICI 100 may also include multiple stimulating/recording electrodes (it is noted that only the stimulating/recording electrodes 91A, 91B, 91D, 91E, 91F and 91H are seen in the cross-sectional view of FIG. 18). The electrodes 91A, 91B, 91D, 91E, 91F and 91H may be electrically connected to the ECM 108 by electrically insulated electrically conducting leads 71A, 71B, 71D, 71E, 71F and 71H, respectively, that sealingly pass through suitable passages formed in the bottom part 94C of the sealed compartment 94. The ICI 100 may also include a ground (return) electrode 91E and a reference electrode 91C suitably electrically connected to the ECM 108 by electrically insulated electrically conducting leads 71E and 71C. The ground electrode 91E may be partially embedded or attached within a recess 91K formed within the top part 94A and the reference electrode 91C may be partially embedded or attached within a recess 91L formed within the bottom part 94C. Some of the stimulating/recording electrodes (such as, for example, the electrodes 91A, 91B) may be disposed between the external wall 27 and the internal wall 29 of the current directing member 95 and may be attached to or adjacent to the inner surface 27A of the external wall 27. Some other stimulating/recording electrodes (such as, for example the electrodes 91H and 91F) may be attached to or disposed adjacent to the outer surface 29B of the wall 29. Some other stimulating/recording electrodes (such as, for example, the electrodes 91D and 91E) may be attached to or disposed adjacent to the inner surface 29A of the wall 29.

Turning now to FIG. 19, the four stimulating/recording electrodes 91A, 91B, 91P and 91N may be attached to or disposed adjacent to the inner surface 27A of the wall 27. The four stimulating/recording electrodes 91F, 91H, 91I and 91S may be attached to or disposed adjacent to the outer surface 29A of the wall 27. The four stimulating/recording electrodes 91D, 91E, 91G and 91R may be attached to or disposed adjacent to the inner surface 29A of the wall 29.

An advantage of the ICI 100 is that a larger surface area is available for electrode placement, which may allow larger total electrode surface area for passing current, additionally and/or alternatively, a larger number of electrodes may be used when additional surfaces of the walls 27 and 29 are being used for electrode placement as compared to the ICI 90. The larger number of electrodes may result in a higher recording resolution and may also allow recording over a larger total cortical region.

It is noted that the method of implantation of the ICI 90 may be quite similar to the method for implanting the ICI 10 except that the second drill bit 44 may have to be modified, or, alternatively an additional drill bit may have to be used during implantation. One possible modification may be to increase the thickness D3 of the cutting blade of the drill head 46C, such that the resulting width of the annular cavity 52 will be large enough to accommodate both walls 27 and 29 and any electrodes attached to the walls 27 and/or 29. Another possible modification of the implantation method is to use the second drill bit to drill the annular cavity 52 for accommodating the wall 27 and any electrodes attached thereto and then to use a third cup-like drill bit (not shown) that has a diameter smaller that the diameter D2 to drill a second annular cavity (not shown) having a width sufficient to accommodate the wall 29.

Turning now to FIG. 20, the ICI 110 may be similar to the ICI 100 with the exception that the some of the stimulating/recording electrodes may be differently arranged within the current directing mechanism. The stimulating/recording electrodes 103A, 103B 103C, 103D, 102A, 102B, 102C and 102D of the ICI 110 are arranged similar to the electrodes 91P, 91B, 91N, 91A, 91S, 91H, 91I and 91F respectively, of ICI 100. However, the four electrodes 101A, 101B, 101C and 101D are staggered with respect to the four electrodes 102A, 102B, 102C and 102D.

Turning now to FIG. 21, the ICI 120 is similar to the ICIs 100 and 110 except that is has a larger number of electrodes that are differently arranged within the current directing mechanism 95. The ICI 120 may include a first group of six electrodes 121 attached to or disposed adjacent to the inner surface 27A of the wall 27, a second group of six electrodes 122 disposed adjacent to or attached to the outer surface 29B of the wall 29 and a third group of twelve electrodes 123 adjacent to or attached to the inner surface 27A of the wall 27.

Figure 22:
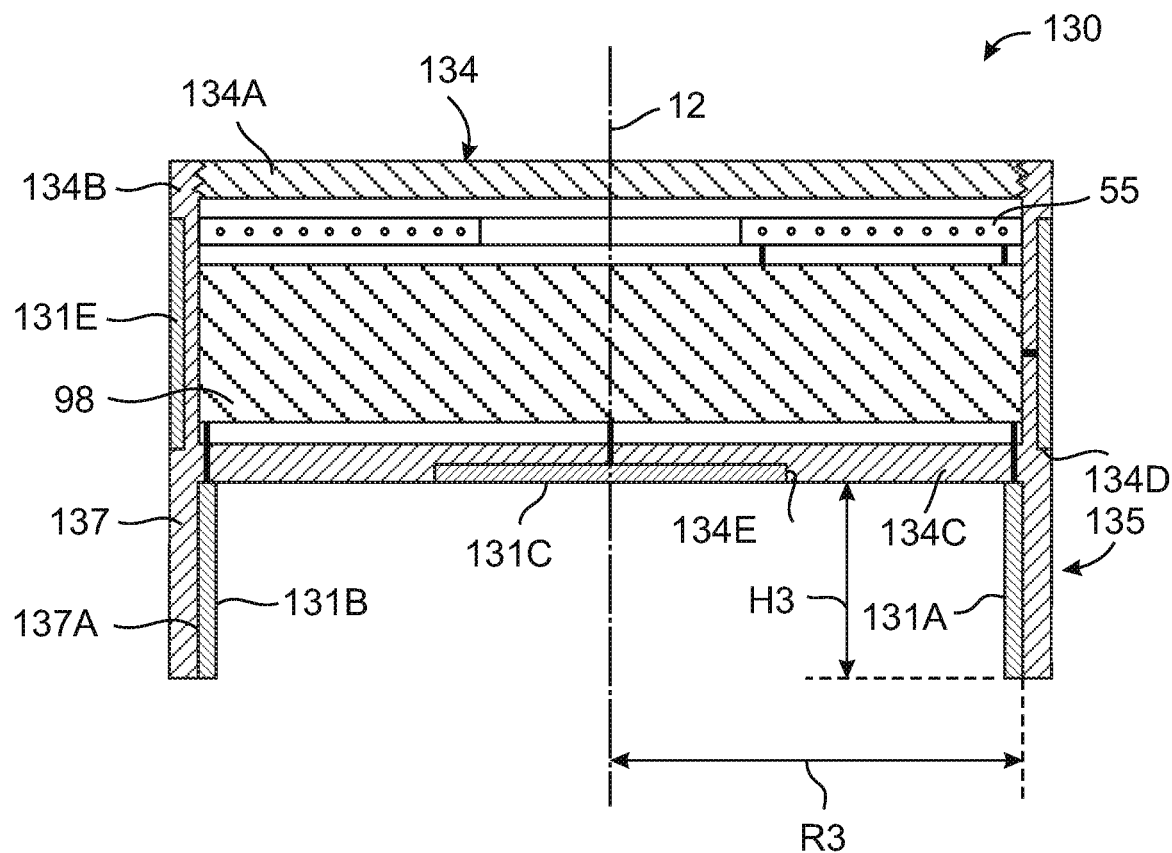
FIG. 22 is a schematic cross sectional view illustrating an ICI, in accordance with yet another embodiment of the ICIs of the present application.

Reference is now made to FIG. 22 which is a schematic cross sectional view illustrating an ICI, in accordance with yet another embodiment of the ICIs of the present application. The ICI 130 may include a cylindrically shaped sealed compartment 134 including a top part 134A, a bottom part 134C and side wall 134B extending between the top part 134A and the bottom part 134C. The ICI 130 may also include the shimming member 34 as disclosed with respect to the ICI 10 hereinabove (the shimming member 34 is not shown in FIG. 22 for the sake of clarity of illustration). The ICI 130 may also include the ECM 98 and the inductance coil 55 as disclosed hereinabove with respect to FIG. 17. The ICI 130 may also include a current directing mechanism 135. The current directing mechanism 135 may include a cylindrical wall 137 extending from the bottom part 134C as a contiguous part thereof or, alternatively attached to the bottom part 134. It is noted that the wall 137 of the current directing mechanism 135 has a diameter identical to the diameter of the sealed compartment 134.

The ICI 130 may also include a ring-like ground (return) electrode 131E that may be attached within a suitable recess 134D formed in the side walls 134B. Alternatively, the ground electrode 131E may be attached to or coated upon the external surface of the side wall 134B. The ICI 130 may also include a reference electrode 131C attached within a suitable recess 134E formed within the bottom part 134C. Alternatively, the reference electrode 131C may be attached to the external surface of the bottom part 134C. The ICI 130 may also include multiple stimulating/recording electrodes. It is noted that only the stimulating/recording electrodes 131A and 131B may be seen in the cross-sectional view of FIG. 22. The advantage of the ICI 130 is that it may substantially increase the surface area 137A available for electrode placement and/or may enable using a higher number of electrodes as compared to ICIs in which the current directing mechanism has a single wall having a diameter smaller than the diameter of the wall 137 (such as, for example the ICI 10). The diameter of the cylindrical inner surface 137A is R3 and the height of the wall 137 is H3. While the surface area of the inner surface 137A may be increased by increasing the height H3, this approach is limited by the finite thickness of the calvarial bone 4 at the site of implanting of the ICI. Therefore, the ICI 130 makes it possible to increase area of the surface 137A even when H3 is limited by the thickness of the calvarial bone 4. Preferably, but not obligatorily, H3≥0.5R3. However, this may not always be the case due to the thickness of the calvarial bone at the implantation site of the ICI.

It is noted that although in the embodiments of the ICIs illustrated in the drawing figures, the stimulating/recording electrodes disposed within the current directing mechanisms (except for the reference electrodes, such as for example the reference electrode 91C which is disposed within the current directing mechanism as far away as possible from the inner table 6 in order to minimize pickup of electrical cortical signals) extend all the way to the end of the walls 27 and/or 29 in order to maximize the electrode surface area and to be as close as possible to the inner table 6, this is not obligatory. Rather, in some embodiments of the ICIs, the stimulating/recording electrodes may extend along the walls to a distance smaller than the full height of the walls of the current directing mechanism.

In some embodiments of the ICIs of the present application may also include besides the wall 137, one or more additional walls within the current directing mechanism 135 (such as, for example, walls similar in position and diameter to the walls 27 and 29 of the ICI 100). In such embodiments, the implantation procedure may be modified by suitably modifying the drill bits disclosed hereinabove. For example, after forming the cavity 50 the surgeon may use a cup-like drill bit (not shown) that has an external cup diameter equal to the diameter of the first drill bit 44 (of FIG. 10) to cut an annular cavity (not shown) for accommodating the wall 137. The surgeon may then proceed to use additional cup-like drill bits (not shown) having decreasing cup diameters for forming additional annular recesses (not shown) for accommodation the additional walls included in the multi-walled current directing mechanism of such ICI embodiments.

It is noted that the reference electrode 91C (of the ICIs 90, 100, 110, 120) and the reference electrode 131C of the ICI 130 may be used as a reference electrode during a recording mode of the ICI 90, 100, 110, 120, and 130 and may also be used as a stimulating electrode in a stimulating mode of the ICIs 90, 100, 110, 120 and 130. The ICIs 90, 100, 110, 120, 130 and their components may be made from the materials disclosed in detail hereinabove for the ICI 10.

Figure 23:
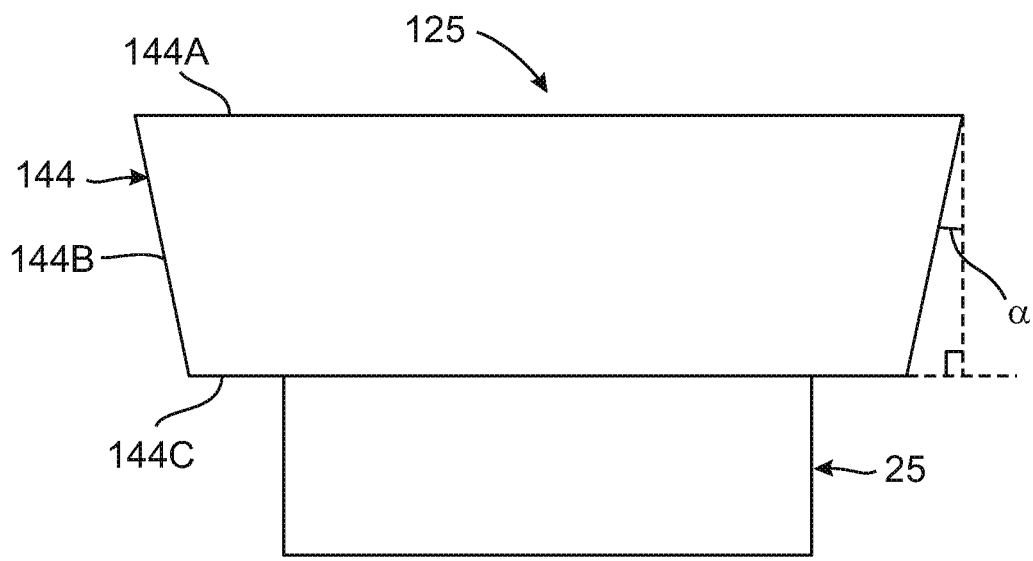
FIG. 23 is a schematic side view illustrating an ICI having a frustoconical sealed compartment, in accordance with some embodiments of the ICIs of the present application.

Reference is now made to FIG. 23 which is a schematic side view illustrating an ICI having a frustoconical sealed compartment, in accordance with some embodiments of the ICIs of the present application. The ICI 125 has a frustoconical sealed compartment 144 and the cylindrical current directing mechanism 25 (of FIGS. 1-9). The sealed compartment 144 has a top part 144A, a bottom part 144C and side walls 144B. The side walls 144B are inclined at an angle α to the top part 144A. Typically, the angle α may be a small angle in the range of 1-15°. The frustoconical shape may assist the insertion of the ICI 125 into the cavity formed in the calvarial bone 4. It is noted that for ICIs with a sealed compartment having a frustoconical shape, the first drill bit 44 may have to be modified to have a frustoconical head (instead of a cylindrical drill head) such a head may be adapted to cut a frustoconical cavity (not shown) instead of the cylindrical cavity 50 (of FIGS. 9-10). The dimensions of such a frustoconical cavity may be equal to or slightly larger than the dimension of the frustoconical sealed compartment 144 to ensure a tight fit of the ICI 125 within the frustoconical cavity.

Figure 24:
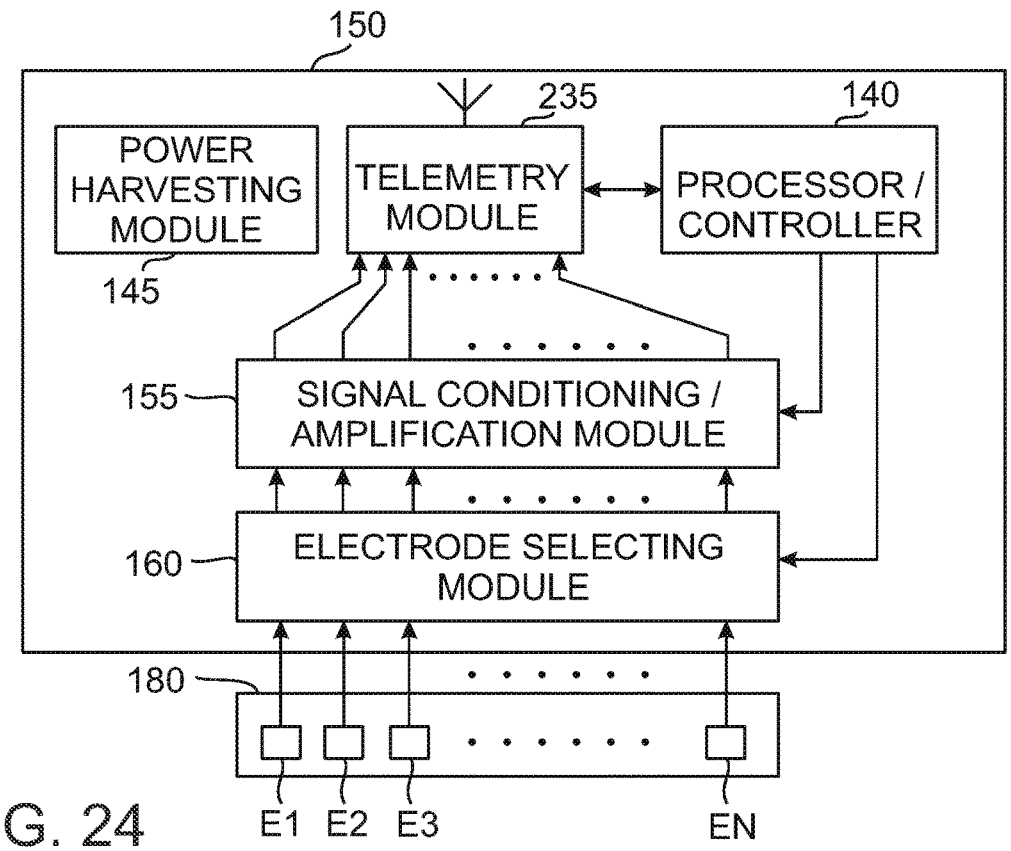
FIG. 24 is a schematic block diagram illustrating some of the components of an ECM usable in the ICIs of the present application, in accordance with some embodiments of the ECMs of the present application.
Figure 25:
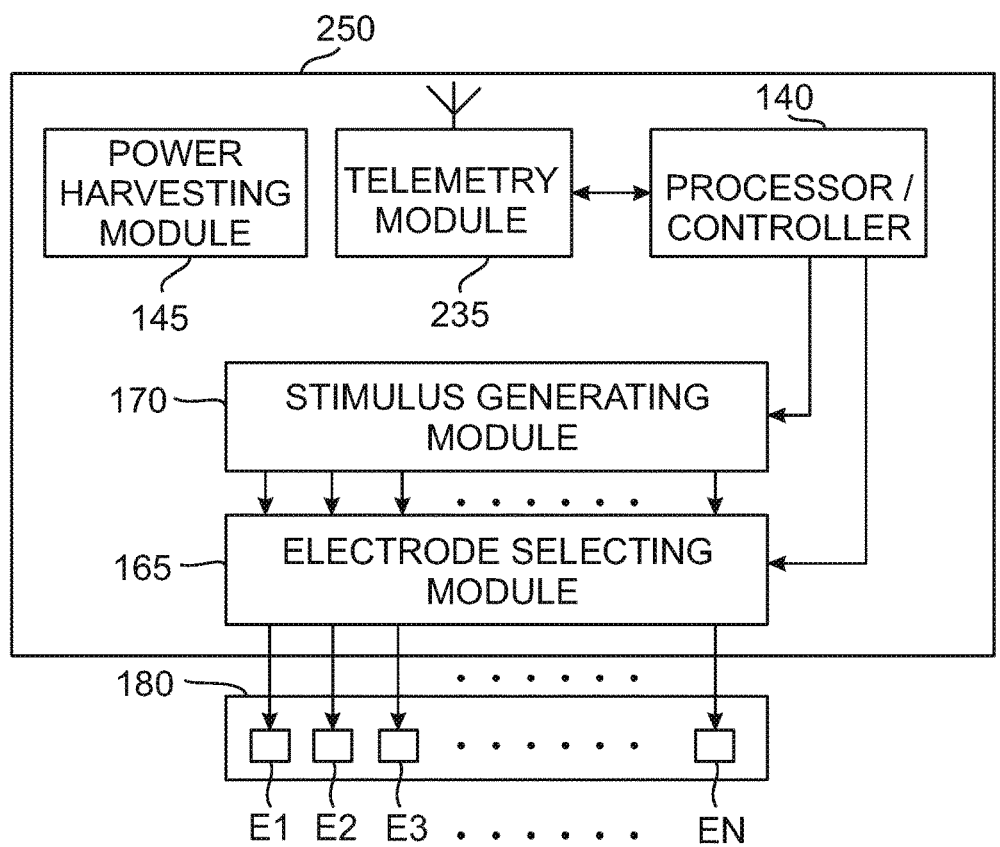
FIG. 25 is a schematic block diagram illustrating some of the components of another ECM usable in the ICIs of the present application, in accordance with some embodiments of the ECMs of the present application.
Figure 26:
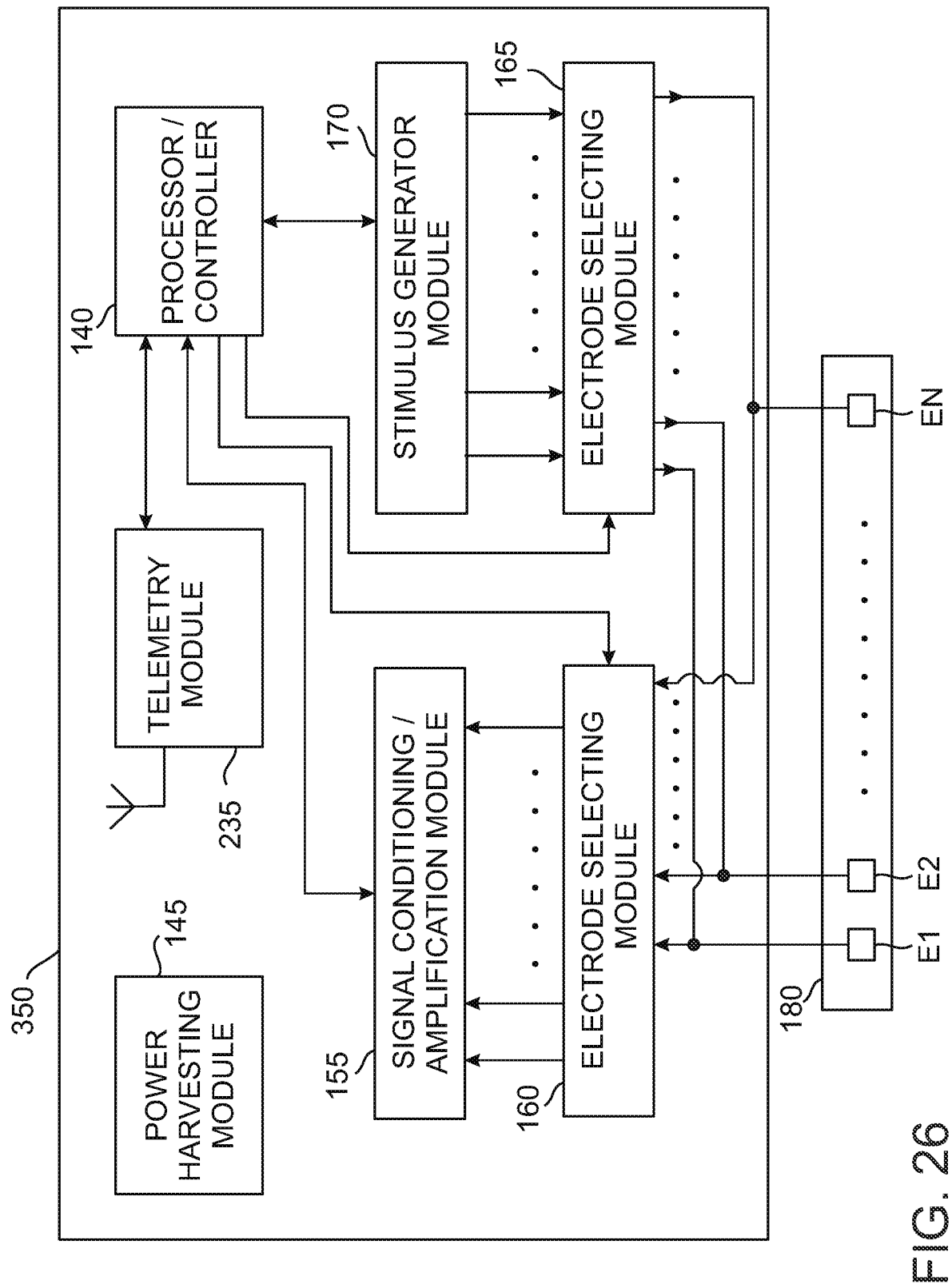
FIG. 26 is a schematic block diagram illustrating some of the components of an ECM usable in the ICIs of the present application, in accordance with some embodiments of the ECMs of the present application.

Reference in now made to FIGS. 24-26. FIG. 24 is a schematic block diagram illustrating some of the components of an ECM usable in the ICIs of the present application, in accordance with some embodiments of the ECMs of the present application. FIG. 25 is a schematic block diagram illustrating some of the components of another ECM usable in the ICIs of the present application, in accordance with some embodiments of the ECMs of the present application. FIG. 26 is a schematic block diagram illustrating some of the components of an ECM usable in the ICIs of the present application, in accordance with some embodiments of the ECMs of the present application.

Turning to FIG. 24, the ECM 150 is illustrated as electrically connected to a plurality of electrodes 180. The plurality of electrode 180 may include N electrodes E1, E2, E3, . . . , EN, wherein N is an integer number that may typically (but not obligatorily) be in the range of N=2-50. The plurality of electrodes 180 may include stimulating/recording electrodes, reference electrodes and ground (return) electrodes as disclosed hereinabove and illustrated in the drawing figures. The ECM 150 may include an electrode selecting module 160, a signal conditioning/amplification module 155, a telemetry module 235, a power harvesting module 145 and a processor/controller 140. The above mentioned values of N should therefore be considered as typical and non-limiting and the value of N may vary depending, inter alia on the required resolution, the technology of producing the electrodes, the surface area of the electrodes, the ability of the ECM 150 to sense and transmit (and multiplex) N channels, the computational power of the processor/controller 140 and other engineering and manufacturing considerations.

Each of the N electrodes E1, E2, E3, . . . , EN, may be electrically operatively connected to the electrode selecting module 160, that may select from which electrode(s) or electrode combination electrical brain signals are going to be sensed. The electrode selecting module 160 is suitably connected to the processor/controller 140 that controls the operation thereof. The electrode selecting module 160 may be operatively coupled to the signal conditioning/amplification module 155 and may output the signals from the selected electrodes (or electrode pairs in differential recording) to the signal conditioning/amplification module 155 that may condition (such as, for example by suitably filtering the signals) and amplify the signals received from the electrodes selected by the electrode selecting module 160.

The signal conditioning/amplification module 155 may be suitably connected to the processor/controller 140 which may control the operation thereof to determine and or change and/or select the type of desired signal conditioning depending on the specific application. In some embodiments in which the ECM 150 is designed or programmed to perform only a defined type of signal conditioning and amplification, the signal conditioning/amplification module 155 may be "hard wired" to perform a fixed and unchanging type of conditioning/amplification but some parameters (such as, for example, the amplification gain and the filtering parameters) may be dynamically controlled by the processor/controller 140 based on the results of processing of the signals which may monitor the SNR and noise characteristics to control such parameters.

In some embodiments, the communication between the processor/controller 140 and other modules (such as, for example, the electrode selecting module 160 and the signal conditioning/amplification module 155 may be bidirectional communication lines, to enable these modules to send device status signals, error signals and possibly clock synchronization signals to the processor/controller 140.

The conditioning performed by the signal conditioning/amplification module 155 may include signal filtering such as, for example high pass filtering, notch filtering, low pass filtering or any other signal conditioning types required by specific applications. The conditioned/amplified signals may then be (optionally) stored in the memory of the processor/controller 140 and/or communicated to the telemetry module 235 for being transmitted to an external telemetry unit (not shown in FIG. 24) for further processing.

The telemetry module 235 may be configured to transmit either the (optionally processed) analog signals to an external telemetry unit or to digitize the signals and transmit digitized data to an external telemetry unit. The transmitter signals or data may have to be multiplexed for transmitting as disclosed hereinafter with respect to FIG. 27 hereinafter. The power harvesting module 145 may be any suitable power harvesting unit for providing harvested energy to any components or modules that need to be energized. The power harvesting module 145 may be implemented, for example, as an electromagnetic induction based power harvesting module attachable to an implanted induction coil (such as any of the induction coils 55 disclosed hereinabove) but may also be an ultrasonic energy harvesting unit including an implanted piezoelectric transducer that generates electricity when receiving energy from an external ultrasonic beam directed towards the implanted piezoelectric transducer. The power harvesting module 145 may also be an electromagnetic radiation harvesting unit that includes an implanted antenna configured to receive electromagnetic waves transmitted from an external power transmitter.

All suitable power harvesting methods known in the art that may provide sufficient energy for operating the systems disclosed herein may be implemented in the systems and ICIs of the present application. If the power harvesting module 145 is not an induction coil based power harvesting module, the induction coil 55 need not be included in any of the ICIs and may be replaced by other components such as, for example a suitable piezo electric device (not shown) in the case of the power harvesting module 145 being an ultrasonic energy harvesting module.

It is noted that in all the drawing figures of the present application, the connections of the power harvesting unit(s) to all the modules and/or components in need of power are not shown in detail for the sake of clarity of illustration.

Thus, the ECM 150 may be used for sensing/recording of brain signals using any of the ICIs disclosed hereinabove, and for wirelessly sending the sensed recorded signals or data to an external device for further processing.

Turning now to FIG. 25, the ECM 250 is connected to the plurality of electrodes 180. The ECM 250 may include an electrode selecting module 165, a stimulus generator module 170, a telemetry module 235, a power harvesting module 145 and a processor controller 140.

Each of the N electrodes E1, E2, E3, . . . , EN, may be electrically operatively connected to the electrode selecting module 165, that may select to which electrode(s) or electrode combinations stimulating signals are going to be delivered by the stimulus generator module 170 that is operatively connected to the electrode selecting module 165. The electrode selecting module 160 is suitably connected to the processor/controller 140 that may control the operation thereof. The stimulus generator module 170 may also be suitably operatively connected to the processor/controller 140, for controlling the operation of the stimulus generator module 170. The processor/controller 140 may control the stimuli delivered to the electrodes selected from the plurality of electrodes 180 autonomously by executing an application software program operating on the processor/controller 140. Alternatively, and/or additionally, the processor/controller 140 may receive external instructions and/or control signals from an external control unit or module (not shown in FIG. 25) that may be communicating with the telemetry module 235 that is suitably operatively connected to the processor/controller 140. Such telemetrically received control signals may control or modulate or reprogram the operation of the processor/controller 140 and may be used to change or modulate or stop or begin the stimulation regime, through the plurality of electrodes 180. The telemetry module 235 may also be used for transmitting status signals and/or error signals from the processor/controller 140 to the external telemetry module or unit.

The power harvesting module 145 may be any suitable power harvesting unit as disclosed in detail hereinabove for providing harvested energy to any components or modules of the system 300 that need to be energized.

Thus, the ECM 250 may be used to autonomously, or in interaction with an external control unit (not shown), deliver stimuli to the brain through any of the stimulating electrodes and/or the stimulating/recording electrodes of any of the ICIs disclosed hereinabove, and for wirelessly interacting with an external device (such as any type of telemetrically capable controller device) for controlling or modulating the parameters of any stimuli delivered to selected electrodes or selected electrode combinations. The parameters controlled by the ECM 250 may include, inter alia, the type of stimulating signals, the electrode(s) through which stimuli are delivered, the stimulus amplitude, the stimulus shape and type such as for example the signal pulse parameters (monopolar pulses, bipolar pulses, monophasic pulses, biphasic pulses) the timing or frequency of stimulation, or any other type of stimulation parameter.

Turning now to FIG. 26, the ECM 350 may be capable of sensing and/or recording electrical brain signals and also of stimulating the brain as disclosed hereinabove. The ECM 350 may be suitably electrically connected to the plurality of electrodes 180 as disclosed hereinabove. The ECM 350 may include the power harvesting unit 145, the telemetry module 235, the processor/controller 140, the signal conditioning/amplification module 155, the stimulus generator module 170, and the electrode selecting modules 160 and 165.

The processor/controller 140 may be operatively and bidirectionally connected to each of the telemetry module 235, the signal conditioning/amplification module 155, the stimulus generator module 170, and the electrode selecting modules 160 and 165 for controlling their operation as disclosed hereinabove.

Each of the N electrodes E1, E2, . . . EN, may be electrically coupled to the signal conditioning/amplification module 155 and the stimulus generator module 170 through the electrode selecting modules 160 and 165, respectively, as illustrated in FIG. 26. Therefore, each of the selected electrodes or electrode combinations may be used for sensing/recording brain electrical signals and also for stimulating one or more brain regions (typically, but not obligatorily, cortical regions).

In some embodiments, the ECM 350 may be operated as a closed loop BCI system. In such a system, the electrical signals sensed in the brain by the selected electrode(s) may be processed by the processor/controller 140 to detect an indication of a physiological and/or neurological and/or neuropsychiatric state of the brain and to automatically and/or autonomously deliver to the brain a selected stimulation regime responsive to the detection of such an indication.

In other embodiments, the system may sense and condition/amplify signals received from one or more brain regions as disclosed in detail with respect to the ECM 250 of FIG. 25. The ECM 350 may then use the telemetry module 235 to telemetrically transmit the signals to an external control unit (not shown in FIG. 26) for processing by a processor/controller (not shown) included by such an external control unit that may have a higher computational power as compared to the processor/controller 140. The external control unit may perform the processing of the telemetrically received signals or data and may detect the indication of the physiological and/or neurological and/or neuropsychiatric state of the brain and responsive to such detection may telemetrically send appropriate control signals to the processor/controller 140. Upon receiving the appropriate control signals, the processor/controller 140 may initiate an appropriate stimulation regime for stimulating one or more brain regions to modulate the state of the brain in such a way that may result in changing or therapeutically treating the detected physiological and/or neurological and/or neuropsychiatric state of the brain.

In an example, in a specific application to therapeutically treat mood disorders such as, for example, depression, any of the ICIs disclosed in the present application may be implanted for sensing electrical activity in the dorsolateral prefrontal cortex (DLPFC) to detect an indication that the patient is in a depressed state (such as, for example, modulation of high gamma band power/amplitude changes may be monitored by sensing electrical brain signals in the DLPFC). When the power in the higher frequencies of the gamma band is below an empirically determined threshold value, this may be an indication of a depressed state of the patient and the system may initiate stimulation of some target brain regions, such as, for example, the DLPFC, other cortical regions, the subgenual cingulate region (Brodmann area 25), the ventral capsule/ventral striatum (VC/VS), the Nucleus Accumbens, the Lateral habenula, the Ventral caudate nucleus (VCN), the Inferior thalamic peduncle, and/or any combination of the above brain regions.

Stimulation of such deep brain targets may be performed by the ICIs disclosed herein by using a Frequency Interference (IF) stimulation method similar to the TFIS method described by Grossman et al. with all the advantages conferred by the use of intra-calvarial electrodes as described in detail in the present application. Upon detection of such an indication (decreasing of the high frequency gamma band power below a threshold), the ICI may also directly stimulate any some cortical regions (such as, for example, the DLPFC or other cortical regions) to treat the depression.

In another exemplary application, the ICIs of the present application may be used for enhancing cognition (In patients having neurodegenerative disorders, neuropsychiatric disorder and/or psychiatric disorders, or in in normal subjects which do not suffer from any neurodegenerative disorders or neuropsychiatric disorder or psychiatric disorders) by sensing simultaneously in the DLPFC and the temporo-parietal cortex (TPC) and processing the sensed signals to detect an indication of enhanced phase locking between signals sensed in the DLPFC and the TPC in the beta frequency band. Upon detection of the indication, the system 400 may stimulate directly the DLPFC and the stimulation may result in enhanced cognitive performance of the user/patient.

In such a way, the ICIs of the present application by using such closed loop BCI methods, may be used to treat many types of disorders, such as, for example, neurodegenerative disorders, neuropsychiatric disorder and/or psychiatric disorders, including, for example, epilepsy, traumatic brain injury (TBI), depression, obsessive-compulsive disorder (OCD), ADHD, attention deficit disorder (ADD), eating disorders including bulimia and anorexia, obesity, and other types of disorders.

Figure 27:
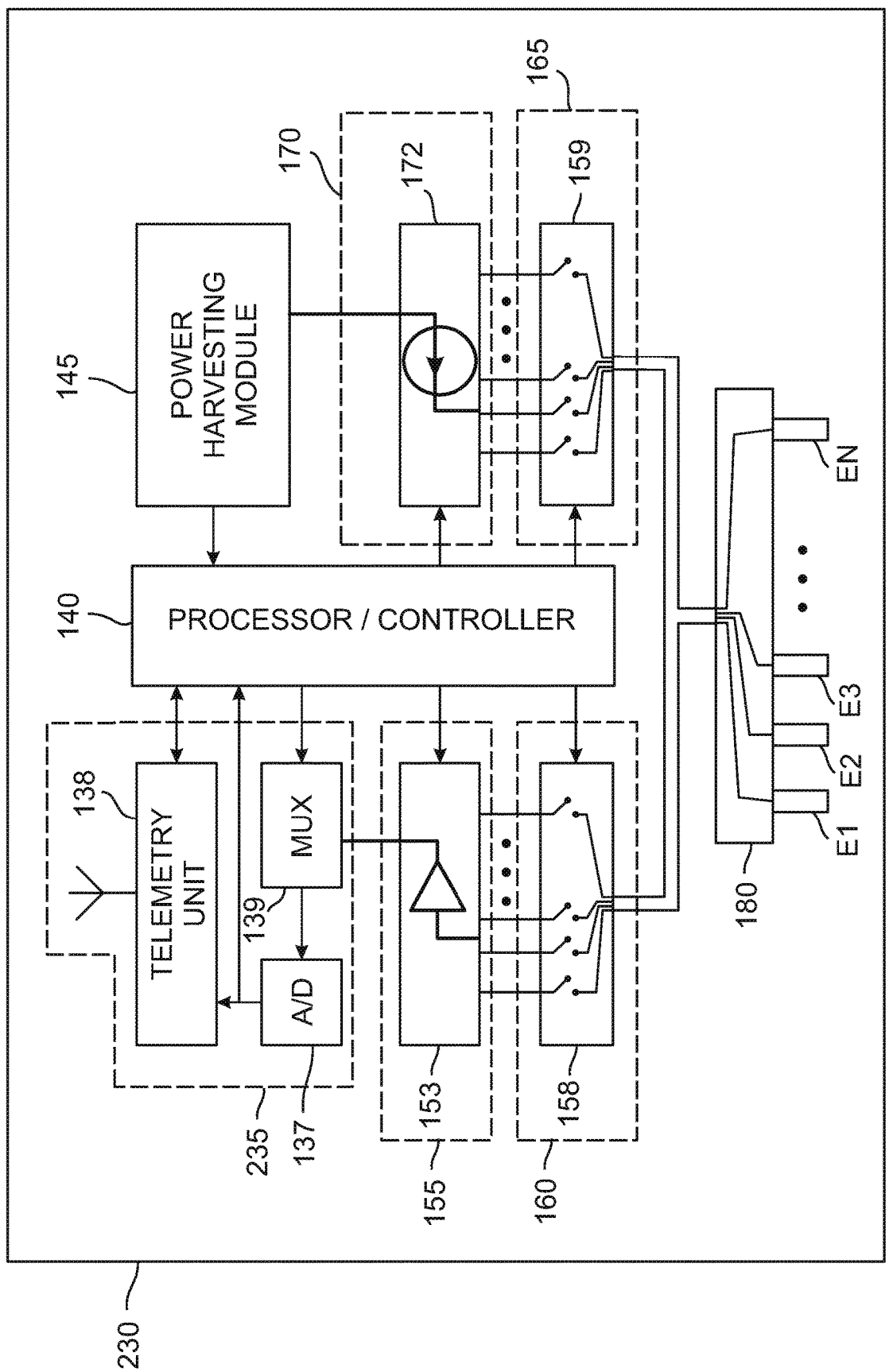
FIG. 27 is a schematic block diagram illustrating an exemplary ECM for sensing/recording brain electrical signals and for stimulating one or more regions of the brain, in accordance with some embodiments of the ECMs of the present application.

Reference is now made to FIG. 27, which is a schematic block diagram illustrating an exemplary ECM for sensing/recording brain electrical signals and for stimulating one or more regions of the brain, in accordance with some embodiments of the ECMs of the present application.

The ECM 230 is illustrated as connected to the plurality of electrodes 180. Any of the electrodes included in any of the ICIs disclosed in the present application may be used. The electrodes E1, E2, E3, . . . , EN of the plurality of electrodes 180 may be suitably electrically coupled to the electrode selecting modules 160 and 165 as illustrated in FIG. 27. In the specific embodiment illustrated in FIG. 27, the electrode selecting unit 160 may be implemented as a first solid state switching device 158, and the electrode selecting unit 165 may be implemented as a second solid state switching device 159. The signal conditioning/amplification module 155 is implemented as a solid state multi-channel amplifier 153. The stimulus generator module 170 is implemented as a solid state multi-channel stimulator 172.

The telemetry module 235 may be implemented by a telemetry unit 138 a multiplexer (MUX) 139 and an analog to digital converter (A/D) 137.

The multiple amplified signals outputted from the multi-channel amplifier 153 may be multiplexed by the MUX 139, digitized by the A/D 137 and fed to the telemetry unit 138 to be transmitted to an external telemetry receiver as disclosed hereinabove. The multiplexing may be implemented as any type of multiplexing method known in the art, including but not limited to time division multiplexing, and frequency division multiplexing. The transmitted signals may be suitably decoded by the external telemetry unit (not shown) and the data may be processed by a processor/controller (not shown in FIG. 27) coupled to the external telemetry unit or module. The external processor/controller may detect an indication of a physiological and/or neurological and/or neuropsychiatric state of the brain as disclosed in detail hereinabove and may telemetrically control the processor/controller 140 to initiate stimulation by delivering suitable stimulating signals to selected electrodes of the plurality of electrodes 180.

It is noted that the type of stimulation generated by the multi-channel stimulator 172 may be either direct stimulation of selected cortical regions, and/or a frequency interference (FI) type of stimulation at two different high frequencies as disclosed in detail by Grossman et al. This type of intra-calvarial FI stimulation may enable stimulation of selected deep brain structures and may benefit from the intra-cranial placement of the electrodes which may advantageously result in improved stability and repeatability of the stimulation due to the closer distance of the electrodes of the plurality of electrodes 180 to the surface of the brain and the elimination of the above mentioned problems of using external EEG type electrodes as disclosed by Grossman et al. Moreover, the use of the intra-calvarial electrodes disclosed in the present application may require reduced stimulation current amplitudes (or intensities) that may advantageously save energy stored of in the implanted power harvesting modules of the ICIs of the present application. The reduced stimulation amplitudes may result, inter alia, due to the smaller electrical impedance of the inner table 6 in stimulation by intra-calvarial electrodes as compared to the much higher electrical impedance of the entire thickness of the scalp and the calvarial bone interposed between the brain and the stimulating electrodes disclosed by Grossman et al.

Furthermore, due to the ability to select many types of differently spaced and differently positioned electrode pairs selectable for stimulation by the solid state switches 158 and 159, the flexibility repeatability and finesse of the focal brain region stimulation using intra-calvarial electrode arrays may be significantly enhanced.

Figure 28:
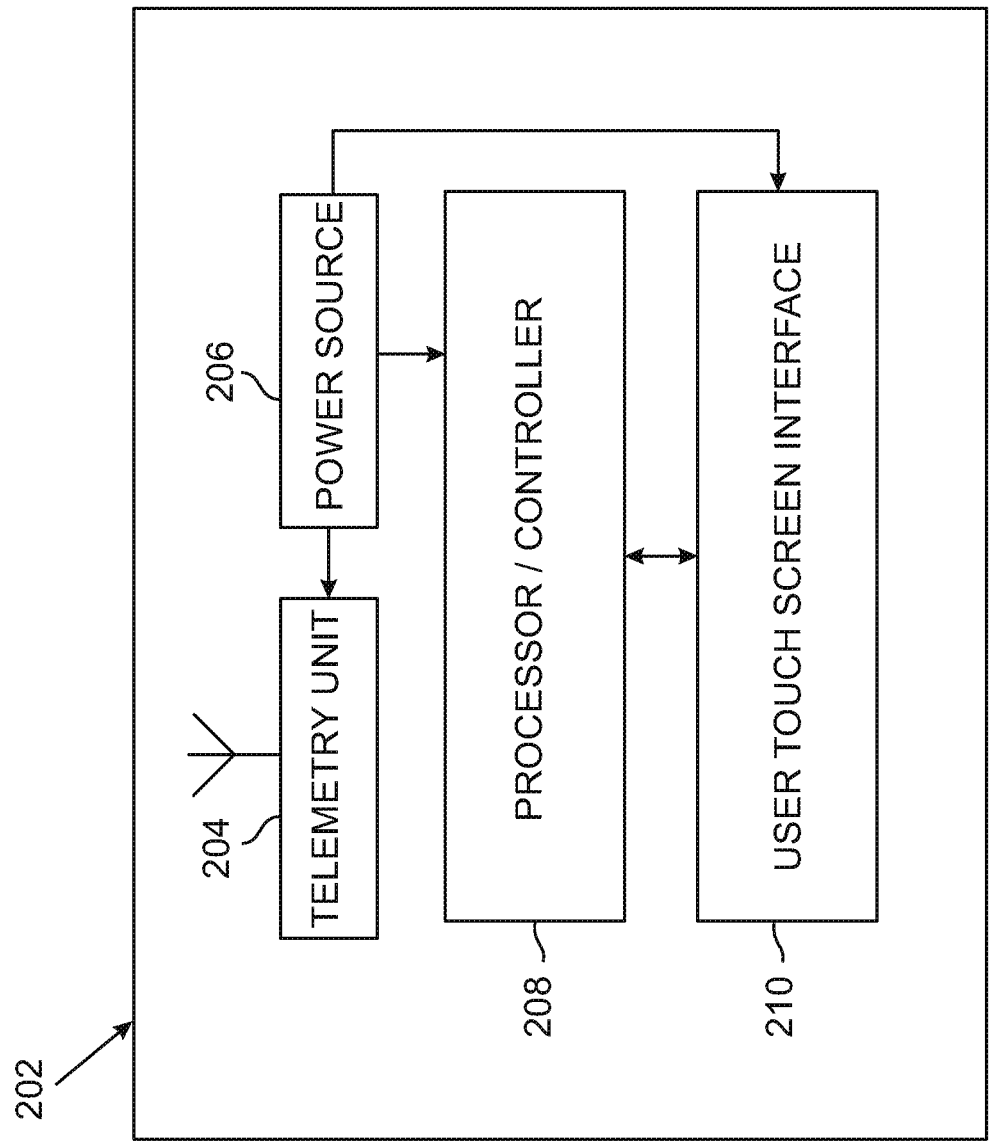
FIG. 28 is a schematic functional block diagram illustrating some components devices of a hand held or wearable or portable device usable with the ICIs of the present application.
Figure 29:
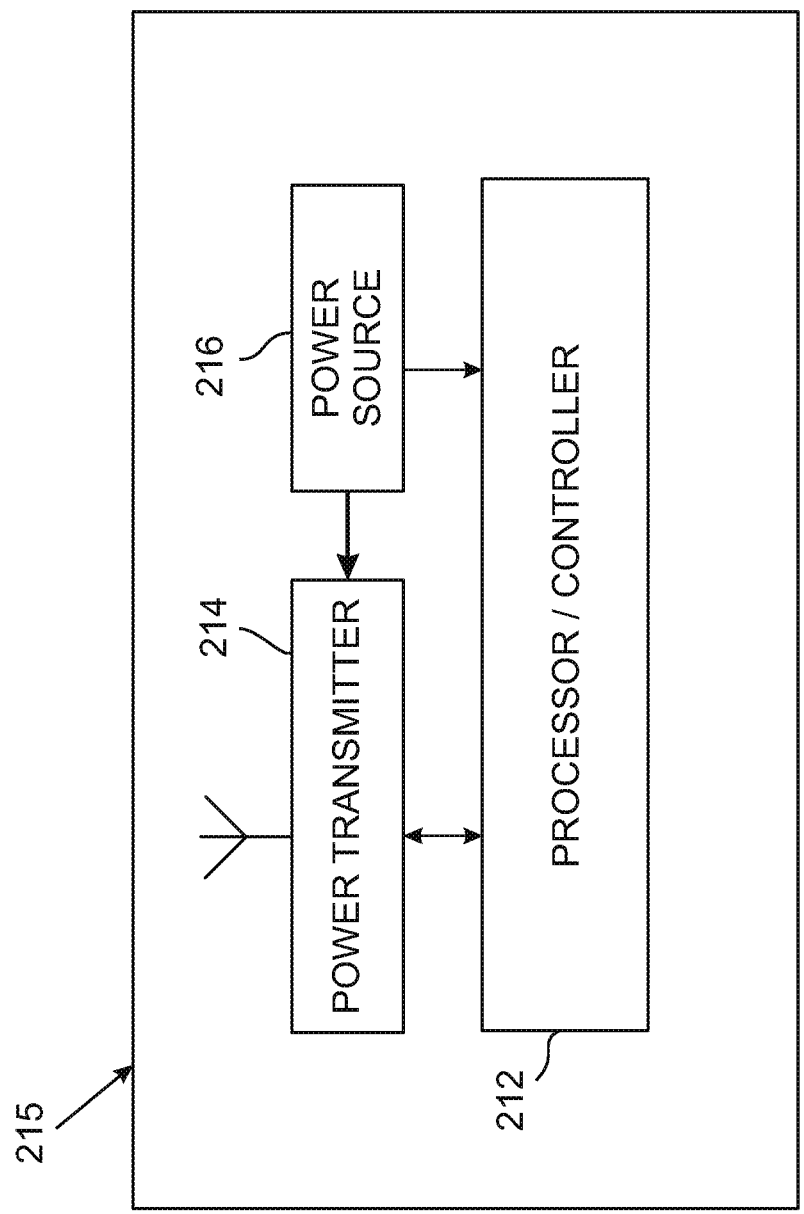
FIG. 29 is a schematic block diagram illustrating some components of an energizing device usable for providing power to some of the ICIs of the present applications.

Reference is now made to FIGS. 28-29. FIG. 28 is a schematic functional block diagram illustrating some components devices of a hand held or wearable or portable device usable with the ICIs of the present application. FIG. 29 is a schematic block diagram illustrating some components of an energizing device usable for providing power to some of the ICIs of the present applications.

Turning to FIG. 28, in accordance with some embodiments, an external controlling/processing device 202 may be used to communicate with any of the ICIs of the present application. The device 202 may be a mobile and/or portable and/or hand held device, and/or wearable device such as, for example, a mobile (cellular) telephone or smartphone, a pablet, a tablet, a laptop computer a notebook or a wearable virtual reality (VR) headset, or a wearable augmented reality (AR) headset. The device 202 may include a processor/controller 208 (such as, for example the processor included in a cellular telephone). The device 202 may also include a power source 206 (such as, for example the rechargeable lithium battery of a laptop or a cellular telephone). The device 202 may also include a telemetry unit 204 (such as, for example, the cellular transmitter of the smartphone or cellular telephone or WiFi circuitry of a laptop computer) that is suitably connected to and controlled by the processor/controller 208. The device 202 may also include a user touch screen interface 210 (such as, for example, the touch sensitive display screen of a cellular telephone or smartphone or a laptop touch sensitive screen) that enables the user to interact with any application operating on the processor(s) included in such mobile cellular telephones).

It is noted that the external controlling processing device 202, is not limited to mobile phones or smartphone but may also be implemented as any device having wireless communicating capabilities, processing power and a user interface (physical and/or virtual), including for example, a laptop or other computer, a notebook, a pablet, a virtual reality (VR) headset, such as, for example, virtual reality goggles, VR eyeglasses, augmented reality (AR) headsets, or any other device enabling the user to interact with a virtual or physical user interface of any type.

In operation, a software program or mobile application may be installed on the smartphone that may wirelessly receive signals and or data from any of the ICIs of the present application and may process the received data to detect an indication of a change in the state of the user in which the ICIs are implanted, as disclosed hereinabove. The processor(s) of the device 202 may telemetrically send control signals to the telemetry module 235 of any of the ICIs being used. When the control signals are received by the processor/controller 140 of the ECM (such as, for example, any of the ECMs 28, 98, 108, 150, 230, 250 and 350) they may initiate a stimulation regime of one or more brain regions of the user/patient by controlling the stimulus generator module 170 and/or the electrode selecting module 165 of the ECMs 230, 250 and 350.

Furthermore, the inclusion of the device 202, may enable further interactions of the user/patient with the ICIs by using the touch screen user interface 210 for displaying data or processed date on the screen representing the status of the system, the parameters of stimulation and other information about the status and operational state and/or operational history of the system. In some embodiments the user or the patient may be able to feed data or control instructions to the touch screen interface 210, for changing and/or modulating, and/or stopping, and or initiating the operation of the ICI.

It is noted that the user-interface of the portable and or mobile and/or wearable devices disclosed hereinabove may be any type of physical interface (such as, for example, a keyboard, a touch-screen) but may also be any other type of interface, such as a graphic user interface (GUI), a virtual GUI, or any other type of suitable user interface.

Turning now to FIG. 29, the power transmitting device 215 may be used with any of the ICIs disclosed in the present application for providing power to the power harvesting modules 145 of any of the ICIs. The device 215 may be a hand held or a portable device. The device 215 may include a power source 216, such as, for example, a battery or electrochemical cell or rechargeable battery or any other suitable power source. The power source 216 may suitably connected to a processor/controller 212 and to a power transmitter 214. For example, if the power harvesting module 145 used by the system is connected to an induction coil (such as any of the different induction coils disclosed in the present application), the power transmitter 214 may be configured to include an external induction coil (schematically represented by the antenna symbol illustrated on the power transmitter 214) that may be placed near or in close proximity to the implanted induction coil under the scalp of the user/patient to effectively transmit electrical power to the implanted induction coil.

If the inductively transmitted power induces in the inductance coil 55 an alternating current (AC), the AC may be rectified by suitable electronic circuitry (not shown) in the power harvesting system and may be stored in any suitable type of charge storage device (such as, for example, a rechargeable electrochemical cell or a super-capacitor) included in the power harvesting module of the ICI (such as, for example the power harvesting module 145) and may be used for powering the components of the ICI.

It is noted that the device 202 and the power transmitting device 215, need not obligatorily be separate devices. For example, the components and functionalities of the device 202 and of the power transmitting device 215 may be combined in a single device (not shown) such that the combined device may be used for controlling the ICI(s), storing and/or processing data received from the ICI(s), transmitting or offloading stored data and/or stored processed data into other devices (such as, for example, computers, laptops or servers, in communication with such a combined device) and also for transmitting power to the ICI(s). Preferably (but not obligatorily), such a combined device may be a hand held compact device so that it may be easily handled by the patient to provide power to the ICI(s). Alternatively, the device may include a hand held device (such as, for example, the device 67 and the induction coil 60 that may be connected to and controlled by a computer 66 (of FIG. 16).

It is noted that the all the processor/controllers 140, 208 and 212 disclosed hereinabove may include solid state memory as an integrated part thereof and/or may be suitably electrically coupled to external memory (not shown in any of the drawing figures for the sake of clarity of illustration) that may be included in any of the ECMs of the ICIs of the present application. Such memory may be of any type of memory known in the art, such as, for example, read only memory (ROM), random access memory (RAM), electrically programmable read only memory (EPROM), electrically erasable programmable read only memory (EEPROM), Flash memory devices of any type known in the art, optical memory, magnetic storage devices and any combinations thereof.

Returning briefly to FIGS. 24-26, by suitably using electrode selecting circuitry (such as, for example the electrode selecting modules 160 and 165 of FIGS. 24-27), it may be possible to selectively simultaneously combine one or more of the electrodes E1, E2, E3 . . . EN to form a first subset of electrodes and to combine one or more electrodes from the remaining electrodes to form a second subset of electrodes.

The first and second electrode subsets may then be used for stimulating by passing current between the first subset of electrodes and the second subset of electrodes. The first and second electrode subsets may also be used for sensing/recording the voltage difference sensed between the electrodes of the first subset and the electrode(s) of the second subset. Therefore, one of the advantages of using the plurality of electrodes 180 in combination with electrode selecting modules is the high degree flexibility in performing recording and stimulation between selected combined electrode subsets and the ability to vary the location of the selected subsets on the electrode array and also to control the combined surface area of the electrode subsets.

It is noted that the ECMs disclosed herein may allow sensing/recording to be performed in any suitable electrodes or electrode subsets. For example, in the ICI 10, recording of cortical signals may be differentially performed between any suitable combinations of electrode pairs including the pairs 30A-30E, 30B-30E, 30C-30E and 30D-30E and any combination of such electrode pairs. Similarly, the ECMs disclosed herein may allow sensing/recording to be performed in any suitable electrodes or electrode subsets. For example, in the ICI 10, stimulating currents may be passed between any suitable combinations of electrodes such as, for example, passing current between the ground electrode 30F and any combinations of the electrodes 30A, 30B, 30C, 30D and 30E. This may allow fine control of the delivered current intensity.

It is noted that different embodiments of the ICIs of the present application may have different functionalities. Some ICIs may be stimulating only ICIs and may not be able to perform sensing/recording of brain signals. For example an ICI including the ECM 250 (of FIG. 25) may be configured for performing stimulation only and for receiving control signals from an external device (such as, for example, the device 202 of FIG. 28).

Some other embodiments of the ICIs may be sensing/recording only ICIs. For example, ICIs including the ECM 150 of FIG. 24 may only be capable of sensing/recording cortical signals. Such embodiments may directly wirelessly transmit the sensed signals through the telemetry module 235 to an external processing device (such as, for example the device 202 of FIG. 28) for further processing. Alternatively, such ICIs may sense such cortical signals and may store the sensed signals in a memory (not shown) of the processor/controller 140 for transmitting to an external processing device (such as, for example the device 202 of FIG. 28). Alternatively or additionally, some such sensing/recording only embodiments may be programmed to process the sensed and/or recorded signal to obtain processed data. The processed data may include indications of a physiological and/or neurological and/or neuropsychiatric state of the patient, as disclosed in detail hereinabove. For example, supra-threshold modulation of power/amplitude of gamma band signals that may indicate that a patient is in a depressed state. Such embodiments may wirelessly transmit the sensed/recorded signals and/or the processed signal data to an external processing device (such as, for example, the device 202 of FIG. 28), where the signals may be further processed if necessary and the data may be used by the external device to wirelessly send stimulation control signals to other ICIs implanted in the skull of the same patient for initiating brain stimulation if necessary (see for examples the multi-ICI systems of FIGS. 30-32, hereinbelow).

Some other embodiments may have both sensing/recording and stimulating capabilities, such as, for example ICIs having the ECM 350 of FIG. 26. Such ICI embodiments may have all the capabilities of the sensing/recording only ICIS and the stimulating only IC. If such ICI embodiment do not have substantial processing power, they may sense/record the signals and/or partially process the signals to generate digital data and then wirelessly transmit the signals and or the data to an external device (such as, for example the external device 202) for further processing of the signals/data to detect the indications disclosed hereinabove. The device 202 may then wirelessly send stimulation control signals to the same ICI from which the signals/data were received to initiate therapeutic stimulation (or, alternatively may send the stimulation control signals to one or more stimulating ICIs implanted in the skull of the same patient).

It is noted that if the processor/controller 140 of the ECM 350 has sufficient processing power, all of the processing steps of the sensed/recorded signals for detecting the indications of the physiological and/or neurological, and/or neuropsychiatric state of the patient may be locally performed by the processor/controller 140 of the ECM 350. In such an embodiment, the ICI may operate autonomously and may not depend on communication with an external device for operation as all the sensing/recording, processing detecting the indication and delivering stimulation may be automatically and autonomously performed by the ICI. However, the external device 202 may still be used to wirelessly transmit programming instructions and/or modify some program parameters for any sensing/recording, processing and/or stimulation control software modules operating the processor/controller 140 to the ICI. The device 202 may also be used to wirelessly receive from the ICI diagnostic data and or historical data of the operation of the ICI usable for periodic patient monitoring and follow-up.

Beyond a single implant configuration, the present application also envisions and contemplates the implantation and use of multiple implants that may also have unique capabilities. First, more than one ICI may be implanted at different locations in the same skull. This may enable stimulation or inhibition of multiple brain regions to augment or further tailor a functional effect. Specific examples may include stimulating multiple nodes of a functional network (e.g. for the attentional network both parietal lobe and frontal lobe sites may be concurrently stimulated).

Alternatively, different brain networks may be co-stimulated for complimentary effects. As an example, both attentional and motor networks may be stimulated to enhance the performance in a professional athlete. An embodiment of the methods for stimulating multiple brain regions may combine both neuro-modulation regimes that stimulate one region and inhibit another region to create a tailored functional experience. As an example of such embodiments of the present application, the dorsolateral prefrontal cortex (DLPFC) may be stimulated while prefrontal inhibitory regions may be inhibited to globally enhance attention and focus.

Figure 30:
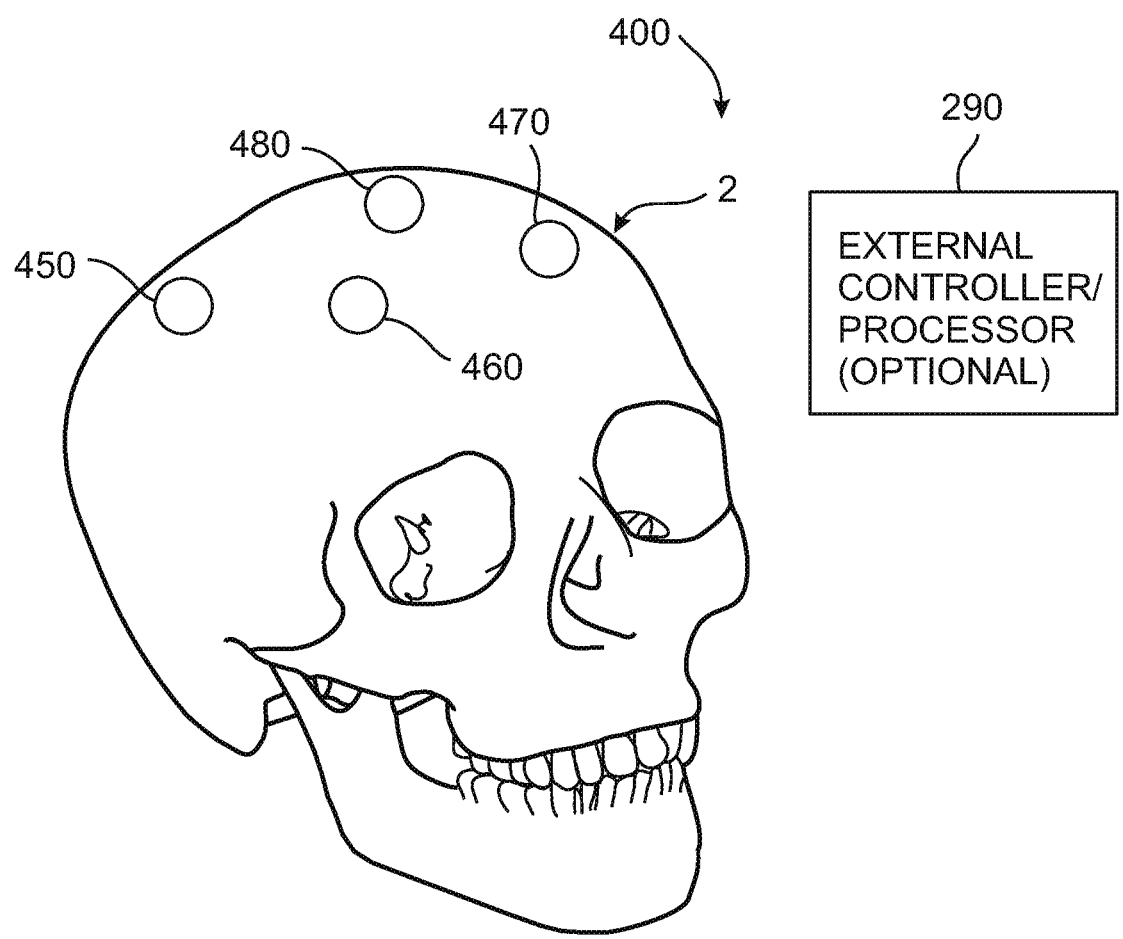
FIG. 30 is a schematic isometric view illustrating an ICI system including four ICIs implanted in the skull of a patient in accordance with some embodiments of the ICI systems of the present application.
Figure 31:
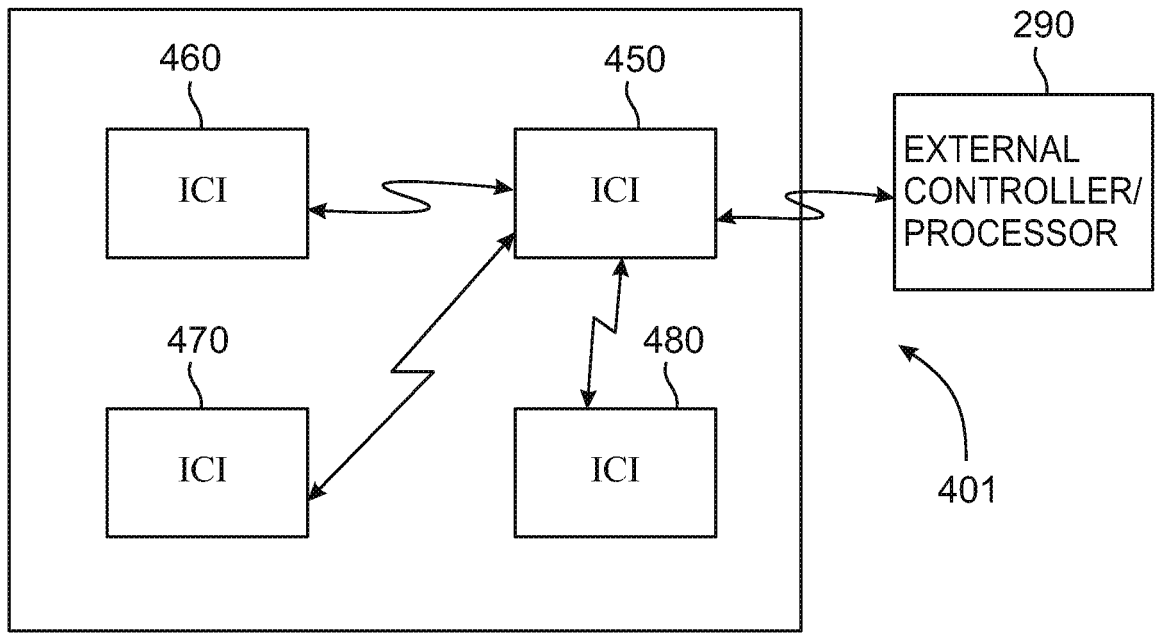
FIG. 31 is a schematic functional block diagram illustrating the communication scheme of a first configuration of the ICI system components of FIG. 30, in accordance with some embodiments of the ICI systems of the present application.
Figure 32:
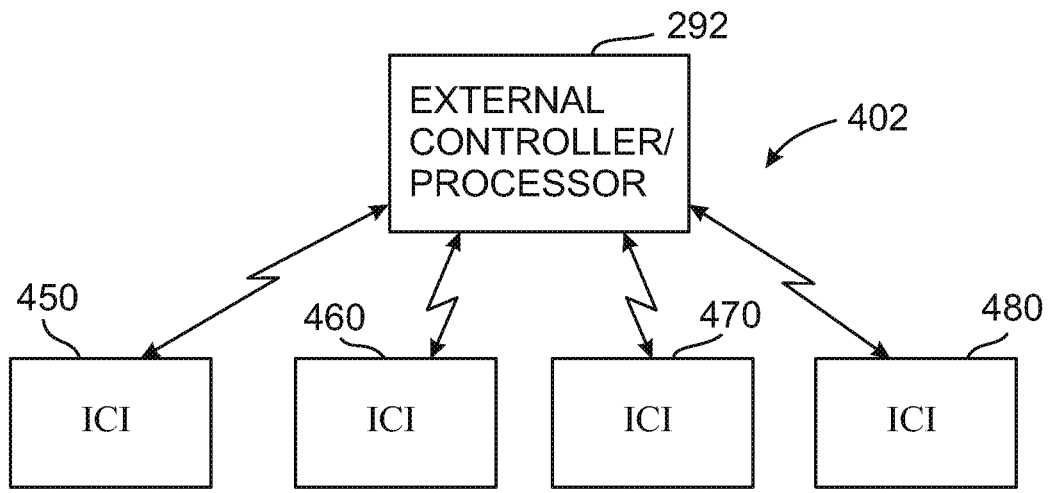
FIG. 32 is a schematic functional block diagram illustrating the communication scheme of a second configuration of the ICI system components of FIG. 30, in accordance with some embodiments of the ICI systems of the present application.

Reference is now made to FIGS. 30-32. FIG. 30 is a schematic isometric view illustrating an ICI system including four ICIs implanted in the skull of a patient in accordance with some embodiments of the ICI systems of the present application. FIG. 31 is a schematic functional block diagram illustrating the communication scheme of a first configuration of the ICI system components of FIG. 30, in accordance with some embodiments of the ICI systems of the present application. FIG. 32 is a schematic functional block diagram illustrating the communication scheme of a second configuration of the ICI system components of FIG. 30, in accordance with some embodiments of the ICI systems of the present application.

Turning to FIG. 30, the ICI system 400 may include four ICIs 450, 460, 470 and 480, and an (optional) external controller/processor 290. The ICIs 450, 460, 470 and 480 may be implemented as any of the ICIs disclosed and illustrated in the present application. In some embodiments of the system, all the ICIs 450, 460, 470 and 480 may be of the same type. In accordance with some other embodiments of the system the ICIs 450, 460, 470 and 480 may be of different types (in a non-limiting example, the ICIs 450 and 480 may be of the type illustrated in FIG. 12 and the ICIs 460 and 470 may be of the type illustrated in FIG. 21). However, it is noted that any combination of any of the types of ICIs disclosed in the present application may be used in the system 400.

The external processor/controller 290 may be any external device positioned outside the body of the patient that has wireless communication capabilities and signal and/or data processing capabilities. For example, the controller/processor 290 may be implemented as the device 202 of FIG. 28 or as the power transmitting device 215 of FIG. 29 or as the combine device including power transmitting components and communication and processing components, as disclosed in detail hereinabove.

As disclosed hereinabove with reference to FIGS. 24-29, the ICIs 450, 460, 470 and 480 may be any of the ICIs of the present application and may include any of the embodiments of the ECMs disclosed hereinabove (such as, for example any of the ECMs 25,98, 108, 150, 250, 350 disclosed hereinabove. The ICIs 450, 460, 470 and 480 may each include a telemetry module (such as, for example, the telemetry module 235 of FIGS. 24-26 or the telemetry module 138 of FIG. 27).

Turning to FIG. 31, the system 401 is an embodiment of the system 400 in which the controller/processor units of each of the ICIs 460, 470 and 480 are programmed to bidirectionally wirelessly communicate (through their respective telemetry modules) with the telemetry module of the ICI 450. The controller/processor of the ICI 450 is programmed to bidirectionally wirelessly communicate with the ICIs 460, 470 and 480 through the telemetry module thereof. The controller/processor of the ICI 450 is also programmed to bidirectionally wirelessly communicate with the external controller/processor 290 through the telemetry module thereof.

In operation, when the system 401 is used to sense/record electrical activity in cortical regions and to stimulate cortical and/or deep brain regions using the ICIs 450, 460, 470 and 480, the recorded signals from the sensing electrodes of any of the ICIs 460, 470 and 480 may be wirelessly communicated to the controller/processor of the ICI 450 for storage and/or processing. After storage and/or processing of the sensed/recorded signals or data, the ICI 450 may wirelessly communicate the stored sensed signal/data and/or the processed data from all the ICIs that performed sensing (including the ICI 450, if the ICI 450 is also used for performing sensing/recording) to the external controller/processor 290. If the data received by the external controller/processor 290 needs processing or further processing, the external controller/processor 290 may process or further process the data for generating any necessary stimulation control signals.

The generated stimulation control signals may be wirelessly transmitted by the telemetry unit included in the external controller/processor 290 to the ICI 450. The ICI 450 may then wirelessly transmit stimulating control signals to the relevant ICIs in order to perform synchronized stimulation of the brain by the relevant ICIs. If the ICI 450 itself is also used for stimulation, the ICI 450 may be programmed to synchronize its internally generated stimulation control signals with the control signals transmitted wirelessly to any relevant ICIs of the other ICIs 460, 470 and 480 and to take into account any delays caused by the wireless transmission time and any processing time required by the ICIs to which such stimulation control signals are being transmitted. It is noted that in the system 401, the ICI 450 may be referred to as a "master ICI" and the ICIs 460, 470 and 480 may be referred to as "Slave ICIs".

The advantages of using the system 401 disclosed hereinabove, may include, inter alia, simplifying the communication scheme used by the external controller/processor 290 as the telemetry module of the external controller/processor 290 may need to communicate only with a single ICI (the ICI 450), and the saving of power for the ICIs 460, 470 and 480 as they may use reduced power in communicating with the ICI 250 due to the shorter distances between the ICI 450 and the ICIs 460, 470 and 480. However, the ICI 450 may still require more power for communication with the external controller/processor 290 than with the ICIs 460, 470 and 480 as the distance between the external controller/processor 290 and the ICI 450 may be longer as compared to the distances between the ICI 450 and the ICIs 460, 470 and 480).

Turning to FIG. 32, the ICI system 402 is an embodiment of the ICI system 400 in which the controller/processor units of each of the ICIs 450, 460, 470 and 480 are programmed to bidirectionally wirelessly communicate (through their respective telemetry modules) with the telemetry module of the external controller/processor 290. The external controller/processor 290 is programmed to bidirectionally wirelessly communicate with each of the ICIs 450, 460, 470 and 480 through the telemetry module thereof.

In operation of the system 402, when the system 402 is used to sense/record electrical activity in one or more cortical regions and to stimulate one or more cortical and/or deep brain regions using the ICIs 450, 460, 470 and 480, the recorded signals from the sensing electrodes of any of the ICIs 450, 460, 270 and 280 may be wirelessly communicated to the external controller/processor 290 for storage and/or processing. The external controller/processor 290 may wirelessly receive the stored sensed signals or data and/or the processed data from all the ICIs that performed sensing from all the ICIs of the system 402 that performed sensing. The external controller/processor 290 may process or further process (in case the sensed signals are partially processed by the respective processor/controllers of the ICIs) the data received from the ICIs 450, and/or 460 and/or 470 and/or 480 and may generate any necessary stimulation control signals. The generated control signals may be wirelessly transmitted by a telemetry unit (not shown) included in the external controller/processor 290 to one or more of the ICIs 450, 460, 470 and 480 in order to perform stimulation of the brain by the relevant ICIs.

The advantages of the system 402 may be, inter alia, reducing power requirements due to no or minimal processing of the sensed signals by the ICIs 450, 460, 470 and 480, and simplifying the programs operative on the ICIs (at least by simplifying the program operative on the ICI 450) by eliminating the need for receiving and/or storing data from the remaining ICIs 460, 470 and 480 and for transmitting of stimulation control signals from the ICI 450 to the remaining ICIs participating in stimulation.

It will be appreciated that in all of the multi-ICI systems 400, 401 and 302 many different configurations may be implemented. For example, in some systems, one or more of the ICIs 450, 460, 470 and 480 may be used for sensing, and one or more of the ICIs 450, 460, 470 and 480 may be used for stimulation. Generally, any combinations of sensing and stimulating may be used. For example, in some embodiments all of the ICIs 450, 460, 470 and 480 may be used for both sensing and stimulating. In other embodiments, one ICI may be used for sensing while the remaining ICIs may be used for stimulating. In other embodiments, two ICIs may be used for sensing and two or more ICIs may be used for stimulating. In short, any desired number of ICIs selected from the ICIs 450, 460, 470 and 480 may be used for sensing and/or for stimulation depending, inter alia, on the site of implantation and the type of stimulation being used, such as, for example, stimulation by passing current pulses between different electrodes of a single ICI, or stimulation using the frequency interference (FI) method as disclosed hereinabove using any electrode combinations of one or more ICIs.

It is noted that while, theoretically, it may be possible to perform FI stimulation by using two different stimulation frequencies each delivered from a different electrode of the same ICI, such stimulation may be of limited usefulness because of the relatively short distance between two electrodes of the same ICI. Therefore, in some embodiments of the ICI systems, FI stimulation may be performed by using two or more different ICIs of the ICI system. For example, FI stimulation may be performed by using stimulating electrodes of a first ICI (such as for example, the ICI 450) and the stimulating electrodes of a second ICI (such as, for example, the ICI 480) to pass therebetween alternating currents at a first frequency F1 (for example 2,000 Hz) and simultaneously use stimulating electrodes of a third ICI (such as for example, the ICI 460) and the stimulating electrodes of a third ICI (such as, for example, the ICI 470) to pass therebetween alternating currents at a second frequency F2 (for example 2,050 Hz).

It is also noted that while the systems 400, 401 and 402 include four ICIs, this is by no means limiting and other embodiments of multi-ICI systems may be implemented with any desired number of ICIs (typically, in the range between 2-10 (two to ten) ICIs, but ICI numbers higher than 10 may also be implemented, depending, inter alia, on the specific application, the dimensions of the ICIs being used, the type of stimulation required and other considerations). In some embodiments of such multi-ICI system the external controller/processor (such as for example the external controller/processor 290) may directly wirelessly communicate with all the ICIs of the multi-ICI system for receiving data therefrom and for transmitting control signals thereto. In other embodiments of such multi-ICI systems, the external controller/processor (such as for example the external controller/processor 290) may wirelessly bidirectionally communicate with one (or possibly, more than one Master type ICIs while the remaining ICIs may be of the slave type which may wirelessly bidirectionally communicate with such one or more master type ICIs.

It is also noted that, in some embodiments, the ICI systems may operate autonomously without the mediation of the external controller processor 290. In such autonomous systems, the sensing ICI(s) may wirelessly communicate sensed signals and/or processed signals (for example digitized signals) to a master ICI (such as, for example the ICI 450) that may process the received signals or processed signals from one or more sensing ICIs to detect an indication of a physiological or neurological or neuropsychiatric state of the patient. The master ICI may wirelessly transmit stimulation control commands/signals to one or several ICIs of the ICI system to control the stimulation of the brain by the stimulating ICIs (such stimulation may include direct stimulation of the cortex and/or FI stimulation of one or more deep brain structures). It is noted that if the master ICI is participating in the stimulation, the master ICI may synchronize its own stimulation activity with the stimulating activity of the remaining stimulating ICIs. In such autonomous ICI systems, the ICIs may operate autonomously without the need to communicate with an external controller/processor. However, such autonomous systems may still make use of the external controller/processor 290 for wireless programming or reprograming the ICIs software and/or for periodically offloading ICI data for monitoring the system's operation.

It will be appreciated, that the ICI disclosed and illustrated hereinabove are not limiting and that other different ICI embodiments and configurations may be implemented.

Figure 33:
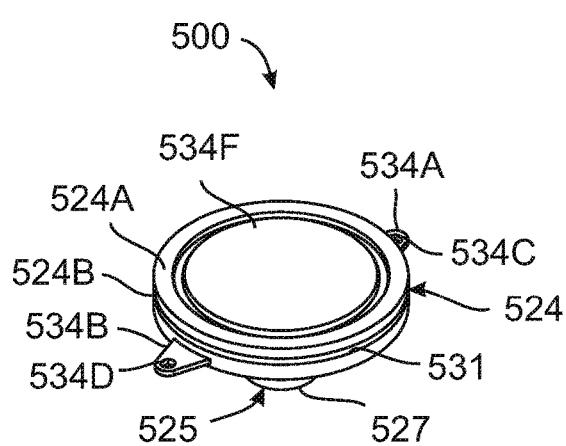
FIG. 33 is a schematic isometric view illustrating an ICI having a narrow tube-like current directing mechanism, in accordance with some embodiments of the ICIs of the present application.
Figure 36:
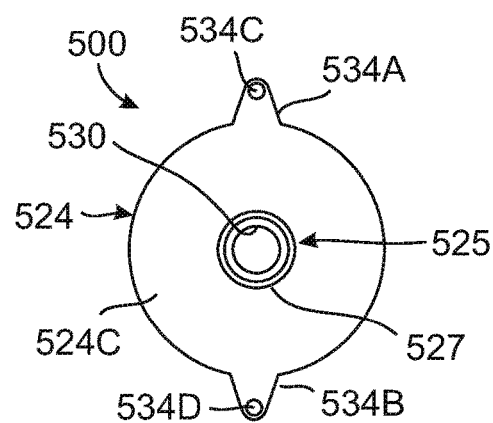
FIG. 36 is a schematic bottom view of the ICI of FIG. 33.
Figure 34:
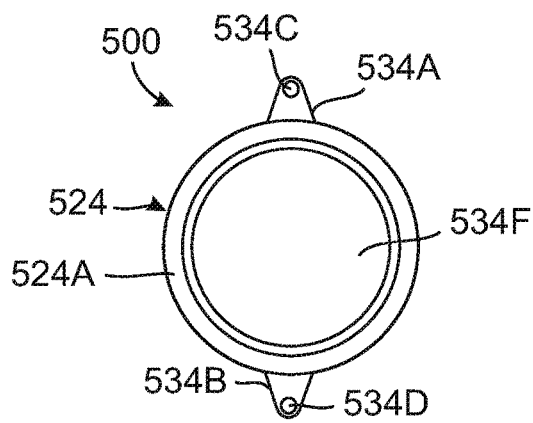
FIG. 34 is a schematic top view of the ICI of FIG. 33.
Figure 35:
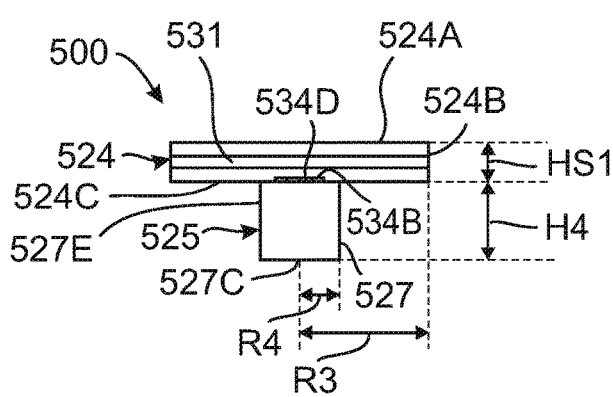
FIG. 35 is a schematic side view of the ICI of FIG. 33.

Reference is now made to FIG. 33-36. FIG. 33 is a schematic isometric view illustrating an ICI having a narrow tube-like directing mechanism, in accordance with some embodiments of the ICIs of the present application. FIG. 34 is a schematic top view of the ICI of FIG. 33. FIG. 35 is a schematic side view of the ICI of FIG. 33. FIG. 36 is a schematic bottom view of the ICI of FIG. 33.

The ICI 500 may include a sealed compartment 524, a current directing mechanism 525, an ECM 28 (not shown in FIG. 33, the ECM 28 may be seen in FIGS. 1 and 3 and in the cross-sectional view of FIG. 43), a stimulating electrode 530 and an auxiliary electrode 531. The sealed compartment 524 includes a top part 524Am, a bottom part 524C and a side wall 524 extending between the top part 524A and the bottom part 524C.

The ECM 28 may be sealingly disposed within the sealed compartment 524 and may be identical to the ECM 28 of FIG. 1 (but may also be implemented as any of the ECMs 150, 250, 350 and 230 of FIGS. 24, 25, 26 and 27, respectively).

The sealed compartment 524 and the ECM 28 may be constructed and operated as disclosed in detail hereinabove with respect to the sealed compartment 24 and the ECM 28 of the ICI 10. However, the sealed compartment 24 has tabs 534A and 534B attached to or extending from the side wall 524B of the sealed compartment 524 near the bottom part 524C of the sealed compartment 520. The tab 534A has a hole 534C formed therein and the tab 534B has a hole 534D formed therein. The Tabs 534A and 534B may be used for attaching the ICI 500 to the surface of the calvarial bone 4.

The top part 534A of the sealed compartment 524 may include a magnet 530F attached thereto. The magnet 534F may be useful for attaching a wireless energizing device to the scalp 1 after implantation of the ICI 500 (see FIGS. 37-38 Hereinafter).

Figure 41:
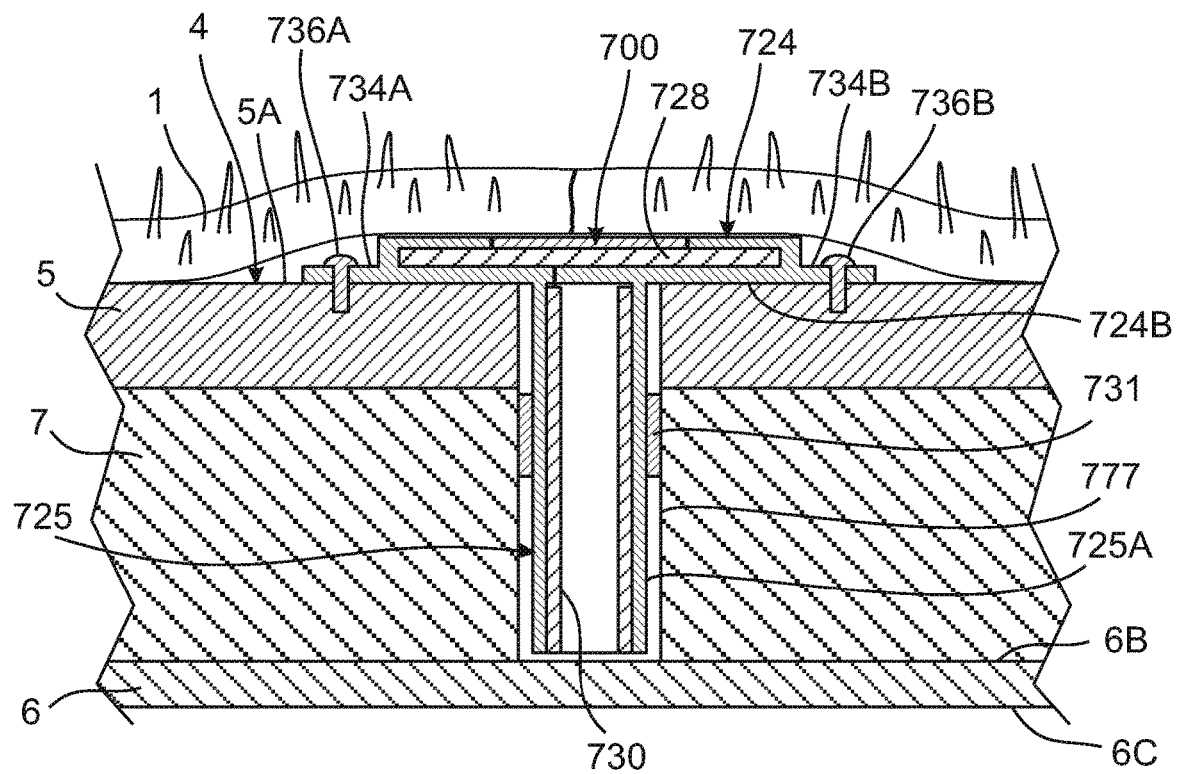
FIG. 41 is a schematic cross-sectional view illustrating an ICI implanted in a calvarial bone, in accordance with some embodiments of the ICIs of the present application.
Figure 42:
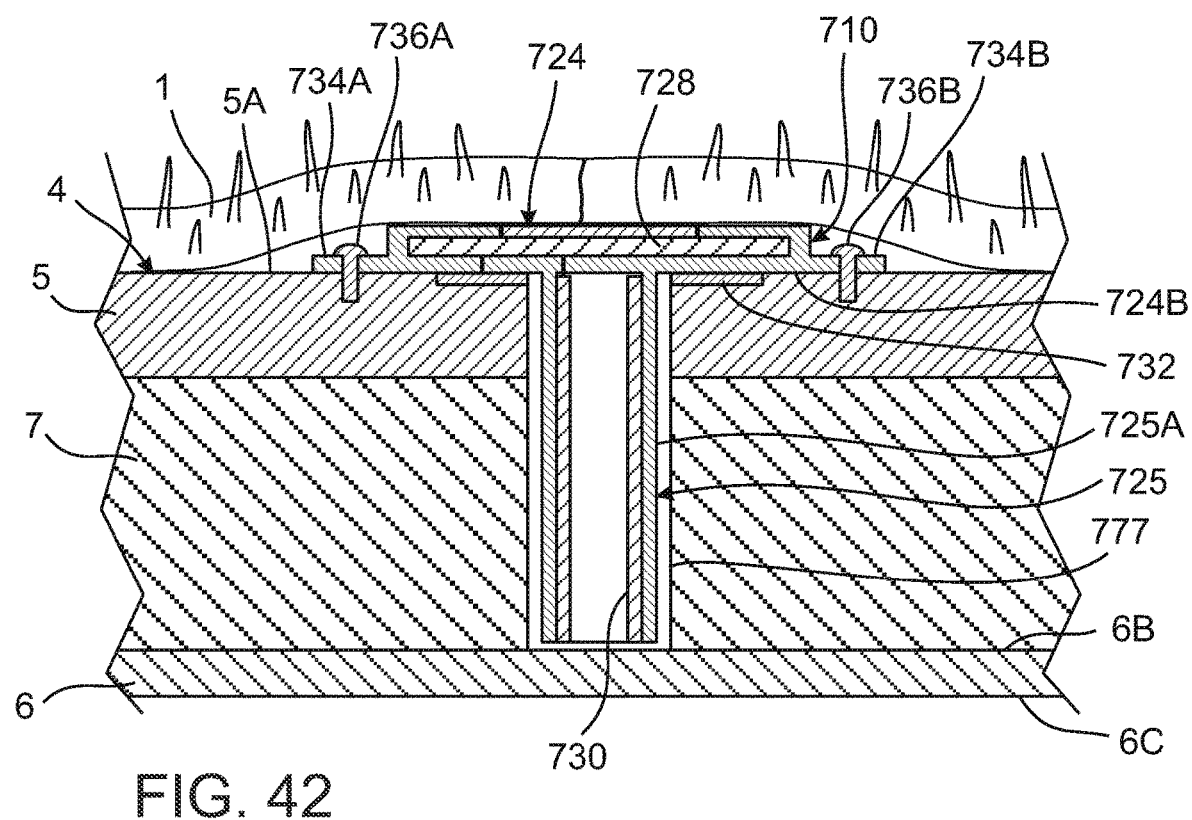
FIG. 42 is a schematic cross-sectional view illustrating another ICI implanted in a calvarial bone, in accordance with some embodiments of the ICIs of the present application.
Figure 43:
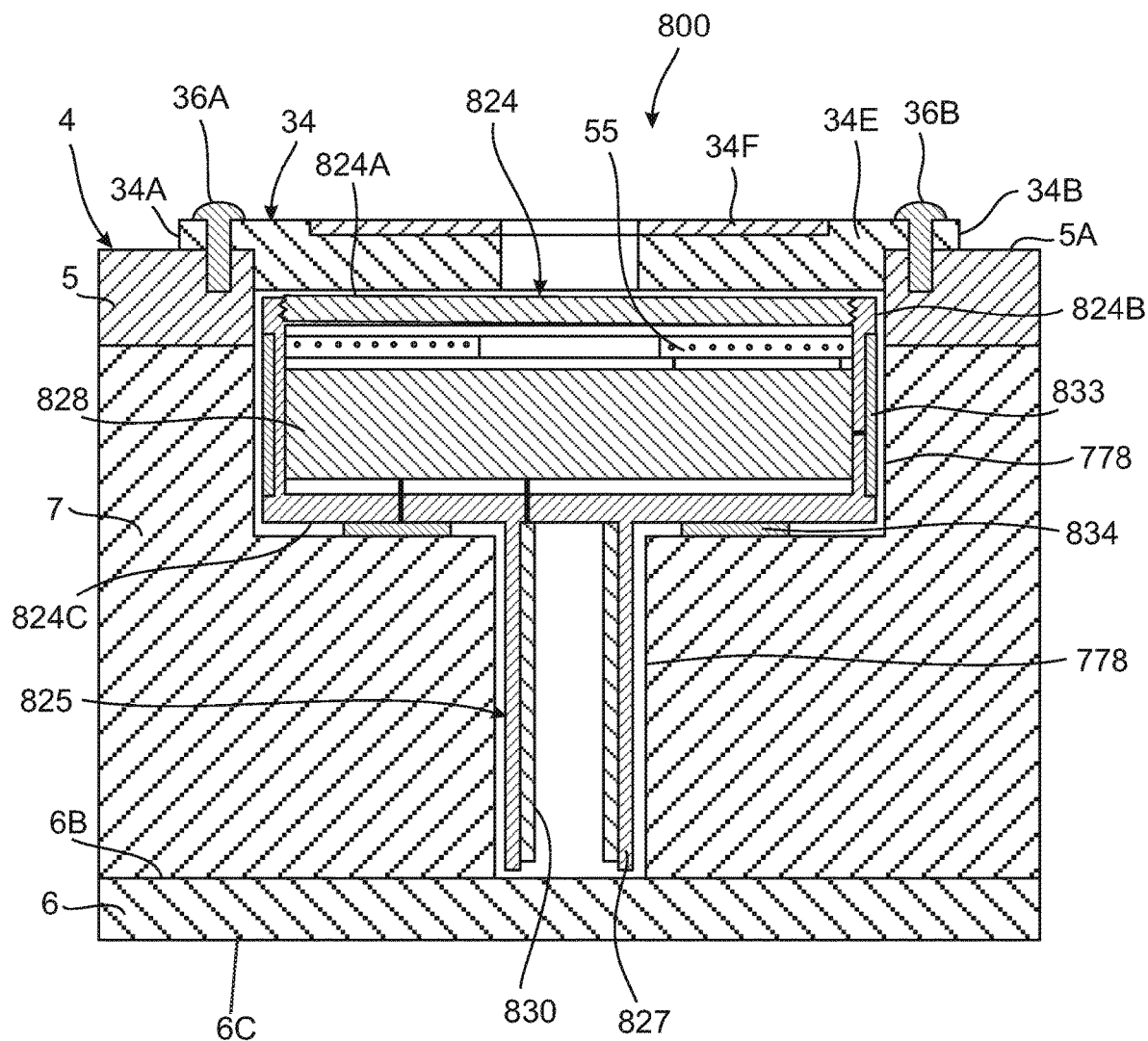
FIG. 43 is a schematic cross-sectional view illustrating an ICI and a shimming member implanted in a calvarial bone, in accordance with some embodiments of the ICIs of the present application.

The auxiliary electrode 531 may be implemented as a ring-like electrode attached to the side wall 524B of the sealed compartment 524 (as illustrated in FIGS. 33 and 35). However, in other embodiments of the ICI, the auxiliary electrode may have a different shape and may be attached to the bottom part of the sealed compartment of the ICI (as illustrated in FIGS. 42 and 43 hereinafter) or to the outer surface of the current directing mechanism (as illustrated in FIG. 41 hereinafter). When current is being passed between the auxiliary electrode 531 and the stimulating electrode 530, the stimulating electrode 530 may be operated as a cathode or as an anode, depending on the polarity of the current passed between the electrodes 530 and 531. Therefore, the auxiliary electrode 531 may be operated as a current sink or as a current source depending on the polarity of the voltage pulse applied to the electrodes 530 and 531.

In accordance with some embodiments, the current directing mechanism 525 may be a cylindrically shaped wall 527 that may be attached to or extending from the bottom part 524C of the sealed compartment 524 the wall 527 has a first end 527E attached to or extending from the bottom part 524C of the sealed compartment 524 and a second open end 527C having a circularly shaped opening. It is noted that while the stimulating electrode 530 may be implemented as a cylindrical hollow electrode attached to the wall 527 (as illustrated in FIG. 36), in some embodiments, the stimulating electrode 530 may be implemented as a cylindrical hollow electrode attached to the bottom part 524C such that there is a space between the electrode 530 and the wall 527 of the current directing member 526. Such an embodiment may be better in applications where a larger electrode surface is required as it almost doubles the surface area available for passing current through the stimulating electrode 530. In some embodiments, the electrode 530 may be implemented as a thin cylindrical layer made from a conducting material (such as, for example platinum) that may be deposited or plated on the inner surface of the wall 527, as disclosed hereinabove).

Briefly Returning to FIGS. 2-3, a typical value for the radius R (of FIG. 3) of the sealed compartment 24 is 10.5 mm and R may typically vary in the range of 5-12 mm. The typical radius R5 of the current directing mechanism 25 may be about 5 mm and the value of R5 may be in the range of 2-9 mm. Therefore, a typical (but not obligatory) value for the ratio of R5/R is about 0.5.

In contrast, a typical value of the radius R4 of the current directing member 525 may be about 1 mm and the range of values for the radius R4 is 0.5-8 mm. The height (thickness) HS1 of the sealed compartment 524 may be in the range of 0.2-3 mm and a typical value may be HS1=2 mm. Typically, the height H4 of the current directing member may be H4=4 mm (similar to the typical value of H of FIG. 2). However, this value of H4 is not obligatory and the value of H4 may vary, depending inter alia, on the thickness of the calvarial bone at the site of implantation, the particular application and other considerations. It is noted that the values of R3, R4, HS1 and H4 may vary and may be smaller or larger than the particular value of ranges indicated above.

It is further noted that because of the relatively small radius R4 as compared to the radius R3 (typically, but not obligatorily R4/R3 is about 0.25), this ICI configuration may be referred to as a "thumbtack" IC. Among the advantages of such a "thumbtack" ICI configuration is that it's implantation may be less invasive and simpler than the implantation of the ICI 10. For example, in order to implant the ICI 500, it is may be possible to drill a cylindrical passage having a significantly smaller diameter than the diameter of the passage required for implanting a typical embodiment of the ICI 10 (typically, a passage having a diameter of about 2 mm for implanting the ICI 525, as compared to a passage with a diameter of about with typical diameter of 21 mm that may be required for implanting a typical embodiment of the ICI 10).

Figure 37:
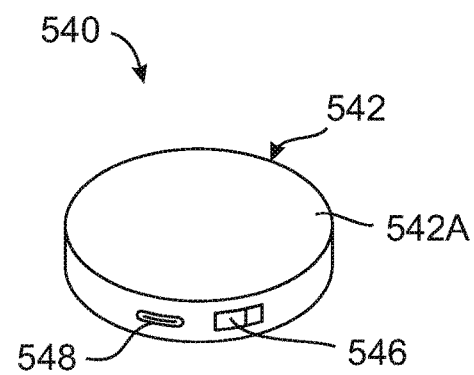
FIG. 37 is a schematic isometric view illustrating an energizing device for wirelessly providing energy to the ICIs of the present application.
Figure 38:
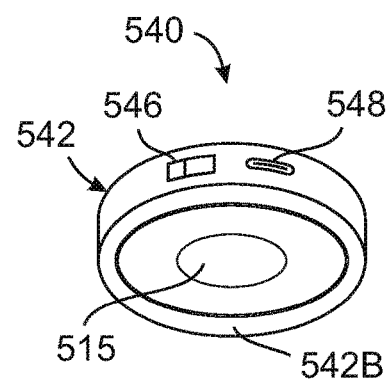
FIG. 38 is another schematic isometric view of the energizing device of FIG. 37.
Figure 39:
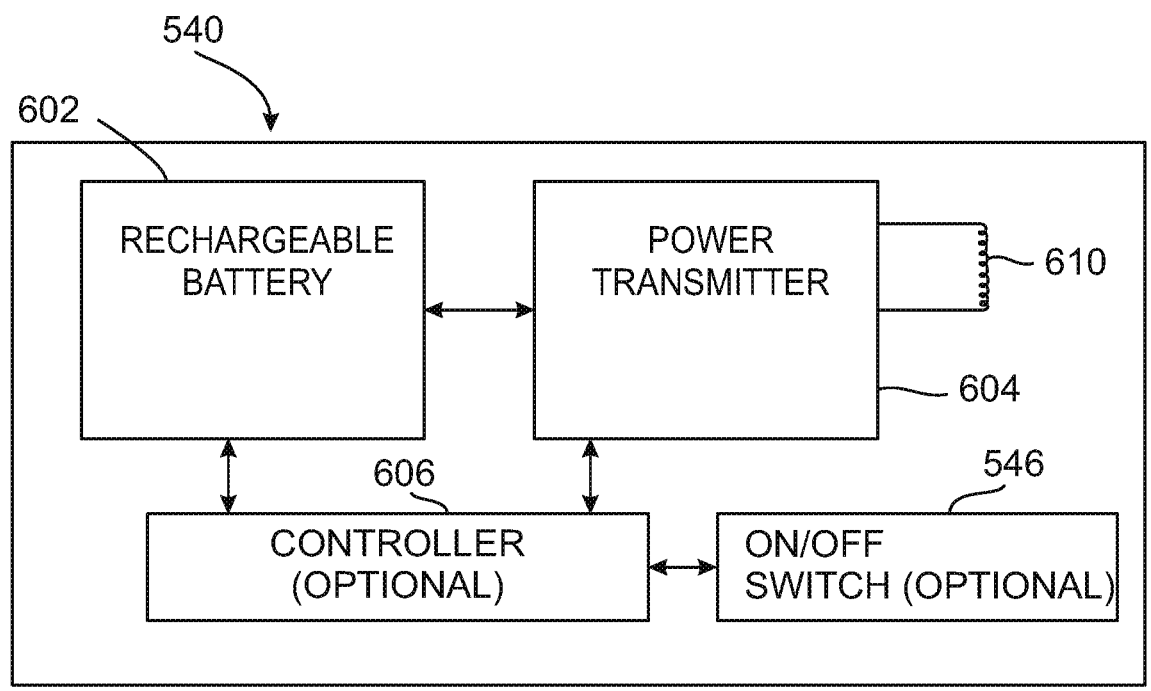
FIG. 39 is a schematic block diagram illustrating components of the energizing device of FIGS. 37 and 38.

Reference is now made to FIGS. 37-39. FIG. 37 is a schematic isometric view illustrating an energizing device for wirelessly providing energy to the ICIs of the present application. FIG. 38 is another schematic isometric view of the energizing device of FIG. 38. FIG. 39 is a schematic block diagram illustrating components of the energizing device of FIGS. 39 and 40.

The energizing device 540 may include a housing 542 having a top part 542A and a bottom part 542B. The housing 542 may be sealed and may be shaped as a thin disk-like housing. The housing 542 may include a magnet 515 attached to or included in the bottom part 542B of the housing 542. The energizing device 540 may include a rechargeable battery 602, a power transmitter 604 having a transmitting inductance coil 610, an (optional) controller 606 and an (optional) on/off switch 546, and an (optional) charging socket for charging the rechargeable cell 602. The rechargeable battery 602 may be connected to the controller 606 and to the power transmitter 604 to provide electrical energy thereto.

The rechargeable battery may be a lithium ion rechargeable cell or a lithium polymer rechargeable cell or any other suitable type of rechargeable cell. The (optional) on/off switch 546 may be installed in the housing 542 and operatively connected to the controller 606. The controller 606 may control the operation of the power transmitter 604. The power transmitter 604 may include circuitry that may provide a pulsatile current or an alternating current to the inductance coil 610. When the energizing device 542 is placed on the scalp 1, the inductance coil 610 may transmit electromagnetic waves to another inductance coil of the ICI implanted in the calvarial bone (for example to the inductance coil 55 of FIG. 12). When the energizing device 540 is placed on the scalp 1 near the site of implantation of the ICI, the magnet 515 is attracted to the magnet of the ICI (for example, to the magnet 34F of the ICI 10, or to the magnet 534F of the ICI 500) and may assist the alignment of the coils 515 with the coil 55 of the IC. The attraction between the magnets may also assist in stably holding the energizing device 540 on the scalp 1 and to prevent the energizing device 540 from falling off the scalp 1. The energizing device 540 advantageously obviates the need to store a bulky energy source within the ICI as it wirelessly provides power to the ECM of the ICIs, as disclosed in detail hereinabove with respect to the external inductance coil 60 (of FIG. 15). The socket 548 may be any suitable charging socket (such as, for example a mini USB socket).

In some embodiments of the energizing device, the charging of the rechargeable battery 602 may be performed wirelessly. In other embodiments, the housing 20 may include only the rechargeable battery 602 connected to the power transmitter 604. In such embodiments the energizing device when charged constantly transmits power making the on/off switch 546 and the controller 606 redundant. In some embodiments (such as the energizing device 540, the rechargeable battery may be charged with the on/off switch 546 in the "off" position to prevent power transmitting during charging and the on/off switch 546 may be turned to the "on" position prior to placement of the energizing device 540 on the scalp 1.

It is noted that while the ICI 500 includes only a single stimulating electrode 530 within the current directing mechanism 525, this is not obligatory, and other "thumbtack" type ICIs may include additional or different electrode.

Figure 40:
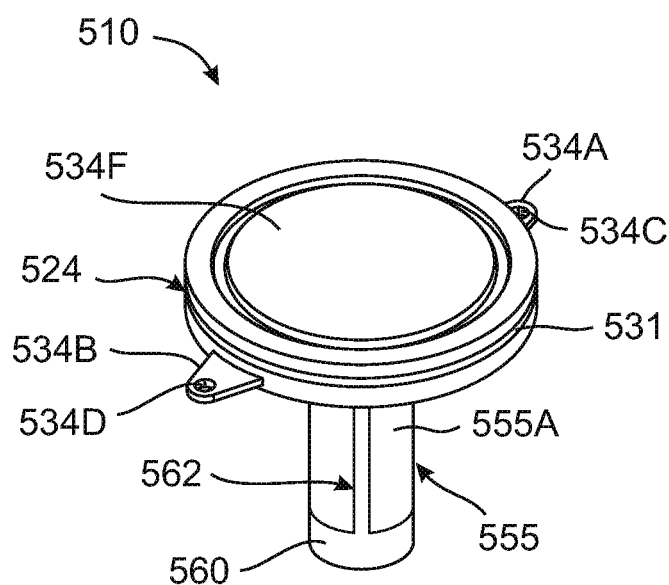
FIG. 40 is a schematic cross-sectional view illustrating an ICI implanted in a calvarial bone, in accordance with some embodiments of the ICIs of the present application.

Reference is now made to FIG. 40 which is a schematic cross-sectional view illustrating an ICI implanted in a calvarial bone, in accordance with some embodiments of the ICIs of the present application. The ICI 510 may be similar to the ICI 500 but with the different current directing mechanism 555. The current directing mechanism 555 may include the stimulating electrode 530 disposed within the current directing mechanism (it is noted that the stimulating electrode 530 is not seen in the isometric view of FIG. 40). The current directing mechanism 555 may also include a sensing/recording electrode 560 attached to or deposited upon the external surface 555A of the current directing mechanism 555. For example, the sensing/recording electrode 560 may be a thin layer of platinum coated on or deposited upon the external surface 555A of the current directing mechanism 555. An electrically conducting electrically isolated thin strip 562 of platinum may be used to electrically connect the sensing/recording electrode 560 to the ECM (not shown in the isometric view of FIG. 40) disposed within the sealed compartment 524 of the ICI 510. Thus, the ICI 510 may be able to perform sensing simultaneously with stimulation (provided suitable stimulation artifact cancellation methods are employed by the ECM of the ICI 510. Alternatively, the ICI 510 may alternate between sensing and stimulating in order to reduce or eliminate pickup of stimulating artifacts by the sensing/recording electrode 560.

Reference is now made to FIGS. 41-42. FIG. 41 is a schematic cross-sectional view illustrating an ICI implanted in a calvarial bone, in accordance with some embodiments of the ICIs of the present application. FIG. 42 is a schematic cross-sectional view illustrating another ICI implanted in a calvarial bone, in accordance with some embodiments of the ICIs of the present application.

Turning to FIG. 41, the ICI 700 includes a sealed compartment 724 having two tabs 724A and 724B, an ECM 728 and a current directing mechanism 725. A single stimulating electrode 730 is disposed within the current directing mechanism 725 and a cylindrical auxiliary electrode 731 is attached to the external surface 725A of the current directing mechanism 725 as illustrated in FIG. 41. During implantation, the current directing mechanism 725 is inserted into the hollow passage 777 drilled through the outer table 5 and the cancellous bone 7 until the bottom part 724B of the sealed compartment 724 is in contact with the outer surface 5A of the outer table 5. Bone screws 736A and 73B may be used to firmly attach the ICI 700 to the calvarial bone 4 to prevent any movements and/or rotations of the ICI 700 after implantation. In operation, the ICI 700 is similar to the ICI 525, except that stimulation may be performed by passing current between the stimulating electrode 730 and the auxiliary electrode 731 and the auxiliary electrode 731 is disposed closer to the inner table 6 electrode (as compared to the auxiliary electrode 530 of the ICI 525). After implantation, the sealed compartment 724 is disposed between the calvarial bone 4 and the scalp 1.

Turning to FIG. 42, the ICI 710 is similar in construction and operation to the ICI 700, except that the ICI 710 an annular auxiliary electrode 732 attached to the bottom part 724B of the sealed compartment 724 is used instead of the auxiliary electrode 731 of the ICI 700.

Reference is now made to FIG. 43 which is a schematic cross-sectional view illustrating an ICI and a shimming member implanted in a calvarial bone, in accordance with some embodiments of the ICIs of the present application.

The ICI 800 includes a sealed compartment 824 having a top part 824A, a bottom part 824C and a side wall extending between the top part 824A and the bottom part 824C. The ICI 800 also includes a current directing mechanism 825 extending from the bottom part 824C. The ICI 800 also includes an ECM 828 (similar in construction and operation to the ECM 28 of FIG. 1) and the inductance coil 55 (of FIG. 12). The ECM 828 and the inductance coil 55 are disposed within the sealed compartment 824. The ICI 800 may include a stimulating electrode 830, attached to the wall 827 of the current directing mechanism 825. The stimulating electrode 830 is electrically coupled to the ECM 828.

The ICI 800 may also include a cylindrical auxiliary electrode 833, attached to the side wall 824B of the sealed compartment 824 of the current directing mechanism 825. The auxiliary electrode 833 is electrically coupled to the ECM 828. The ICI 800 may also include an annular reference electrode 834, attached to the bottom part 824C of the sealed compartment 824. The reference electrode 834 is electrically coupled to the ECM 828.

The ICI 800 of FIG. 43 is shown after being implanted in a skull. After exposing the surface of the calvarial bone 4 and deflecting the scalp flaps (the scalp is not shown in FIG. 43 for the sake of clarity of illustration), a stepped hollow passage 778 is formed in the calvarial bone 4 as illustrated in FIG. 43. The ICI 800 is then inserted into the passage 778 as illustrated. The shimming member 34 (see FIGS. 1-2 and 4-6 for a detailed description of the shimming member 34) may then be glued or otherwise attached to the top part 824A of the sealed compartment 824 (as disclosed in detailed hereinabove) and the shimming member 34 may then be attached to the outer surface 5A of the outer table 5 by screws 36A and 36B as disclosed in detail hereinabove. It is noted that the sealed compartment 824 is fully embedded within the passage 778 and that the shimming member 34 closes the opening of the passage.

In operation, the ICI 800 may be used for sensing (for example by performing differential recording between the reference electrode 834 and the stimulating electrode 830 (which may be operating in this case as a sensing/recording electrode during time periods in which no stimulation is being performed). The ICI 800 may also be used for stimulation by passing current pulses between the auxiliary electrode 833 and the stimulating electrode 830 (during stimulation, sensing may not be performed). During stimulation, the auxiliary electrode 833 may operate as an anode or as a cathode, depending on the polarity of the voltage pulses applied to the electrodes 830 and 833.

It is noted that while the "thumbtack" shaped ICI configuration may be particularly useful in cases where a single stimulating electrode with a large surface area is required (such as for example when two or more ICIs are used for performing FI stimulation of brain regions deeper than the cortex, as described in detail hereinabove), this is by no means obligatory and embodiments of "thumbtack" ICIs may also include multiple stimulating and/or sensing electrodes.

Figure 44:
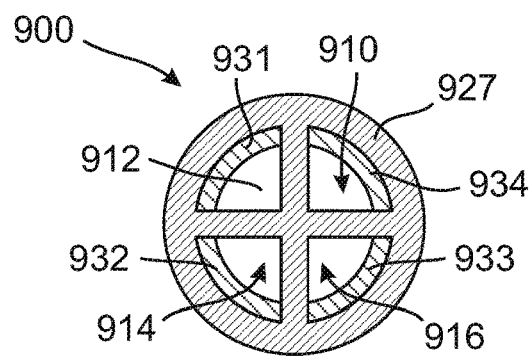
FIG. 44 is a schematic cross-sectional view of a current directing member having four electrodes therein, in accordance with some embodiments of the current directing members of the present application.
Figure 45:
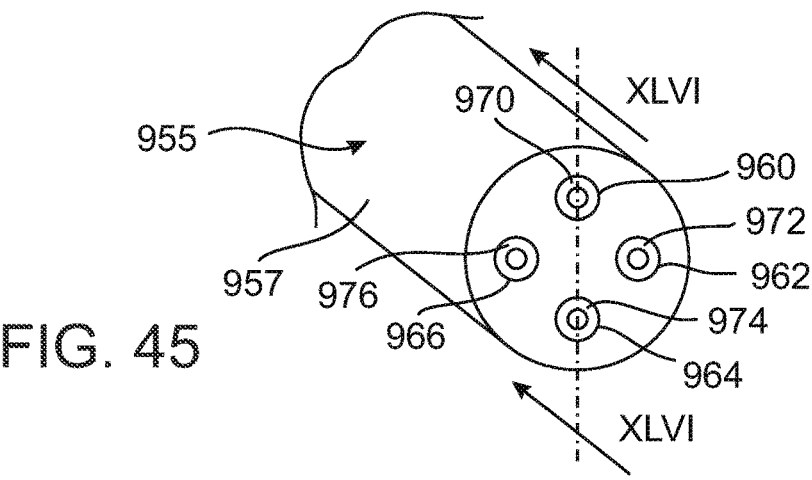
FIG. 45. is a schematic isometric view illustrating part of a current directing member having 4 tube-like electrodes therein, in accordance with some embodiments of the current directing members of the present application.
Figure 46:
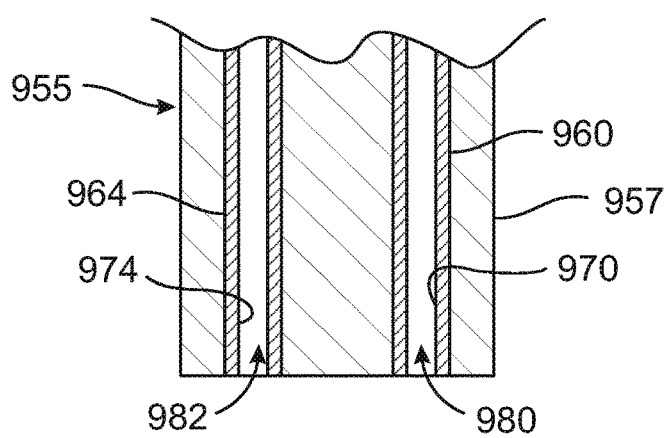
FIG. 46 is a schematic cross sectional view of the part of the current directing member of FIG. 45 taken along the lines XLVI-XLVI.
Figure 47:
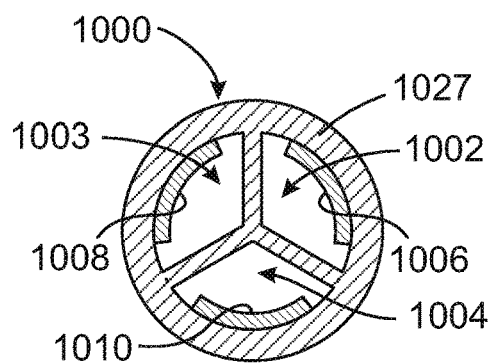
FIG. 47 is a schematic cross-sectional view of a current directing member having three electrodes therein, in accordance with some embodiments of the current directing members of the present application.
Figure 48:
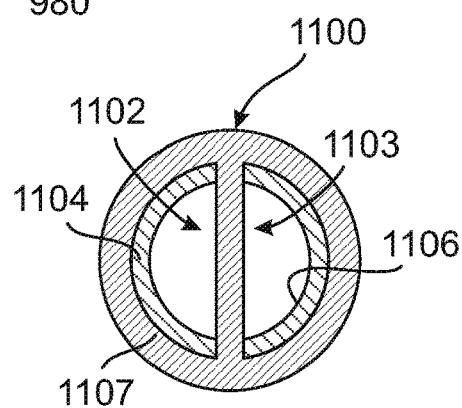
FIG. 48: is a schematic cross-sectional view of a current directing member having two electrodes therein, in accordance with some embodiments of the current directing members of the present application.

Reference is now made to FIGS. 44-48. FIG. 44 is a schematic cross-sectional view of a current directing member having four electrodes therein, in accordance with some embodiments of the current directing members of the present application. FIG. 45 is a schematic isometric view illustrating part of a current directing member having 4 tube-like electrodes therein, in accordance with some embodiments of the current directing members of the present application. FIG. 46 is a schematic cross-sectional view of the part of the current directing member of FIG. 45 taken along the lines XLVI-XLVI. FIG. 47 is a schematic cross-sectional view of a current directing member having three electrodes therein, in accordance with some embodiments of the current directing members of the present application. FIG. 48 is a schematic cross-sectional view of a current directing member having two electrodes therein, in accordance with some embodiments of the current directing members of the present application.

Turning to FIG. 44, the current directing mechanism 900 (only part of which is seen in the cross-sectional view of FIG. 44) includes a shank 927 and four hollow passages 910, 912, 914 and 916 passing along the shank 927. The shank 927 may be made of any of the biocompatible electrically isolating materials disclosed hereinabove for the current directing mechanism 25 (of FIG. 1). Four electrodes 934, 933, 932 and 931 are disposed within the four hollow passages 910, 916, 914 and 912, respectively, as illustrated in FIG. 44. The electrodes 931, 932, 933 and 934 may operate as sensing/recording electrodes and/or as stimulating electrodes.

Turning to FIGS. 45-46, the current directing mechanism 955 (only part of which is seen in the cross-sectional view of FIGS. 45-46) includes a cylindrical shank 957 and four hollow passages 960, 962, 964 and 966 passing along the shank 957. The shank 957 may be made of any of the biocompatible electrically isolating materials disclosed hereinabove for the current directing mechanism 25 (of FIG. 1). Four cylindrical electrodes 970, 972, 974 and 976 are disposed within the four hollow passages 960, 962, 964 and 966, respectively, as illustrated in FIGS. 45-46. The electrodes 970, 972, 974 and 976 may be hollow and may have open ends (such as, for example the open ends 980 and 982 of FIG. 46). The electrodes 970, 972, 974 and 976 may operate as sensing/recording electrodes and/or as stimulating electrodes.

Turning to FIG. 47, the current directing mechanism 1000 (only part of which is seen in the cross-sectional view of FIG. 47) includes a cylindrical shank 1027 and three hollow passages 1002, 1003 and 1004 passing along the shank 1027. The shank 1027 may be made of any of the biocompatible electrically isolating materials disclosed hereinabove for the current directing mechanism 25 (of FIG. 1). Three electrodes 1006 are each disposed within the three hollow passages 1002, 1003 and 1004, respectively, as illustrated in FIG. 47. The electrodes 1002, 1003 and 1004 may operate as sensing/recording electrodes and/or as stimulating electrodes.

Turning to FIG. 48, the current directing mechanism 1100 (only part of which is seen in the cross-sectional view of FIG. 48) includes a cylindrical shank 1127 and two hollow passages 1102, and 1103 passing along the shank 1127. The shank 1127 may be made of any of the biocompatible electrically isolating materials disclosed hereinabove for the current directing mechanism 25 (of FIG. 1). Two electrodes 1104 and 1106 having a semilunar cross-sectional shape are disposed within the two hollow passages 1102, and 1103, respectively, as illustrated in FIG. 48. The electrodes 1102, and 1103 may operate as sensing/recording electrodes and/or as stimulating electrodes.

It is noted that while all the above embodiments of the "Thumbtack" type ICIs have a single current directing mechanism extending from the bottom part of the ICI, this is not obligatory and some ICI embodiments may have several current directing mechanisms extending from the bottom part of the IC. For example, an ICI embodiment (not shown) may have the sealed compartment similar to the sealed compartment 724 of FIG. 42 but instead of having a single current directing mechanism extending from the bottom part of the sealed compartment, the ICI may have four separate current directing mechanisms extending from the bottom part of the IC. Each of the four current directing mechanisms may be similar to the current directing mechanism 725 of FIG. 42 and may include an electrode similar to the electrode 730 of FIG. 42 therein.

When implanting such an embodiment, four hollow passages (each passage of the four passages may be similar to the hollow passage 777 of FIG. 42) may be made in the calvarial bone 4, and the four current directing mechanisms of the ICI may be inserted into the four passages in the calvarial bone. Such ICIs may have different numbers of current directing mechanisms that may vary between 2-6 current directing mechanisms per ICI, but even higher numbers of current directing mechanisms may be used depending, inter alia, on the number of electrodes required, the diameter of the sealed compartment of the ICI and the diameter of each of the current directing mechanisms.

Figure 49:
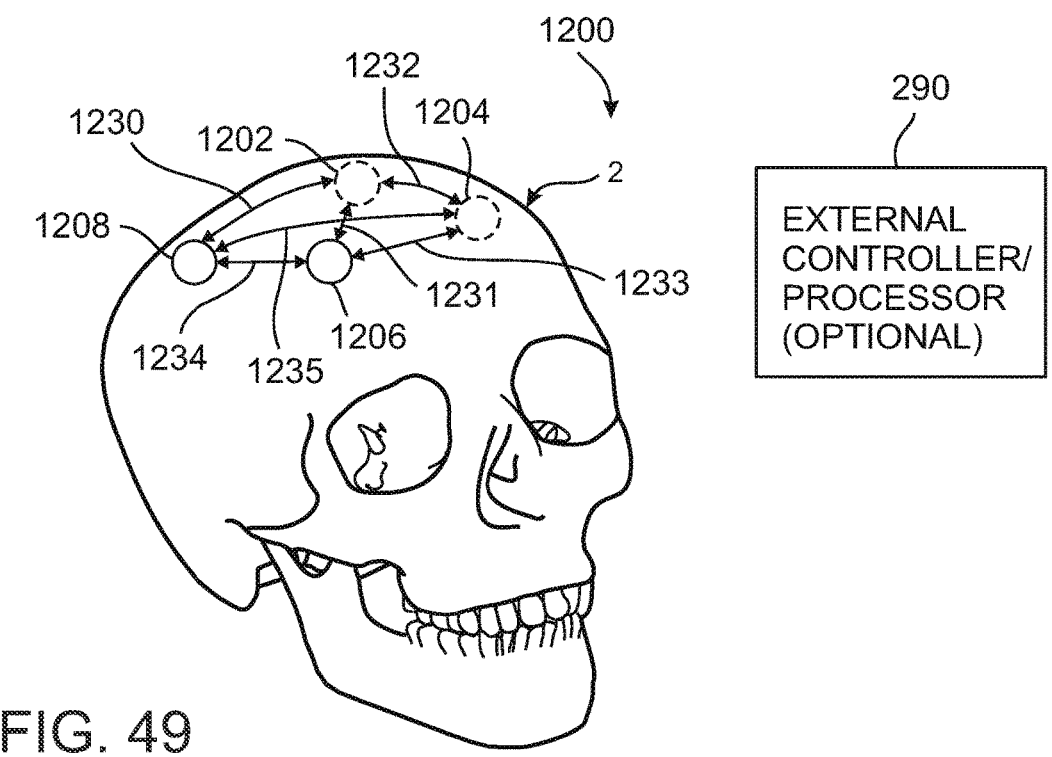
FIG. 49 is a schematic part isometric view of an ICI system, in accordance with some embodiments of the ICI systems of the present Application.

It is noted that some of the "thumbtack" shaped ICIs may be operated in ICI systems including several ICIs implanted within the same skull. Reference is now made to FIG. 49 is a schematic part isometric view of an ICI system, usable in performing frequency interference (FI) in accordance with some embodiments of the ICI systems of the present Application.

The ICI system 1200 includes four ICIs 1202, 1204, 1206 and 1208. The ICIs may be any of the "thumbtack" type ICIs disclosed hereinabove. In some embodiments of the ICI system 1200, the ICIs may be implanted in symmetrical pairs (for example, in an exemplary embodiment, the ICI 1204 may be implanted above the left DLPFC, the ICI 1206 may be implanted above the right DLPFC, while the ICIs 1202 and 1208 may be implanted over other different cortical regions spaced apart from the right and left DLPFC regions as illustrated in FIG. 49. Stimulating currents at different frequencies may be passed into the brain by selected different pairs of the ICIs as schematically illustrated by the six double headed arrows 1230, 1231, 1232, 1233, 1234 and 1236

This type of arrangement of the ICIs may allow better control of the focal stimulation regions resulting from interference and beating of the different frequencies as disclosed in detail by the article of Nir Grossman et al.

It is noted that while a simple and fast method for drilling the passages in the calvarial bone is using a bone drill to drill cylindrical holes in the bone (as disclosed in detail hereinabove), the implantation procedures are not necessarily limited to such drilling methods alone. For example, it may be possible to for recesses and passages of various different shapes in the calvarial bone, by bone ablating techniques using femtosecond pulsed laser ablating methods. However, in contrast to drilling that enables forming cylindrical passages, laser ablating enables forming almost any shape of passage within the calvarial bone. This may enable the current directing mechanisms of some embodiments of the ICIs of the present application to have many different cross-sectional shapes besides cylindrical shapes.

Reference is now made to FIGS. 50-53, which are schematic bottom views illustrating four different types of ICIs having different current directing members, in accordance with some embodiments of the current directing members of the present application.

Figure 50:
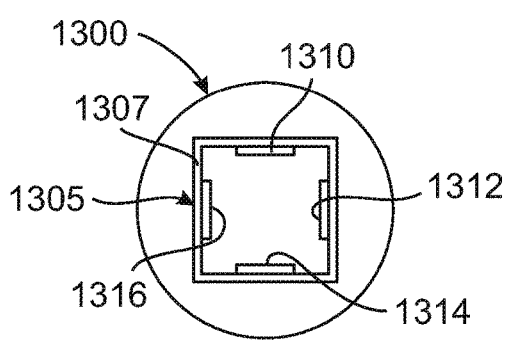
FIGS. 50, 51, 52 and 53 are schematic bottom views illustrating four different types of ICIs having different current directing members, in accordance with some embodiments of the current directing members of the present application.

Turning to FIG. 50, the ICI 1300 (shown in bottom view) has a current directing mechanism 1305 having a square cross-section. The current directing mechanism 1305 has a wall 1307 having a square cross-sectional shape. Four electrodes 1310, 1312, 1314 and 1316 are attached to the wall 1307, as illustrated in FIG. 50. The ICI 1300 may be implanted in a skull by laser ablating a passage having a square cross-section in the calvarial bone of the skull.

Figure 51:
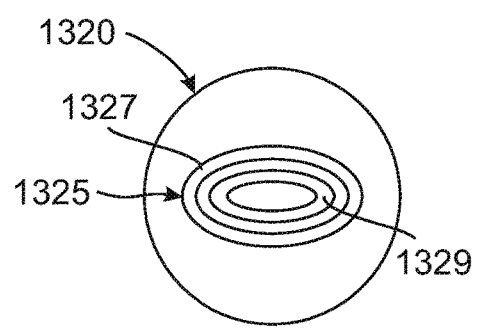

Turning to FIG. 51, the ICI 1320 (shown in bottom view) has a current directing mechanism 1325 having an oval cross-section. The current directing mechanism 1355 has a wall 1327 having an oval cross-sectional shape. A single hollow electrode 1329 having an oval cross-section may be disposed within the wall 1327 of the current directing mechanism 1325, as illustrated in FIG. 51. The ICI 1320 may be implanted in a skull by laser ablating a passage having an oval cross-section in the calvarial bone of the skull.

Figure 52:
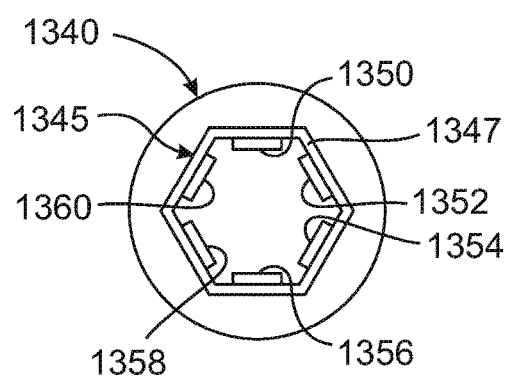

Turning to FIG. 52, the ICI 1340 (shown in bottom view) has a current directing mechanism 1345 having a hexagonal cross-section. The current directing mechanism 1345 has a wall 1347 having a hexagonal cross-sectional shape. Six electrodes 1350, 1352, 1354, 1366, 1358 and 1360 are attached to the wall 1347, as illustrated in FIG. 52. The ICI 1340 may be implanted in a skull by laser ablating a passage having a hexagonal cross-section in the calvarial bone of the skull.

Figure 53:
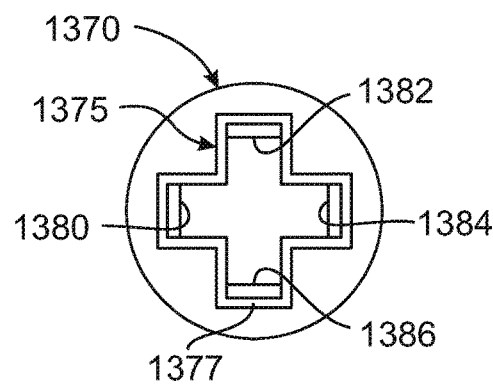

Turning to FIG. 53, the ICI 1370 (shown in bottom view) has a current directing mechanism 1305 having a square cross-section. The current directing mechanism 1375 has a wall 1377 having a cross-like cross-sectional shape. Four electrodes 1380, 1382, 1384 and 1386 are attached to the wall 1377, as illustrated in FIG. 53. The ICI 1370 may be implanted in a skull by laser ablating a passage having a cruciform cross-section in the calvarial bone of the skull.

It will be appreciated that the different shapes of the current directing mechanisms illustrated in FIGS. 50-53 are by no way limiting and that the currently directing mechanisms of the ICIs of the present application may also have asymmetrically or irregular cross-sectional shapes. Such irregularly and/or asymmetrically shaped current directing mechanisms may be advantageous in cases in which the cortical regions to be stimulated by the ICIs have irregular shapes that may not be easily stimulated by symmetrical current directing mechanisms. This type of current directing mechanism may advantageously be used to more efficiently match the shape of the current directing mechanism to different irregularly shaped cortical regions in need of stimulation or sensing. And may allow to manufacture specifically shaped ICIs to match cortical regions of specific individual patients having somewhat different cortical anatomy.

It is noted that the multi-ICI systems of the present application may include any possible combinations of the types of ICIs disclosed in the present application.

Beyond using variable direct stimulation of cortical regions, the location and timing of stimulation could be configured to stimulate or inhibit deeper regions of the brain. By delivering to the brain multiple electric fields at frequencies too high to recruit neural firing, but which differ by frequency to generate a beat frequency which is within the dynamic range of neural firing, one can electrically stimulate neurons throughout a region where interference between the multiple fields results in a prominent electric field envelope modulated at the difference frequency. The methods for performing such frequency interference (FI) stimulation are disclosed in detail in the article by Grossman et al. referenced hereinabove.

International publication No. WO 2018/109715 discloses the use of BCIs for sensing and stimulation of cortical regions and/or deeper brain structures using Ecog electrode arrays and other recording/stimulating surface electrodes for enhancing intelligence. The sensing, data processing and stimulation methods used in WO 2018/109715 may also be adapted for use with any of the ICIs and ICI systems disclosed in the present application, by using the ICIs disclosed herein instead of (or in addition to) the Ecog arrays and/or FI scalp electrodes disclosed in WO 2018/109715.

Intra-calvarial recording from and/or stimulating the cortical surface of the brain may enable neuro-modulation of electrophysiology that may have a wide range of clinical and non-clinical applications. In clinical applications of some embodiments, the cortical stimulation may be used to modify cortical excitability to treat numerous neuropsychiatric diseases such as, but not limited to, depression, ADHD, addiction, and obesity. From a purely recording standpoint, cortical signals may be used for brain computer interfaces that may be used to treat a wide array of motor disabilities. From a non-clinical perspective, modulating the brain physiology either through stimulation or recording methodologies can be used to enhance cognitive function. Depending on the modality, the location in the brain, and the interface regime, cognitive operations such as attention, memory, analytic abilities, and mood may all be enhanced beyond a given individual's normal baseline.

A barrier for more wide spread adoption of these type of approaches is the invasiveness of the implantation of the electrodes. Once the skull bone and dura mater are penetrated with either intra-parenchymal or electrocorticographic electrodes there is a risk of having an intracranial hemorrhage or infection that could cause major harm, morbidity, or even death. While these risks, generally speaking, are quite small, the mere fact that they exist substantially changes a patient's perception of considering adoption of such invasive procedures. This also changes the manner in which patients are treated by physicians after implantation. If an intracranial electrode implant is surgically placed (e.g. deep brain stimulator, cortical stimulator, etc.), at the very least the patients are kept overnight for observation in a hospital to ensure that, should an intracranial complication arise, it can be rapidly addressed. A major need is to have a recording and stimulation brain interface that has minimal risk of an intracranial complication yet is still able to record and stimulate the brain with a functional equivalence similar or very close to that of the intracranial approaches. The presently disclosed ICIs, ICI systems, and methods of their construction and use may effectively and safely address many of the problems of the currently used intracranial methods.

It is noted that the processor/controllers disclosed herein may be or may include one or more computing devices selected from, one or more intracranial processor/controller, wearable processor/controller, remote processor/controller, a digital signal processor (DSP), a graphic processing unit (GPU), a quantum computing device, a central processing unit (CPU), or any combinations of the above. In some embodiments, the processor/controller may include and/or emulate a neural network. For example, the processor/controller(s) 140 or any other processors/controllers disclosed herein may include or may be connected to one or more neuromorphic ICs. Alternatively and/or additionally, the processor/controller 140 or any other processors/controllers disclosed in the present application may be programmed to emulate one or more neural networks by software operative on the processor/controller(s).

Furthermore, any of the processor/controllers disclosed in the present application may have access to the "cloud" via the internet (preferably, wirelessly, but also possibly in a wired way) or through any other type of network, such as, for example, a LAN, a WAN, a VPN or any other type of wired or wirelessly accessible network.

In some embodiments, the processor/controller(s) disclosed herein may include wireless communication circuits, such as Bluetooth, or WiFi communication units or circuits (not shown in detail any of the figures for the sake of clarity of illustration). Such wireless communication means may enable the processor/controller(s) to wirelessly communicate with external devices, such as for example, a remote computer, a server, a cellular telephone, a laptop computer, a VR headset, an AR headset or any other type of device having wireless communication capabilities (such as, for example, the device 202 of FIG. 28. Such embodiments may be useful in cases in which the processing power of the processor/controller(s) is limited. Such embodiments may allow the offloading of some or all of the computational burden to other processing devices, such as remote computer(s), servers, a cluster of computers, cellular smartphones, cellular telephones, a Pablet, a tablet or any other suitable computing devices, and may enable the use of cloud computing, or parallel computing for processing data.

It is noted that in some embodiments of the ICIs of the present application, the implanted ICIs and/or other components of the ICI systems disclosed herein may be made MRI-compatible to enable use of the implanted ICIs during performing of fMRI imaging procedures. This may be performed by selecting non-magnetic and/or non-magnetizable materials to be used in the construction of the components of such ICIs. Such material may include, as an example, titanium, organic polymers or polymer based materials such as, Kevlar®, Parylene®, ceramic materials and other suitable materials. In such MRI-compatible embodiments, the power harvesting induction coils may be replaced by other types of power harvesting modules, such as, for example ultrasound energy harvesting modules using an implanted piezoelectric element coupled to the power harvesting units of the ICI. The use of fMRI compatible ICIs may be advantageous because it may allow the performing of complementary fMRI imaging to monitor the operation of the implantable system disclosed herein during implantation, testing and/or calibrating of the systems, as well as for tuning and/or adjusting the sensing and/or the stimulating regimes to improve or optimize system's performance. Additionally, the performing of fMRI imaging may assist the procedure of implantation, as disclosed in detail hereinabove.

In some embodiments of the systems and methods disclosed herein, the patient may undergo both anatomic imaging and functional imaging to define the optimal placement of the implanted ICI. For example, patients may be scanned using 3-T MRI scanners (such as but not limited to 3-T MRI scanners commercially available from Siemens, Erlangen, Germany). Anatomic imaging may include T1-weighted magnetization-prepared rapid acquisition gradient echo (MP-PAGE), T2-weighted fast spin echo, susceptibility-weighted imaging (SWI), diffusion-weighted imaging (DWI) and pre and post gadolinium T1-weighted fast spin echo in multiple projections. fMRI data may be acquired, for example, by using a T2* EPI sequence ($3\times3\times3$-mm$^3$ voxels; 128 volumes/run; TE=27 ms; TR=2.8 s; field of view=256 mm; flip angle=90°), while the patients are instructed to remain still and fixate on a visual cross-hair without falling asleep (2 runs of 6 minute each for a total time of 12 minutes). Additionally, patients may also undergo CT scans with bone windows to determine the thickness of the skull. fMRI, CT and anatomic images may be co-registered using a stereotactic navigation system (for example Medtronic Stealth Navigation system commercially available from Medtronic, U.S.A. may be used for co-registration). The optimal implantation site will be determined using a combination of these imaging modalities. As an example, anatomic MRI imaging may be used to identify the dorsolateral prefrontal cortical region. Additionally, resting state or task based fMRI may be used to further refine the location for ICI implantation within the anatomical region.

An exemplary operative implantation of the ICI(s) may be performed as follows: the patient may be brought into the operating room and induced under general anesthesia. Once the implantation site is identified in imaging space, the implantation location may be localized on the patient's head using a stereotactic navigation system. The implantation site may then be prepared and draped in standard surgical fashion. The skin of the scalp may be infiltrated with a local anesthetic and a 1 cm incision may be made. A small retractor may be placed in the incision and the surface of the skull is exposed. An opening in the outer table 5 of the calvarial bone 4 may then be made (by drilling and/or burring or laser ablating or any other suitable surgical method to accommodate the dimensions and specific structure of the ICI being used (as described hereinabove for the various different types of implants). The bone thickness at the site planned for implantation may be determined from the CT scan of the skull performed prior to implantation.

For example, for the ICI 10 illustrated in FIGS. 1-9, the cavities 50 and 52 may be drilled by using the guide-rod 42 and the drill bits 44 and 46 (of FIGS. 8-10) as disclosed in detail hereinabove. The housing 20 of the ICI 10 may be inserted into the cavity 50 such that the wall 27 is disposed within the annular cavity 52. The shimming member 34 may then be attached to the top part 24A of the sealed compartment 24 by a suitable method (such as, for example by press-fitting), and the shimming member 34 may then be firmly attached to the outer table 5 by inserting the screws 36A and 36B through the openings 34C and 34D of the tabs 34A and 34B, respectively, and screwing the screws 36A and 36B into the calvarial bone 4. Once the ICI 10 is implanted in the skull, the wound may be irrigated and the scalp may surgically be closed and allowed to heal.

It is noted that while the ICIs and ICI systems disclosed in the present application are designed mainly for implantation in human patient, they may also be implanted in the calvarial bone of any other mammal either as they are described herein or in a scaled down or scaled up versions having different dimensions to match the thickness of the calvarial bone of the mammal in which they are to be implanted. Such ICIs may be implanted in non-human mammals for research purposes or other commercial applications.

It is noted that an aspect of the current directing mechanisms is that it enables to reduce the stimulation (or inhibition) "footprint" of the ICI. As the electrodes are oriented substantially vertically with respect to the inner table 6, the number and the surface area of the electrodes may be substantially increased while still confining most of the stimulation currents close to the current directing mechanism. This aspect may advantageously allow "focusing" or constraining the spread of the stimulating currents over a smaller and more precisely define area and may result in more precisely defined cortical region stimulation.

Another advantageous aspect of the ICIs of the present application is that multiple electrodes may be placed within the current directing mechanisms disclosed herein. By varying the amount of current delivered through different electrodes the current density within the current directing mechanism may be varied. This may allow even more precision in targeting specific sub-regions in the cortical region underlying the ICI or in the vicinity of the ICI.

It is appreciated that certain features of the in invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An intra-calvarial implant (ICI) for implantation in a calvarial bone of a mammal having an outer table, a cancellous bone, and an inner table, the ICI comprising:
    one or more electrodes for sensing electrical signals from a cortex of a mammal and/or for electrically stimulating one or more regions of a brain of the mammal;
    one or more auxiliary electrodes operable as one or more current return electrodes or as one or more reference electrodes or as one or more current return electrodes and one or more reference electrodes;
    a housing comprising a sealed compartment having a top part, a bottom part and a side wall extending between the top part and the bottom part, and a current augmenting mechanism, the current augmenting mechanism comprises at least one electrically non-conducting member having a first end sealingly attached to or extending away from the bottom part of the sealed compartment and surrounding the one or more electrodes, the current augmenting mechanism has at least one open end disposed at a second end of the non-conducting member, the open end is configured to direct currents from the one or more electrodes towards the inner table, the current augmenting mechanism is configured to augment the current density in the inner table and in cortical target regions underlying the inner table by reducing or preventing lateral current flow through the electrically non-conducting member from the one or more electrodes to the one or more current return electrodes;
    an electronic circuitry module (ECM) sealingly disposed within the sealed compartment and operatively electrically connected to the one or more electrodes and to the one or more auxiliary electrodes, the ECM is configured for controlling the operation of the ICI and for wirelessly communicating with an external telemetry device; and
    a power harvesting device suitably electrically connected to the ECM of the ICI for providing power thereto.

2. The ICI according to claim 1, wherein the current augmenting mechanism is an integral part of the housing or attached to the bottom part of the sealed compartment.

3. The ICI according to claim 1, wherein the sealed compartment is selected from the following:
    a cylindrical sealed compartment having a bottom part having a bottom part diameter, and a frustoconical shaped sealed compartment having a bottom part with a bottom part diameter and a top part with a top part diameter wherein the top part diameter is larger than the bottom part diameter.

4. The ICI according to claim 1, wherein the current augmenting mechanism comprises a cylindrically shaped wall having a height H, the cylindrically shaped wall has a first end attached to or extending from the bottom part of the sealed compartment and a second end having a circularly shaped opening with a radius R.

5. The ICI according to claim 4, wherein H>0.5 R.

6. The ICI according to claim 1, wherein the current augmenting mechanism comprises a non-cylindrical wall.

7. The ICI according to claim 6, wherein the cross-sectional shape of the non-cylindrical wall is selected from the group consisting of an oval shape, an elliptical shape, a polygonal shape, an irregular shape and a cross-like shape.

8. The ICI according to claim 1, wherein the one or more electrodes are attached to an internal surface of the wall of the current augmenting mechanism or disposed adjacent to the internal surface of the wall of the current augmenting mechanism.

9. The ICI according to claim 1, wherein the one or more auxiliary electrodes are
    attached to the bottom part of the sealed compartment and/or attached to the side wall of the sealed compartment.

10. The ICI according to claim 1, wherein the one or more electrodes are adapted to be implanted between the outer table and the inner table of the calvarial bone without fully penetrating the inner table.

11. The ICI according to claim 1, wherein the at least one or more auxiliary electrodes is adapted to be disposed on one of the following locations:
    between the outer table and the inner table of the calvarial bone;
    adjacent to at least part of the outer table of the calvarial bone;
    within the cancellous bone of the calvarial bone; and
    on top of the housing of the ICI.

12. The ICI according to claim 1, wherein the at least one or more auxiliary electrodes are selected from one of the following:
    a reference electrode and a current return electrode separated from the reference electrode and electrically isolated therefrom;
    a reference electrode and a separate current return electrode, wherein the reference electrode is electrically connected to the current return electrode; and
    at least one electrode operating as a current return electrode when the ICI is used for stimulating and as a reference electrode when the ICI is used for sensing.

13. The ICI according to claim 4, wherein the cylindrically shaped wall has a diameter selected from:
    the diameter of the cylindrically shaped wall which is smaller than the bottom part diameter of the sealed compartment, and
    the diameter of the cylindrically shaped wall which is equal to the bottom part diameter of the sealed compartment.

14. The ICI according to claim 1, wherein the ICI includes one or more ground electrodes selected from:
    a ground electrode attached on the top part of the sealed compartment, and
    a ground electrode attached to the side walls of the sealed compartment.

15. The ICI according to claim 1, wherein the current augmenting mechanism comprises:
    a first cylindrically shaped electrically non-conducting wall having a first end attached to or extending from the bottom part of the sealed compartment and a second end having a circularly shaped opening and, the first wall has a first outer diameter, and
    a second cylindrically shaped electrically non-conducting wall concentric with the first wall, the second wall has a first end attached to or extending from the bottom part of the sealed compartment and a second end having a circularly shaped opening, the second wall has a second outer diameter, wherein the second outer diameter is smaller than the first outer diameter.

16. The ICI according to claim 15, wherein the first wall has a first wall height H1 and the second wall has a second wall height H2, and wherein H1 and H2 are selected from one of the following relationships:
    H1=H2;
    H1>H2; and
    H1<H2.

17. The ICI according to claim 16, wherein the first wall has an inner surface has a radius R1 and the second wall has an inner surface has a radius R2, and wherein H1>0.5R1 and H2>0.5R2.

18. The ICI according to claim 15, wherein the one or more electrodes are selected from one or more of the following:
    the one or more electrodes is disposed between the first wall and the second wall;
    the one or more electrodes is attached to the first wall; and
    the one or more electrodes is attached to the second wall.

19. The ICI according to claim 15, wherein the outer diameter of the first cylindrically shaped wall is selected from
    the outer diameter of the first cylindrically shaped wall is equal to the bottom part diameter of the sealed compartment, and
    the outer diameter of the first cylindrically shaped wall is smaller than the bottom part diameter of the sealed compartment.

20. The ICI according to claim 1, wherein the current augmenting mechanism comprises a plurality of concentric cylindrical walls and wherein the one or more electrodes are disposed between the plurality of walls and/or on an inner surface of the innermost wall of the plurality of walls.

21. The ICI according to claim 1, wherein, after implantation of the ICI, the one or more electrodes are adapted to be substantially perpendicular to the inner table of the calvarial bone.

22. The ICI according to claim 1, wherein, after implantation of the ICI, at least one electrode of the one or more auxiliary electrode is adapted to be substantially parallel to the inner table of the calvarial bone.

23. The ICI according to claim 1, wherein at least some electrodes of the one or more electrodes and the one or more auxiliary electrodes are made from or comprise a material selected from the group consisting of platinum, a platinum/iridium alloy and graphene.

24. The ICI according to claim 1, wherein the power harvesting device comprises an induction coil electrically connectable to a current conditioning circuit, the current conditioning circuit is selected from a current conditioning circuit formed as an integral part of the ECM and a current conditioning circuit separate from and electrically connected to the ECM.

25. The ICI according to claim 24, wherein the power harvesting device also includes an electrical charge storage device electrically coupled to the current conditioning circuit and to the ECM.

26. The ICI according claim 24, wherein the induction coil is located in one of the following locations:
the induction coil disposed within the sealed compartment,
the induction coil integrated into the ECM,
the induction coil disposed outside the sealed compartment, and
the induction coil disposed on or within a shimming member included in the ICI.

27. The ICI according to claim 1, wherein the ICI also includes a shimming member adapted for attaching to the outer table of the calvarial bone over the top part of the sealed compartment.

28. The ICI according to claim 27, wherein the shimming member comprises two or more tabs having holes therein for inserting screws into the holes to attach the shimming member claim.

29. The ICI according to claim 27, wherein the shimming member also comprises a magnet.

30. The ICI according to claim 1, wherein the ICI is a stimulating ICI and wherein the ECM is programmed for controlling the stimulation of the brain using the one or more electrodes and for wirelessly receiving stimulation control signal from an external telemetry device or from another ICI in wireless communication with the stimulating ICI.

31. The ICI according to claim 1, wherein the ICI is a sensing/recording ICI and wherein the ECM is programmed to perform one of the following:
controlling the sensing and/or recording of electrical signals from the brain using the one or more electrodes and the at least one reference electrode and for wirelessly transmitting signals recorded from the brain to the external telemetry device or to another ICI in wireless communication with the sensing/recording ICI;
controlling the sensing and/or recording of electrical signals from the brain using the one or more electrodes and the at least one reference electrode, for at least partially processing recorded signals to obtain data and for wirelessly transmitting the data to the external telemetry device, or to another ICI in wireless communication with the sensing/recording ICI; and
controlling the sensing and/or recording of electrical signals from the brain using the one or more electrodes and the at least one reference electrode, for digitizing the recorded signals and for processing digitized signals to detect an indication of a physiological and/or a neurological and/or a neuropsychiatric state of the mammal and for wirelessly transmitting the indication data and/or stimulation control signals to the external telemetry device or to another ICI in communication with the sensing/recording ICI.

32. The ICI according to claim 1, wherein the ICI is a sensing/recording and stimulating ICI and wherein the ECM is programmed to perform one of the following:
controlling the sensing and/or recording of electrical signals from the brain using the one or more electrodes and the at least one reference electrode and for wirelessly transmitting signals recorded from the brain to the external telemetry device and/or to another ICI in wireless communication with the sensing/recording and stimulating ICI;
controlling the sensing and/or recording of electrical signals from the brain using the one or more electrodes and the at least one reference electrode, for at least partially processing recorded signals to obtain data and for wirelessly transmitting the data to the external telemetry device and/or to another ICI in wireless communication with the sensing/recording and stimulating ICI;
controlling the sensing and/or recording of electrical signals from the brain using the one or more electrodes and the at least one reference electrode, for digitizing the recorded signals and for processing digitized data to detect an indication of a physiological and/or a neurological and/or a neuropsychiatric state of the mammal and for wirelessly transmitting the indication data to an external telemetry device and/or to another ICI in communication with the sensing/recording ICI; and
controlling the sensing and/or recording of electrical signals from the brain using the one or more electrodes and the at least one reference electrode, for digitizing the recorded signals and for processing digitized data for detecting an indication of a physiological and/or a neurological and/or a neuropsychiatric state of the mammal, for autonomously stimulating the brain using the one or more electrodes responsive to the detecting of the indication, for wirelessly communicating with the external telemetry device and/or with another ICI in communication with the sensing/recording and stimulating ICI.

33. The ICI according to claim 1, wherein the ICI is part of an ICI system comprising at least one more ICI adapted to be implanted in the same calvarial bone.

34. The ICI according to claim 1, wherein the mammal is a human.

35. The ICI according to claim 1, wherein the current augmenting mechanism is a multi-channel current augmenting mechanism comprising a plurality of hollow channels.

36. The ICI according to claim 35, wherein each channel of the plurality of channels has one electrode of the one or more electrodes disposed therein.

37. The ICI according to claim 1, wherein the power harvesting device is selected from the list consisting of an electromagnetic induction based power harvesting device and an ultrasonic energy based power harvesting device.

38. The ICI according to claim 1, wherein the current augmenting mechanism comprises a single cylindrically shaped wall having a first end extending from the bottom part of the sealed compartment or attached to the bottom part of the sealed compartment and a second open end, the one or more electrodes for sensing electrical signals from the brain of the mammal and/or for electrically stimulating one or more regions of the brain comprise a stimulating electrode disposed within the current augmenting mechanism, and the one or more auxiliary electrodes comprise a current return electrode.

39. The ICI according to claim 38, wherein the stimulating electrode is a tubular stimulating electrode disposed within the single cylindrically shaped wall or attached thereto.

40. The ICI according to claim 38, wherein the current return electrode is disposed on one of the following locations including:
the top part of the sealed compartment,
the bottom part of the sealed compartment, and
the side wall of the sealed compartment.

41. The ICI according to claim 38, wherein the one or more electrodes of the ICI also include at least one sensing electrode disposed on or attached to the second end of the cylindrically shaped wall and a reference electrode.

42. The ICI according to claim 41, wherein the reference electrode is disposed on one of the following locations including the top part of the sealed compartment,
the bottom part of the sealed compartment, and
the side wall of the sealed compartment.

43. The ICI according to claim 38, wherein the cylindrically shaped wall is configured to be disposed within a tubular shaped passage drilled into the calvarial bone without breaching the inner table of the calvarial bone and wherein the bottom part of the sealed compartment is configured to be attached to an outer surface of the outer table of the calvarial bone.

44. The ICI according to claim 43, wherein after implantation, the sealed compartment is disposed between the outer table of the calvarial bone and the scalp.

45. An ICI system comprising two or more ICIs, each of the two or more ICIs according to claim 1, the two or more ICIs are adapted to be implanted in the same calvarial bone of the mammal.

46. The ICI system according to claim 45, wherein the two or more ICIs are configured for sensing/recording of electrical brain signals and/or electrical brain stimulating.

47. The ICI system according to claim 45, wherein the two or more ICIs of the ICI system are selected from one of the following:

a master ICI configured for wirelessly receiving sensed brain electrical signals from one or more ICIs of the ICI system, processing the signals to detect an indication of a physiological and/or neurological and/or neuropsychiatric state of the mammal, and for wirelessly controlling brain stimulating operation of the one or more ICIs of the system;

a master ICI configured for wirelessly receiving sensed signals from one or more ICIs of the ICI system, for sensing brain electrical signals, for processing the received signals and the signals sensed by the master ICI to detect an indication of a physiological and/or neurological and/or neuropsychiatric state of the mammal, and for wirelessly controlling the stimulating operation of the one or more ICIs of the system;

a master ICI configured for wirelessly receiving sensed signals from one or more ICIs of the ICI system, for sensing brain electrical signals, for stimulating the brain, for processing the received signals and the signals sensed by the master ICI to detect an indication of a physiological and/or neurological and/or neuropsychiatric state of the mammal, or wirelessly controlling the stimulating operation of the one or more ICIs of the system and for synchronizing the stimulation performed by the one or more ICIs with the stimulation performed by the master ICI;

a master ICI configured for wirelessly receiving sensed signals from one or more ICIs of the ICI system, for sensing brain electrical signals, for processing the received signals and the signals sensed by the master ICI to detect an indication of a physiological and/or neurological and/or neuropsychiatric state of the mammal and for wirelessly controlling the stimulating operation of the one or more ICIs;

a slave ICI configured for performing sensing/recording of brain electrical signals and for wirelessly transmitting sensed signals to a master ICI adapted to be implanted in the same calvarial bone;

a slave ICI configured for stimulating the brain of the mammal and for wirelessly receiving stimulation control signals from a master ICI adapted to be implanted in the same calvarial bone; and a slave ICI configured for performing sensing/recording of brain electrical signals, for wirelessly transmitting sensed signals to a master ICI adapted to be implanted in the same calvarial bone, for stimulating the brain of the mammal, and for wirelessly receiving stimulation control signals from the master ICI adapted to be implanted in the same calvarial bone.

48. The ICI system according to claim 45, wherein the one or more ICIs included in the ICI system are configured for wirelessly communicating with an external controller/processor for performing one or more of the following:

transmitting sensed electrical brain signals to the external controller processor; and receiving stimulation control signals from the external controller/processor.

49. A method of augmenting current flowing from one or more stimulating electrodes of an ICI into a cortex through the inner table of a calvarial bone, the method comprises the steps of, implanting the ICI according to claim 1 in the calvarial bone such that at least part of the inner table, a pia matter and a dura matter intervene between the cortex underlying an inner table of the calvarial bone and the current augmenting mechanism of the ICI; and passing a current between at least one electrode of the one or more electrodes and at least one of the one or more auxiliary electrodes.

50. The method according to claim 49, wherein the current is selected from a cortical stimulating current and a cortical inhibiting current.

51. The method according to claim 49, wherein the at least on electrode of the one or more electrodes operates as a cathode or an anode.

52. The method according to claim 49, wherein the current is a pulsed current.

53. The method according to claim 49, wherein the current augmenting mechanism is adapted to augment one or more parameters including the current's rise-time and the current density within a given cortical tissue volume.

54. The method according to claim 49, wherein the current augmenting mechanism is adapted to change the spatial distribution pattern of the current flowing into the cortex.

* * * * *